(12) United States Patent
Thomas et al.

(10) Patent No.: US 6,234,953 B1
(45) Date of Patent: May 22, 2001

(54) ELECTROTHERAPY DEVICE USING LOW FREQUENCY MAGNETIC PULSES

(75) Inventors: Alex W. Thomas; Frank S. Prato; Martin I. Kavaliers, all of London; Michael A. Persinger, Sudbury, all of (CA)

(73) Assignee: Lawson Research Institute, London (CA)

( * ) Notice: Subject to any disclaimer, the term of this patent is extended or adjusted under 35 U.S.C. 154(b) by 0 days.

(21) Appl. No.: 09/194,930

(22) PCT Filed: Jun. 5, 1997

(86) PCT No.: PCT/CA97/00388

§ 371 Date: Jan. 20, 1999

§ 102(e) Date: Jan. 20, 1999

(87) PCT Pub. No.: WO97/46277

PCT Pub. Date: Dec. 11, 1997

Related U.S. Application Data

(60) Provisional application No. 60/019,184, filed on Jun. 6, 1996.

(51) Int. Cl.[7] .................................................... A61N 2/00
(52) U.S. Cl. .................................................................. 600/14
(58) Field of Search .................................. 600/9, 13, 14, 600/26–28, 544, 545; 128/897–898; 454/236–238

(56) References Cited

U.S. PATENT DOCUMENTS 5,935,054 * 8/1999 Loos ........................................ 600/9

* cited by examiner

Primary Examiner—John P. Lacyk
Assistant Examiner—Joseph Cadugan
(74) Attorney, Agent, or Firm—Alston & Bird LLP

(57) ABSTRACT

An apparatus and method for treating a disorder selected from the group of physiological, neurological and behavioral disorders, the method comprising applying to a subject a specific low frequency pulsed magnetic field (Cnp) having a plurality of intermittent waveforms, for a time effective to produce a desired effect in a target tissue.

28 Claims, 33 Drawing Sheets

ELECTROTHERAPY DEVICE USING LOW FREQUENCY MAGNETIC PULSES

This application of PCT/CA97/00388 filed Jun. 5, 1997 and also claims the benefit of provisional no. 60/019,184 filed Jun. 6, 1996.

FIELD OF THE INVENTION

This invention relates to magnetic fields and in particular, to the use of specifically designed low frequency pulsed magnetic fields (Cnps) for modifying a variety of clinical physiological and neurological behaviors and conditions in vertebrates and invertebrates.

BACKGROUND OF THE INVENTION

Diverse studies have shown that the behavioral, cellular and physiological functions of animals can be affected by magnetic stimuli. Weak magnetic fields exert a variety of biological effects ranging from alterations in cellular ion flux to modifications of animal orientation and learning, and therapeutic actions in humans. A number of magnetic field exposures have been shown to reduce exogenous opiate (e.g. morphine) and endogenous opioid peptide (e.g. endorphin) mediated analgesia in various species, including humans (Kavaliers & Ossenkopp 1991; Prato et al., 1987; Betancur et al., 1994; Kavaliers et al., 1994; Del Seppia et al., 1995; and Papi et al., 1995). As well, extremely low frequency (ELF) magnetic field exposures are reported to modify homing pigeon behavior (Papi et al., 1992) and spatial learning in rodents (Kavaliers et al., 1993, 1996) in a manner consistent with alterations in opioid function.

There are several theories addressing the mechanism of the effect of low frequency magnetic field exposure on tissues. For example, low frequency magnetic field exposures have been proposed to exert their effect(s) through the induction of electric currents (Polk 1992; and Weaver & Astumian 1990). Weak magnetic fields have also been proposed to be detected by particles of magnetite in tissue and by virtue of this detection have a physiological effect (Kirschvink & Walker 1985); however, this magnetite based mechanism is not widely believed (Prato et al., 1996).

Extremely low frequency (ELF) magnetic fields are a physical agent which have little attenuation in tissue and therefore, can be used to alter endogenous processes provided they can be detected and their detection can be coupled to a physiological process. It is now shown that magnetic fields may be designed as time varying signals such that they can be used to alter specific targeted physiological processes and in this manner can be used to treat/modify various neurological and physiological conditions and behaviors. It was therefore an object of the present invention to provide novel specific low frequency pulsed magnetic fields having a plurality of intermittent waveforms for use to treat a variety of physiological, neurological and behavioral disorders in both vertebrates and in invertebrates.

SUMMARY OF THE INVENTION

The applicants have now designed and characterized complex low frequency pulsed magnetic fields (Cnps) and their effects on physiological, neurological and behavioral conditions. The low frequency pulsed magnetic fields are specifically designed to target and alter complex neuroelectromagnetic applications and permit the development of therapeutic strategies in order to treat and/or alter various physiological, neurological and behavioral disorders.

Broadly stated, the present invention relates to complex low frequency pulsed magnetic fields (Cnps) which are designed and used as a therapeutic treatment for disorders and behaviors including: alleviation of pain and anxiety; restoration of balance; improved learning; treatment of epilepsy; and depression; and for moderating eating habits.

In accordance with an aspect of the present invention there is provided a therapeutic method for treating physiological, neurological and behavioral disorders, the treatment comprising: subjecting a mammal to a specific low frequency pulsed magnetic field having a plurality of waveforms designed with a length and frequency relative to the target tissue intermittent with a built-in variable latency period and a fixed refractory period, for a time effective to produce a desired physiological effect.

The method of the present invention if not completely, at least partially, averts the development of tolerance which is typical with repeated administrations of analgesic drugs and in particular, opioids. The method also decreases the need to use pharmacological agents to treat and alleviate various physiological, neurological and behavioral conditions. In addition, the low frequency pulsed magnetic fields can be designed with specific waveforms to target specific tissues to affect different physiological functions without presentation of unwanted side effects.

Other objects, features and advantages of tie present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 2 shows the portion of the time axis which has been expanded. Sub-label 1 corresponds to the waveform and sub-label 2 to the latency period.

Response latencies were recorded prior to (Pre) and after (0, 15, 30, 60 min) exposure. Response latencies from days 1, 3, 6 and 9 are shown. There were no significant differences within the sham groups, hence the groups were collapsed. Error bars represent the Standard Error of the Mean (SEM), and where not visible are embedded within the symbol.

FIG. 12 shows the effects of either (A) 15 min or (B) 30 min daily repeated exposures to either a specific pulsed magnetic field (Cnp) or (C) sham exposure condition on the thermal (40° C.) response latencies of individual hydrated snails (N=60), shown in 3-D perspective. Response latencies were recorded prior to (Pre) and after (0, 15, 30, 60 min) exposure. There were no significant differences within the sham exposure or pre-exposure latencies.

FIG. 13 shows the effects of (A) 15 and (B) 30 min daily repeated acute exposure to a sham or specific pulsed magnetic field (Cnp) on the thermal (40° C.) response latencies (I 5 min post-exposure) of individual hydrated snails (N=60). Day 10 records the effects of condition reversal; in that, the previously sham exposed groups were exposed to the Cnp, and vice versa. Error bars represent the Standard Error of the Mean (SEM), and where not visible are embedded within the symbol.

Figure 14:
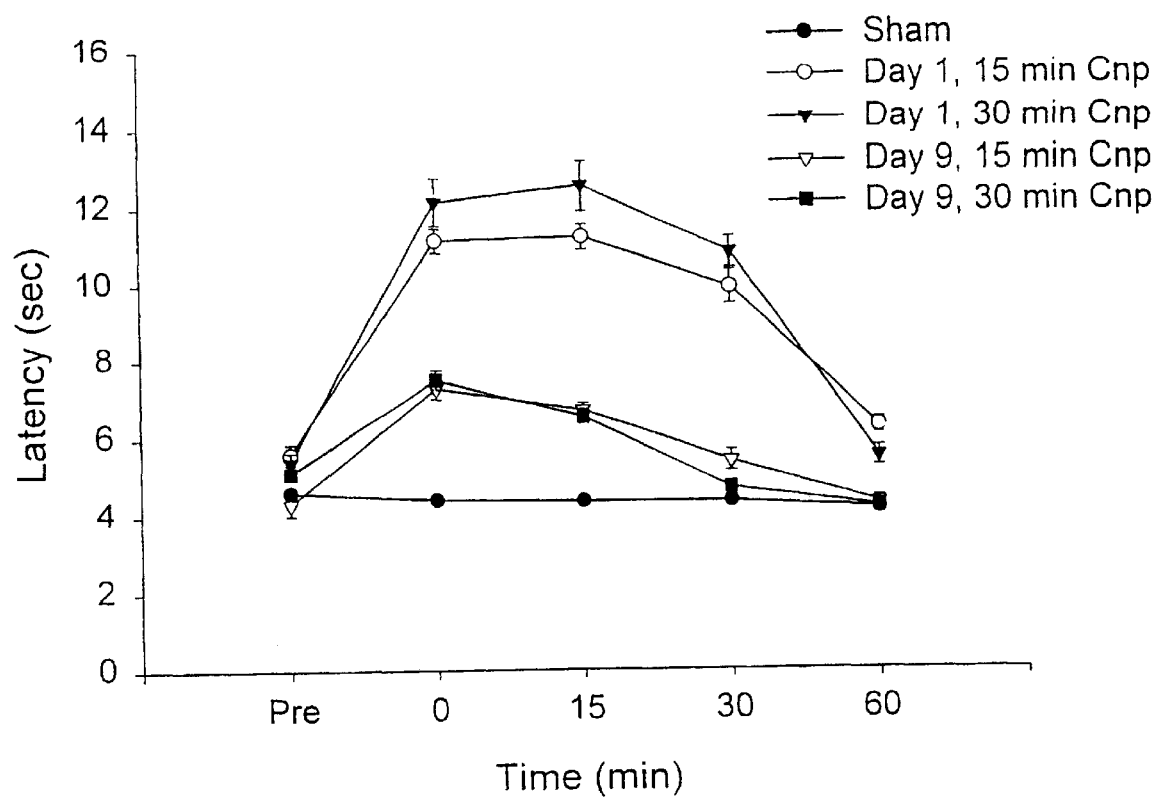

FIG. 14 shows thermal (40 ° C.) response latencies of snails (N=60) exposed to a specific pulsed magnetic field (Cnp) or sham condition for 15 or 30 min daily for 9 consecutive days. Response latencies were tested on days I and 9 prior to (Pre) and after (0, 15, 30, 60 min) exposures. There were no significant differences within the sham groups, hence the groups were collapsed. Error bars represent the Standard Error of the Mean (SEM), and where not visible are embedded within the symbol.

Figure 15:
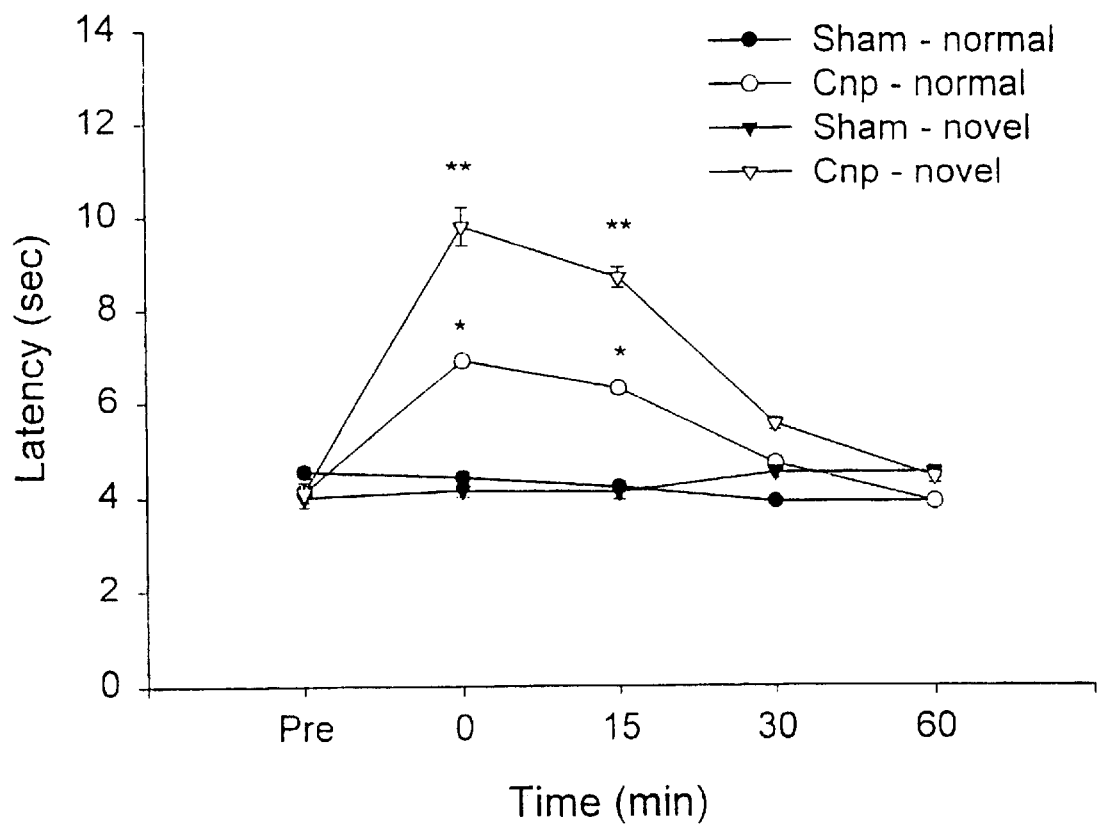

FIG. 15 shows thermal (40° C.) response latencies of individual snails (N=30) exposed for 15 min to either a specific pulsed magnetic field (Cnp) or sham magnetic field for 9 consecutive days (normal). On day 10 the snails were exposed to the Cnp or sham condition while under a novel environment condition (novel). Response latencies were tested prior to (Pre) and after (0, 15, 30, 60 min) exposure. Error bars represent the Standard Error of the Mean (SEM), and where not visible are embedded within the symbol. (*P<0.01 , **P<0.001)

Figure 16:
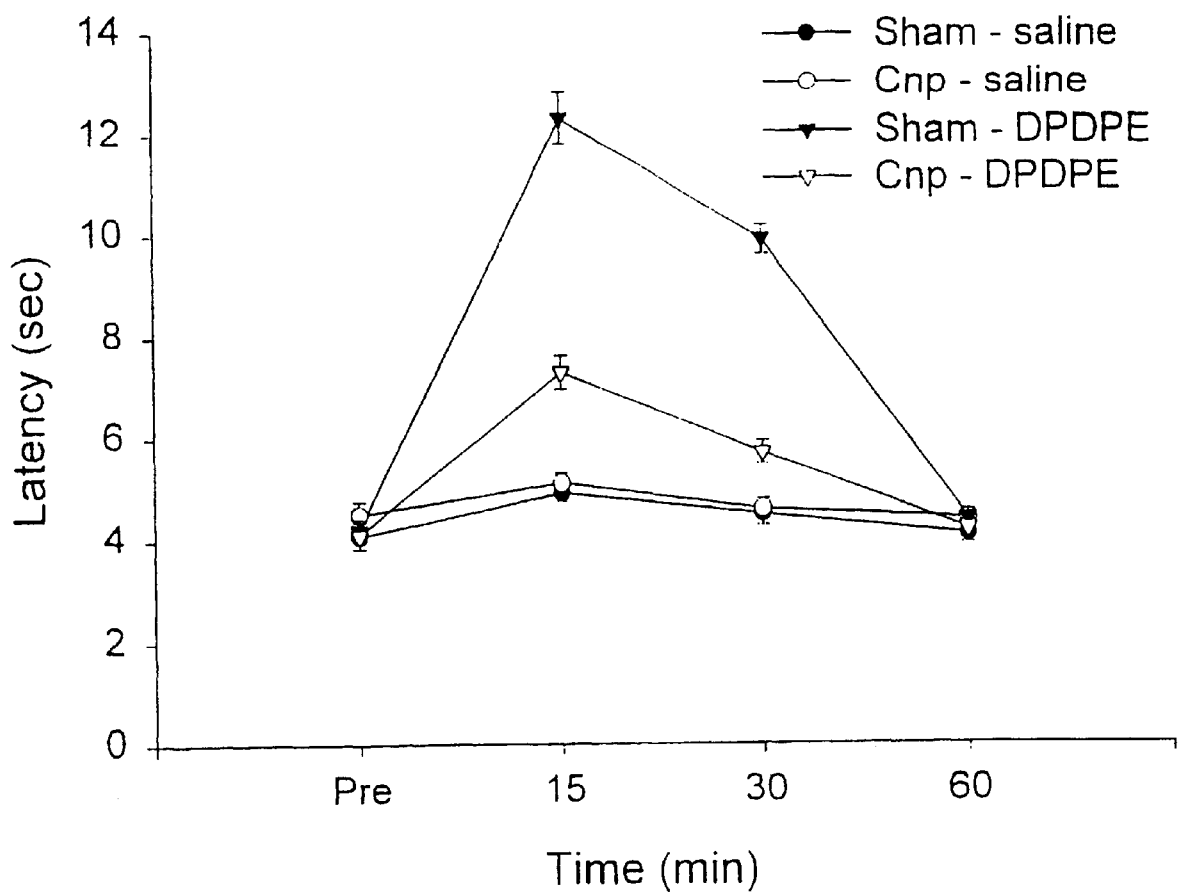

FIG. 16 shows thermal (40° C.) response latencies of individual snails (N60), that had been exposed for 15 min daily for 9 consecutive days to either a sham or Cnp. Response latencies were tested on day 10 prior to (Pre) and after being injected either with the δ opiate agonist, DPDPE, (0.05 μg/1.0 μl saline) or saline vehicle (1.0 μl) at 15, 30, 60 min intervals. Error bars represent the Standard Error of the Mean (SEM), and where not visible are embedded within the symbol.

Figure 17:
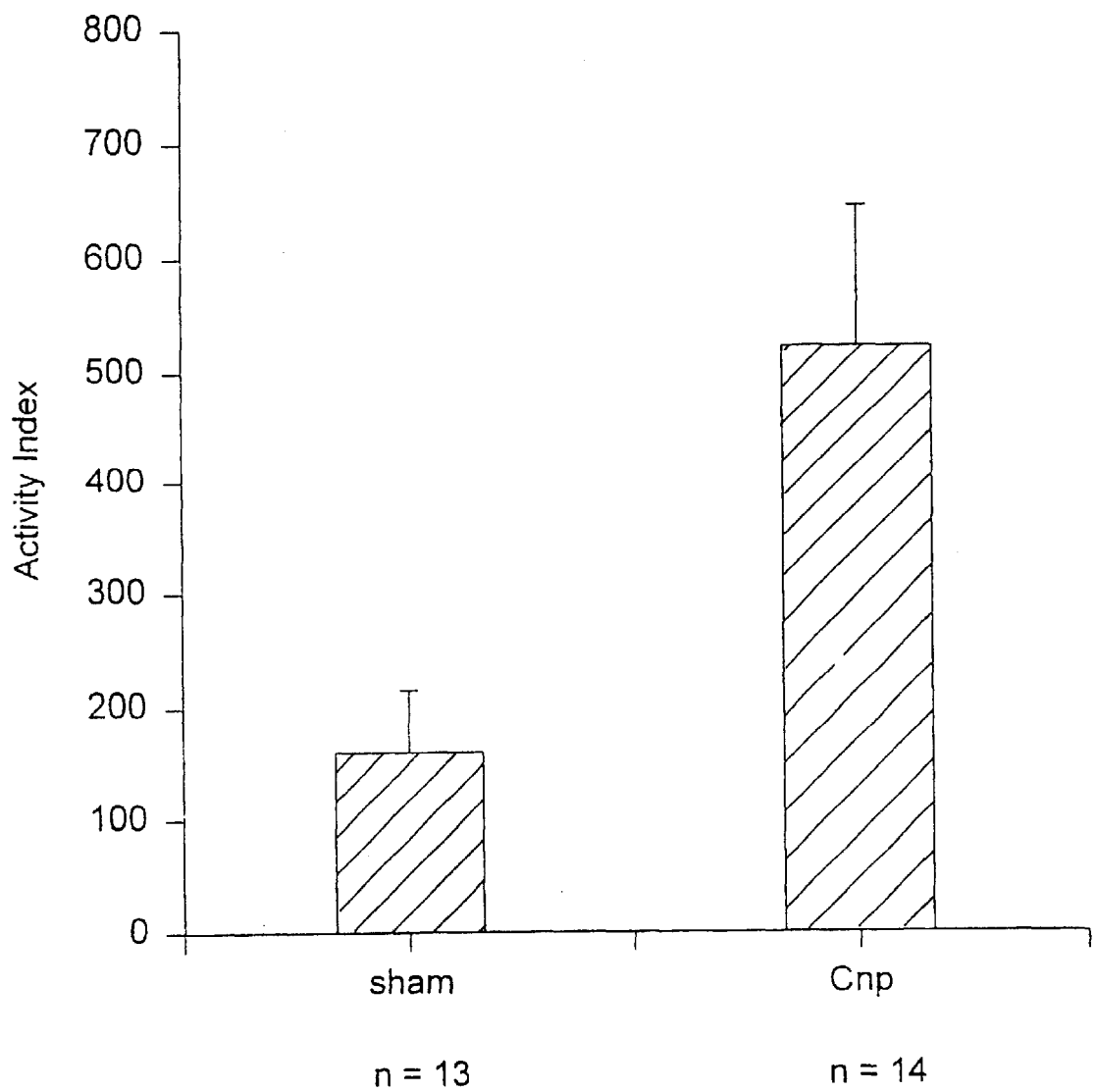

FIG. 17 shows Cnp induced activity in Deer mice. The Cnp shown in FIG. 3 was used.

Figure 18:
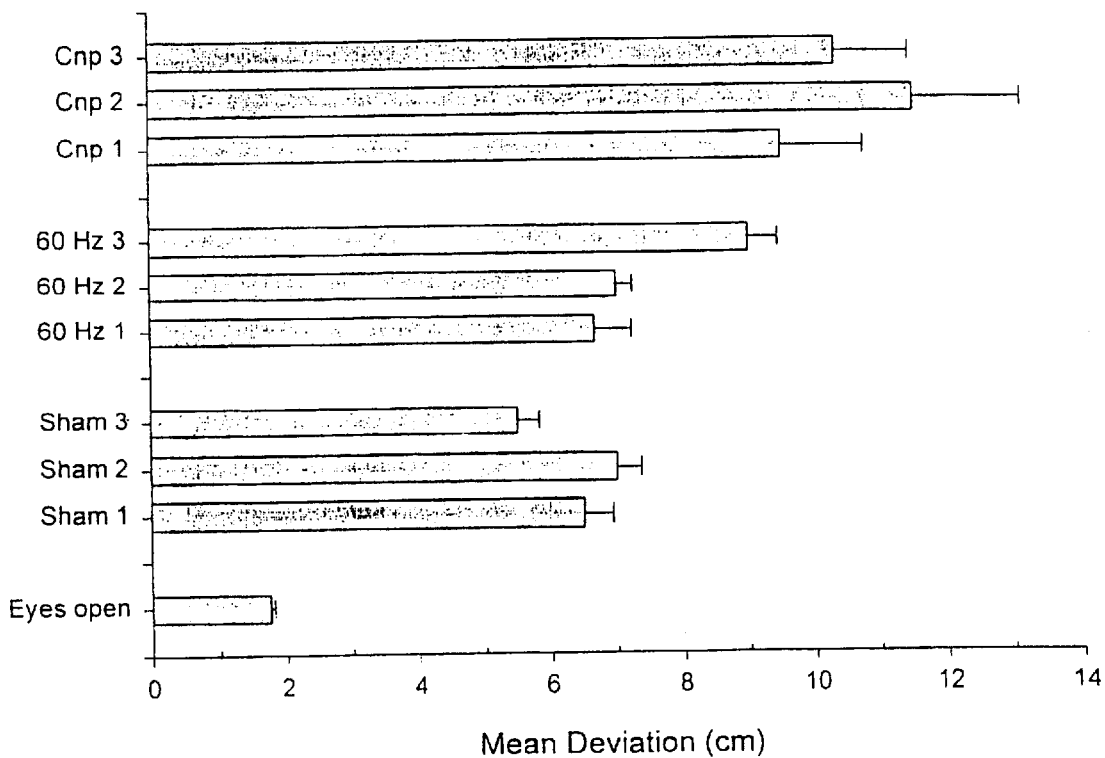

FIG. 18 shows Cnp generated interference of human standing balance. The Cnp shown in FIG. 5 was used.

Figure 19:
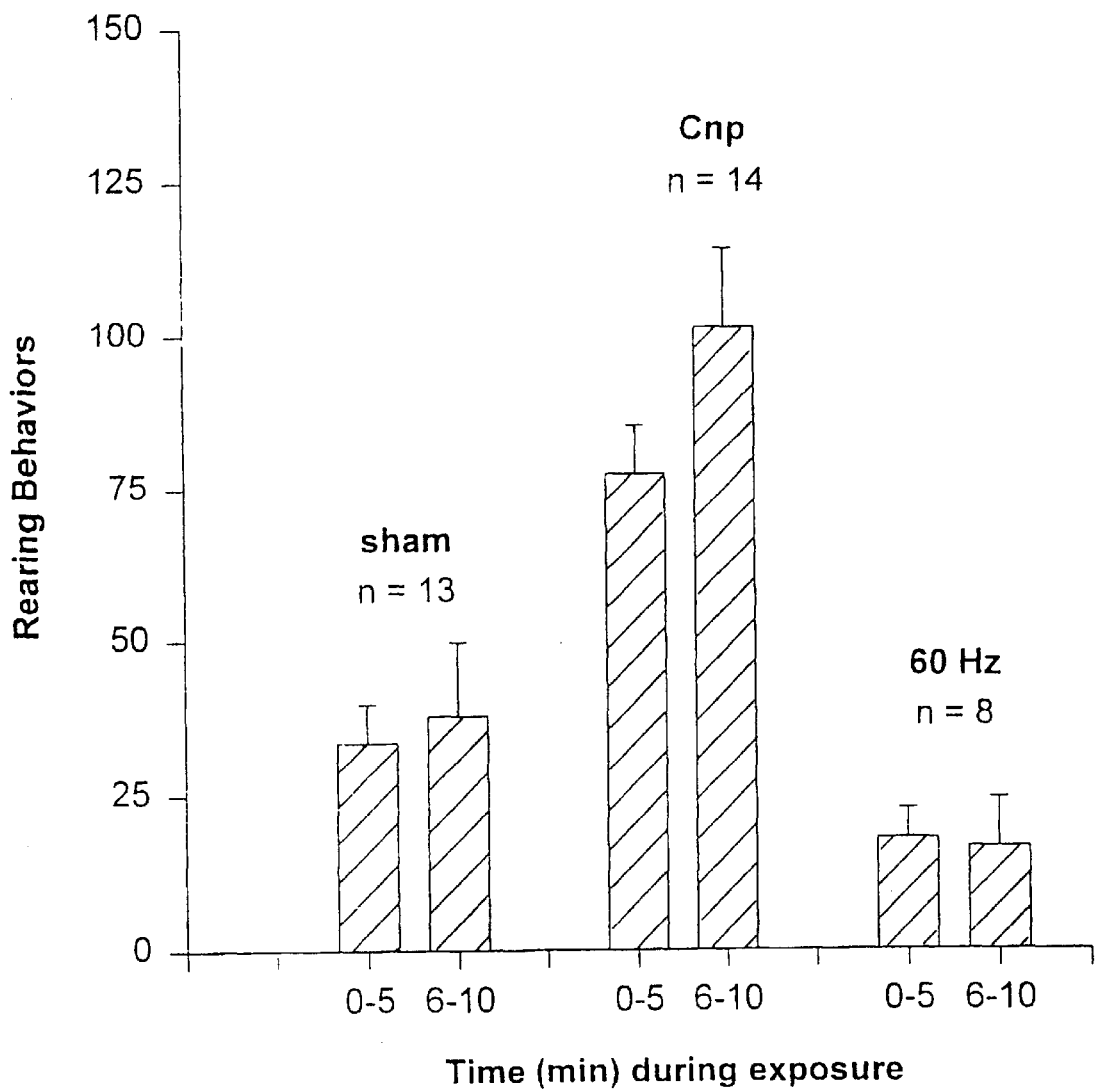

FIG. 19 shows the number of rearing behaviors in deer mice in each 5 min segment of the 10 min exposure. A rearing behavior is counted when the animal rears up on the hind limbs without touching any of the outside walls of the exposure container. The Cnp (see FIG. 3) exposure produced significantly greater counts than either the sham or 60 Hz exposure. The first (0–5) and second (6–10) minute Cnp segments are not significantly different. There are no significant differences within or between the sham and 60 Hz exposures. Error bars represent the standard error of the mean in Cnps.

Figure 20:
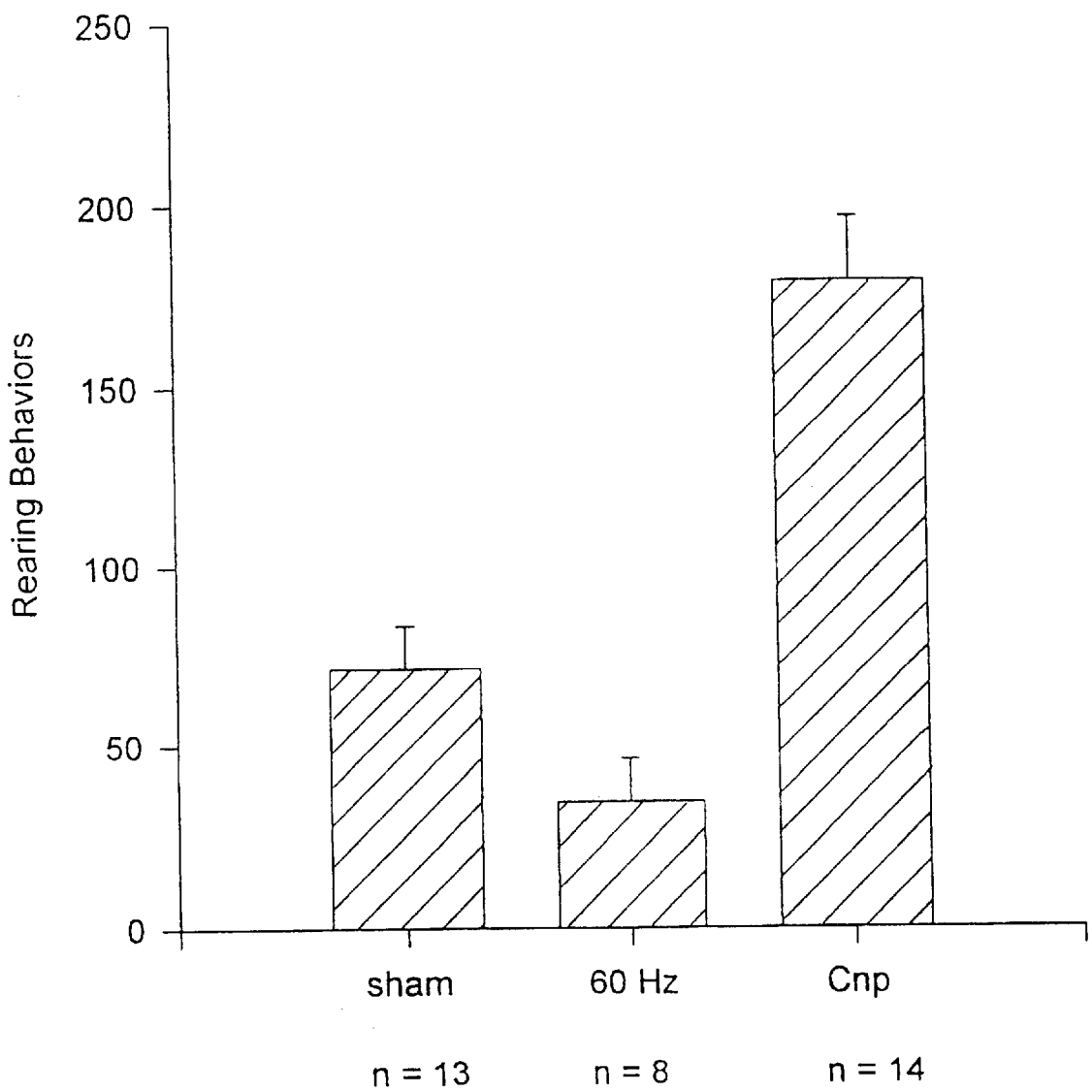

FIG. 20 shows the overall effect of Cnp (see FIG. 3) on the rearing behavior in deer mice.

Figure 21:
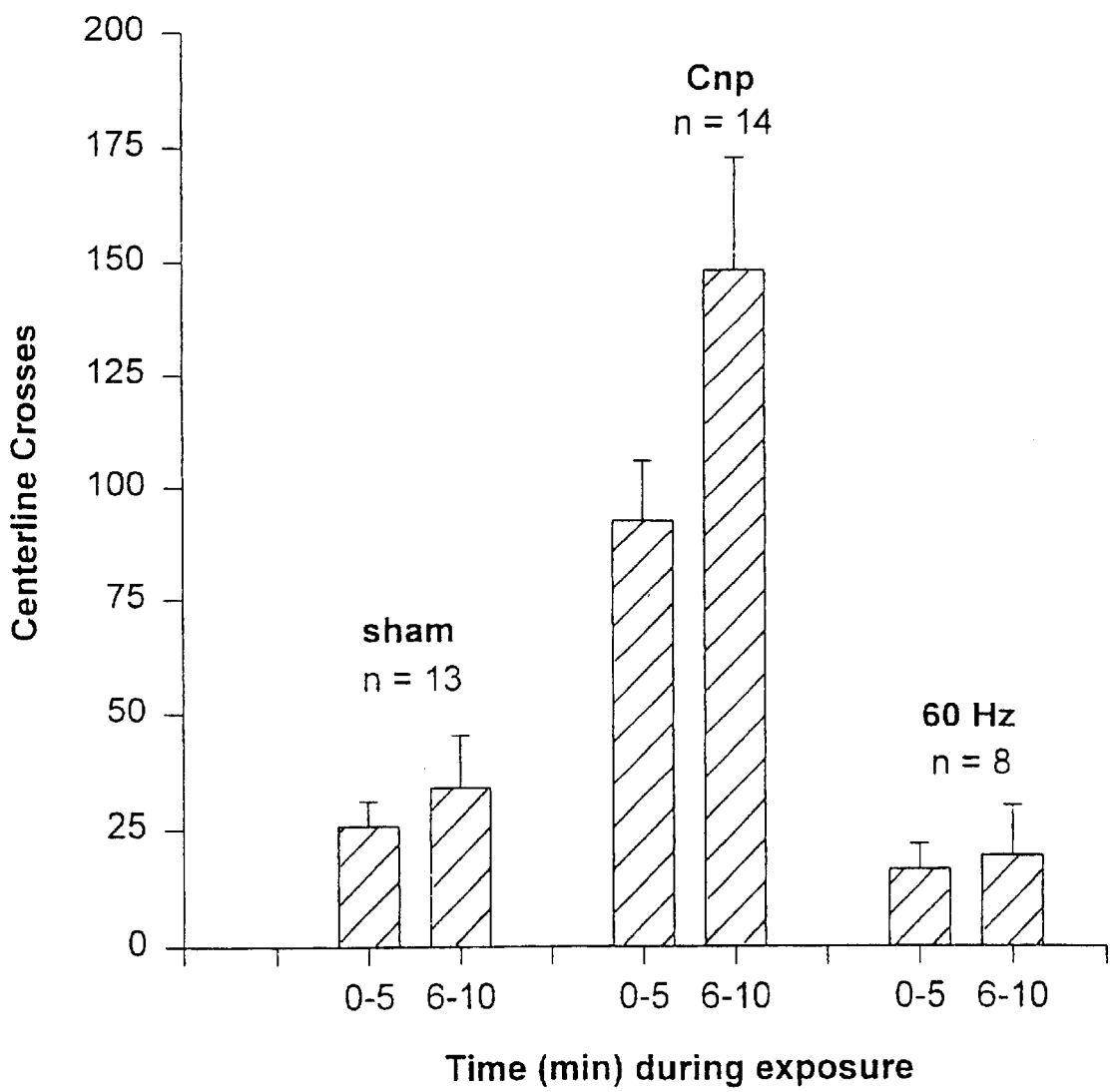

FIG. 21 shows the number of centerline crossings in each 5 min segment of the 10 min exposure. A centerline crossing is counted when the entire animal traverses across the center of the exposure container. The Cnp exposure produced significantly greater counts than either the sham or 60 Hz exposure. The first (0–5) and second (6–10) minute Cnp segments are significantly different. There are no significant differences within or between the sham and 60 Hz exposures. Error bars represent the standard error of the mean.

Figure 3:
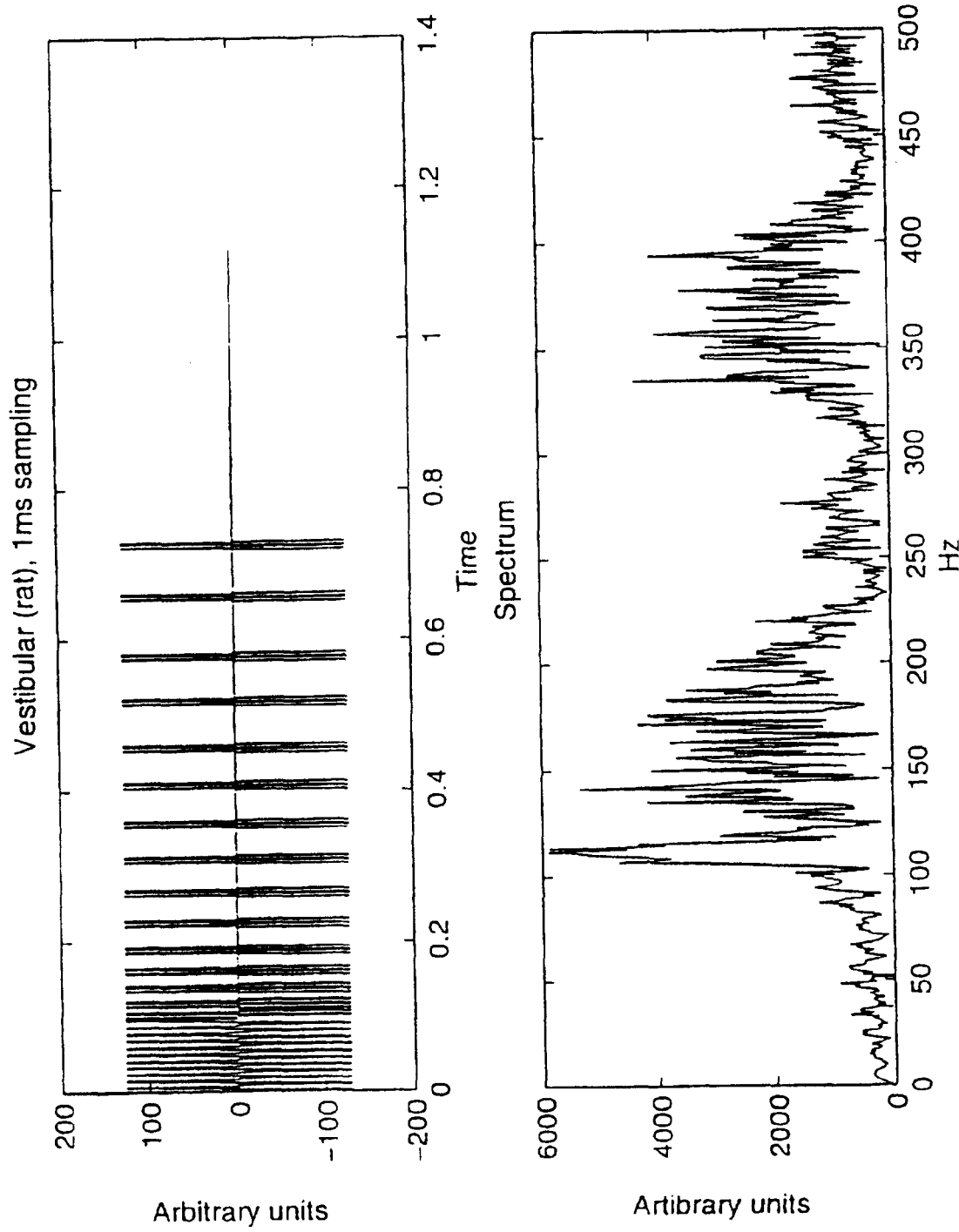
FIG. 3 shows a Cnp designed to target the vestibular system of rodents. The top panel corresponds to Cnp in time and the lower panel corresponds to the magnitude of the Fourier Transform of the Cnp.
Figure 4:
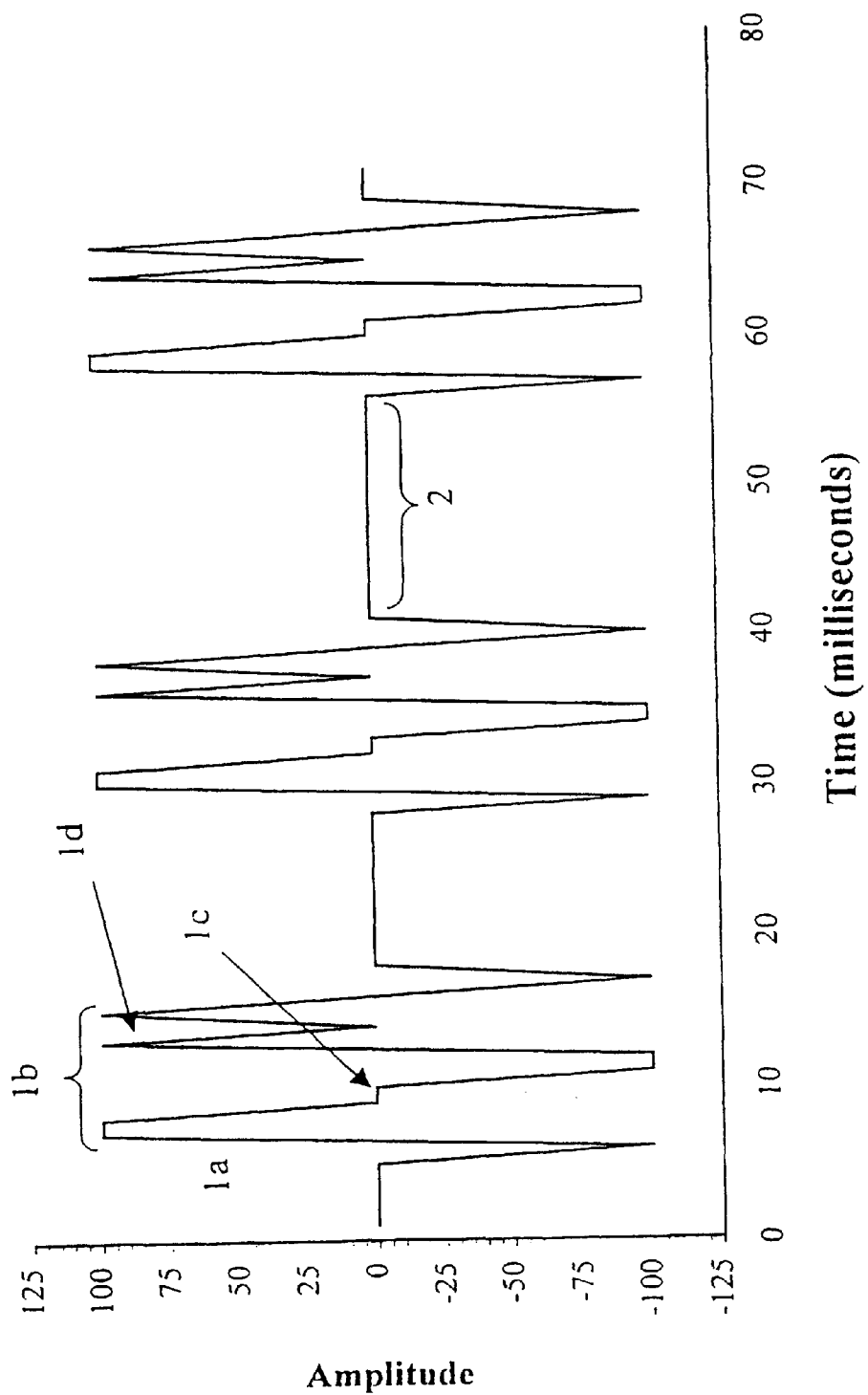
FIG. 4 shows in detail three waveforms of the vestibular Cnp shown in FIG. 3. As in FIG. 2, the x-axis indicates that portion of the time axis which has been expanded and relates FIG. 3 to FIG. 4. Sublabel 1 corresponds to the waveform and sub-label 2 to the latency period.
Figure 22:
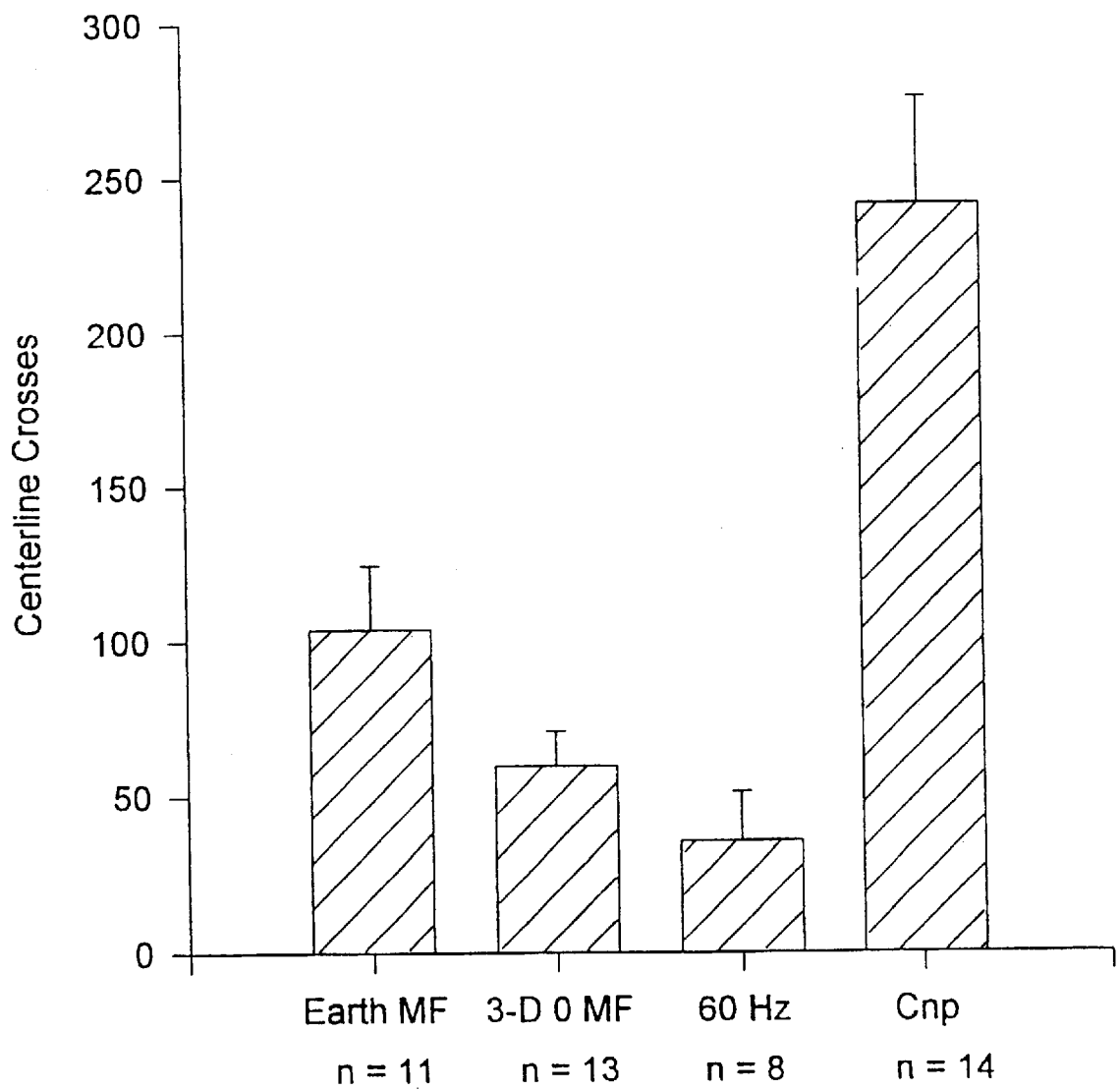

FIG. 22 shows the overall effect of the Cnp of FIG. 3 on the centerline crossing activity of deer mice.

Figure 23:
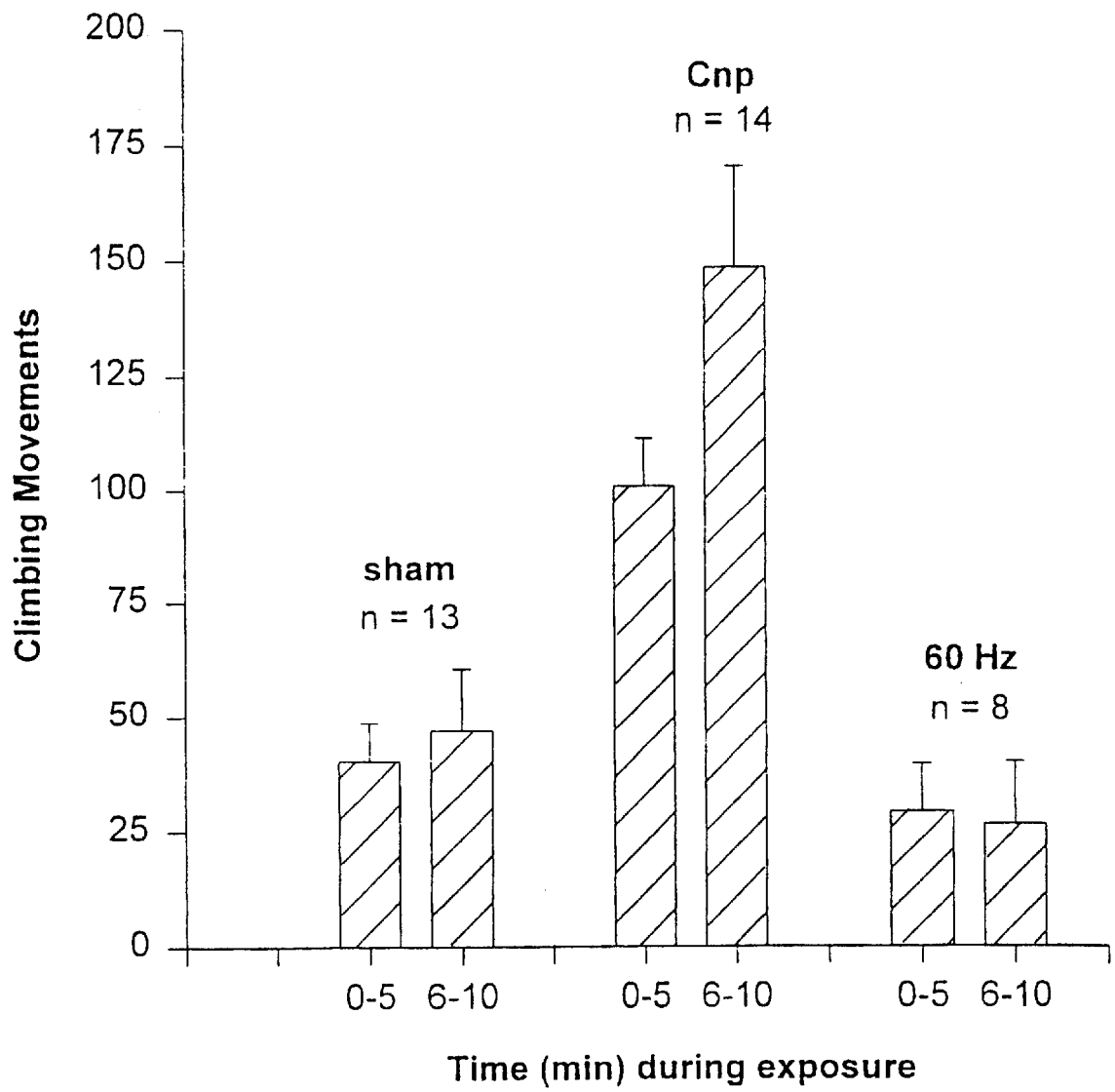

FIG. 23 shows the number of climbing movements in each 5 min segment of the 10 min exposure. A climbing movement is counted when the animal attempts to climb or reach up the side of the exposure container with 2 or more limbs extended off the floor and ends when all four limbs are on the floor. The Cnp exposure of FIG. 3 produced significantly greater counts than either the sham or 60 Hz exposure. The first (0–5) and second (6–10) minute Cnp segments are significantly different. There are no significant differences within or between the sham and 60 Hz exposures. Error bars represent the standard error of the mean.

Figure 24:
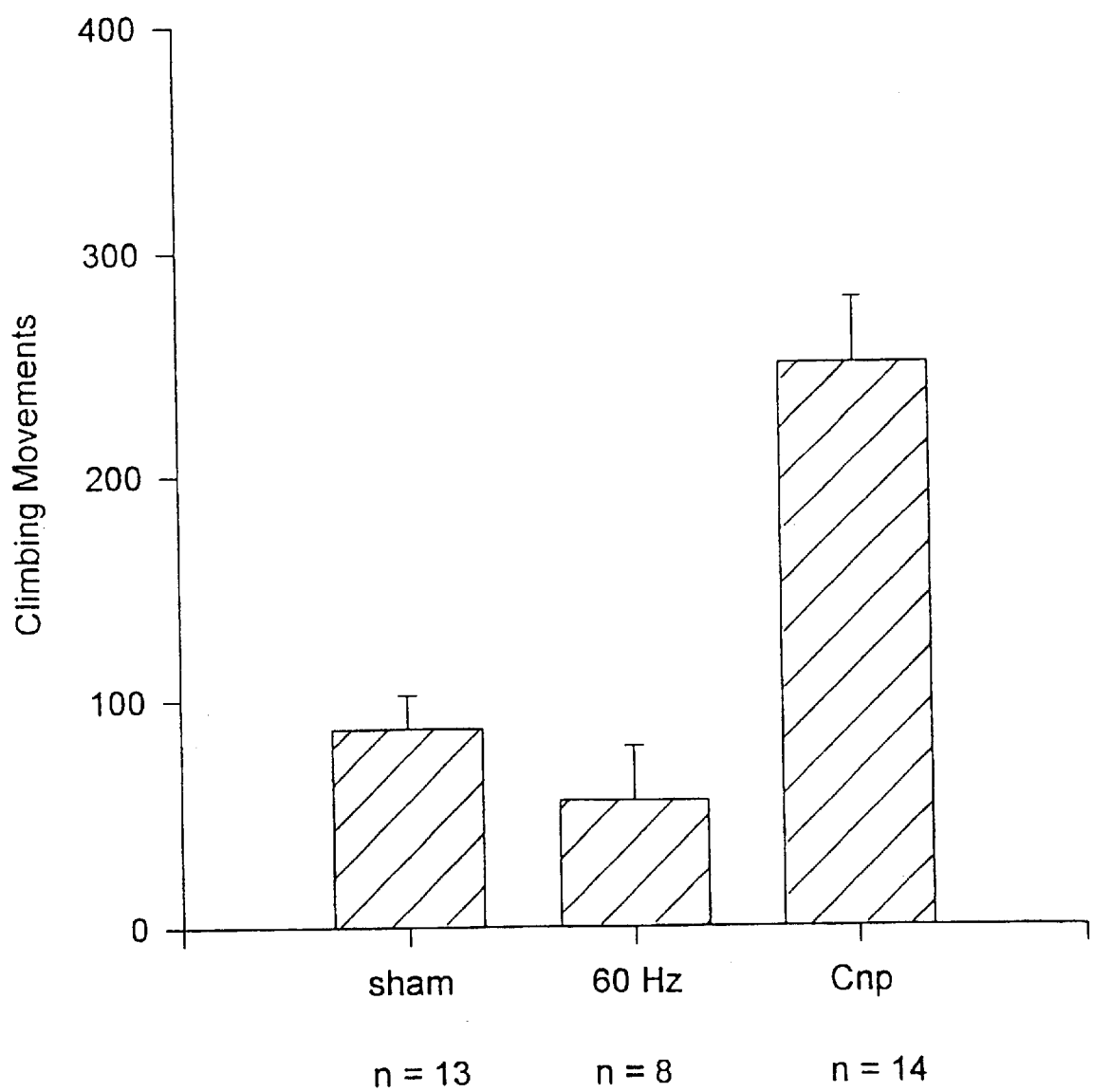

FIG. 24 shows the overall effect of the Cnp of FIG. 3 on the number of climbing movements in deer mice.

Figure 25:
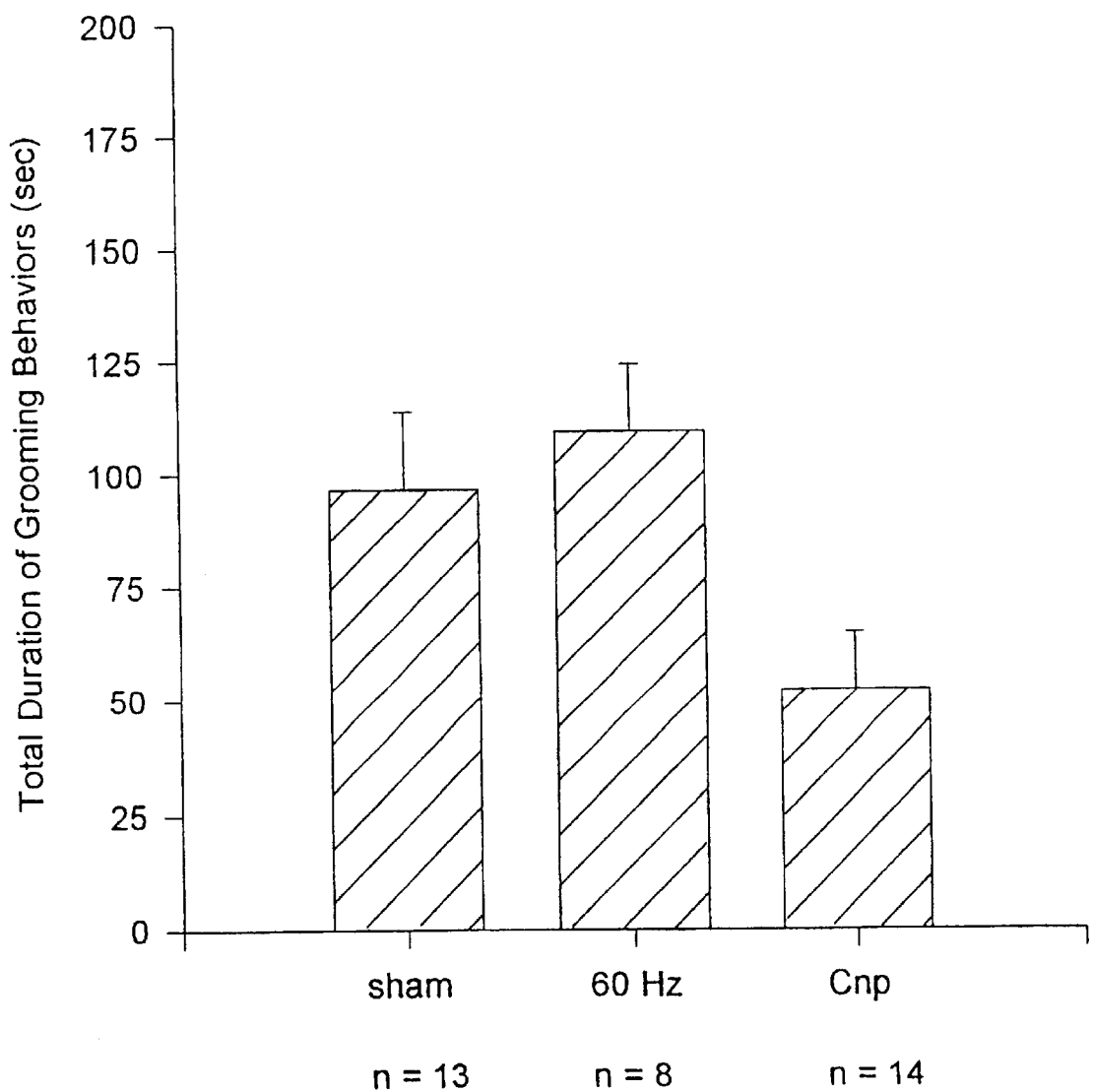

FIG. 25 shows the overall effect of the Cnp of FIG. 3 on the total duration of grooming behaviors in deer mice.

Figure 26:
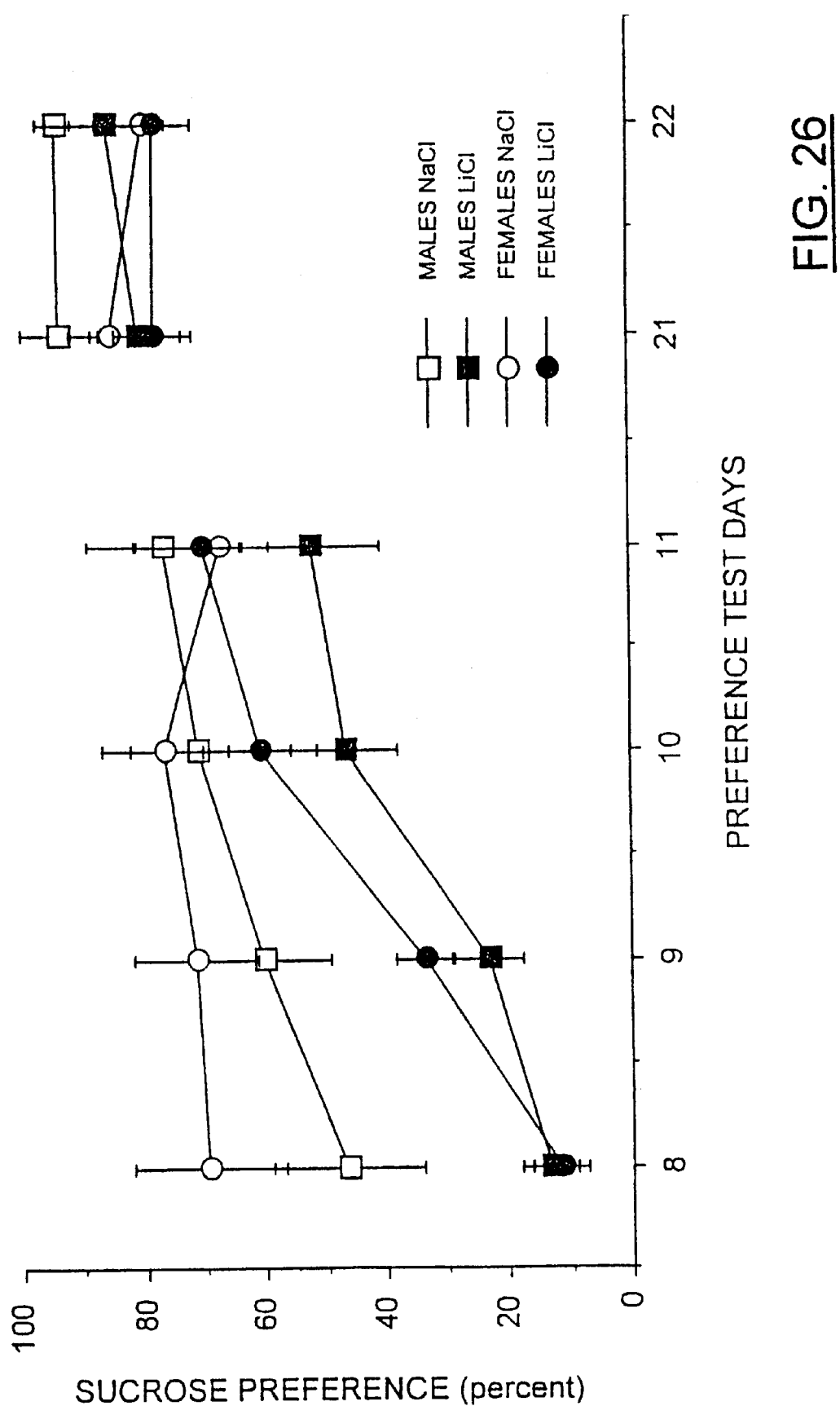

FIG. 26 shows the sucrose preference, expressed as the percent of sucrose drunk out of the total fluid intake, in male and female reproductive deer mice. Percents are referred to the day of pairing with Lithium Chloride or saline solution, the 3 days following pairing and the two re-test days (10 days after recovering from sucrose aversion).

Figure 27:
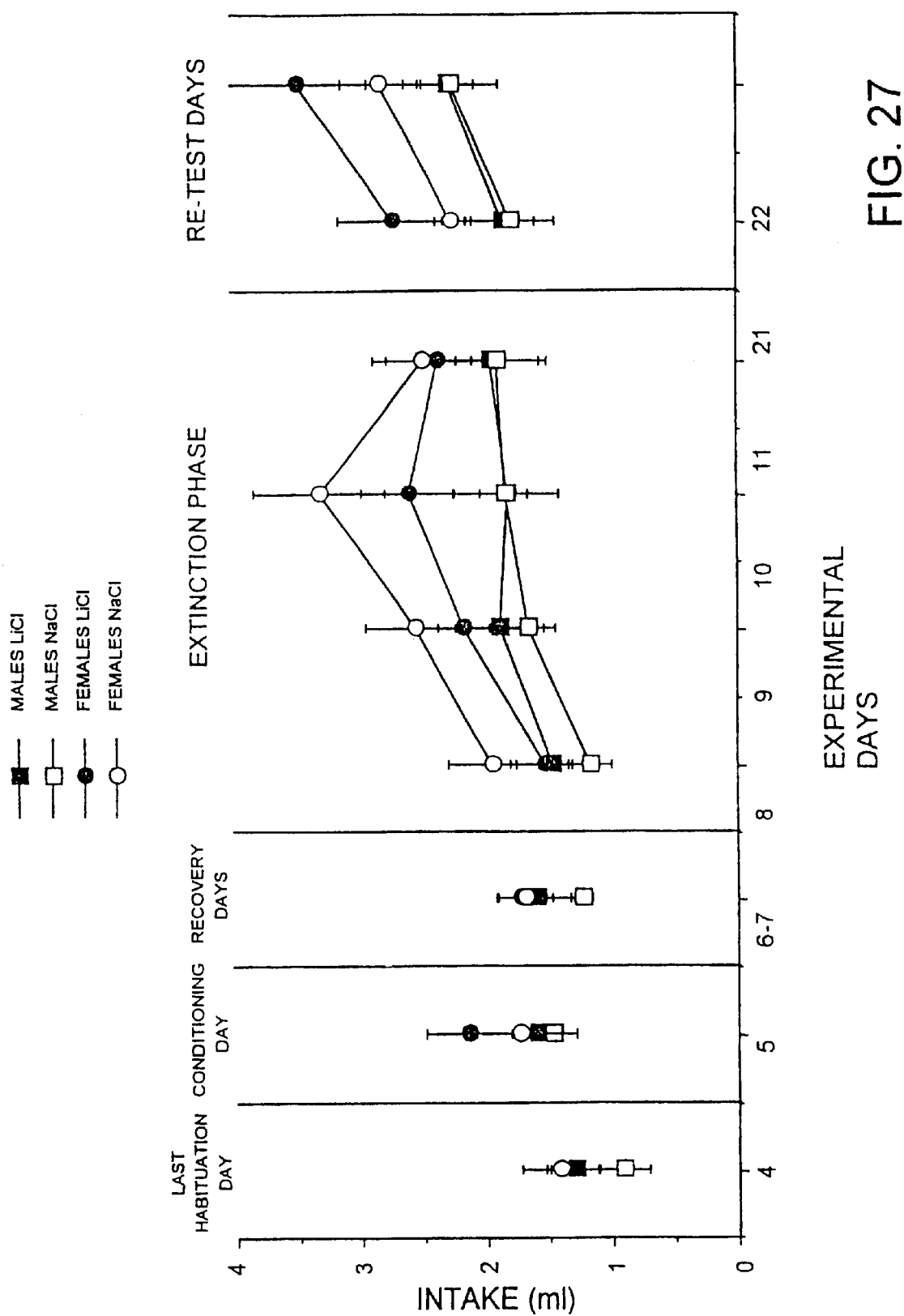

FIG. 27 shows the total fluid intake of male and female deer mice before and after treatment with Lithium Chloride or Saline Solution.

Figure 28:
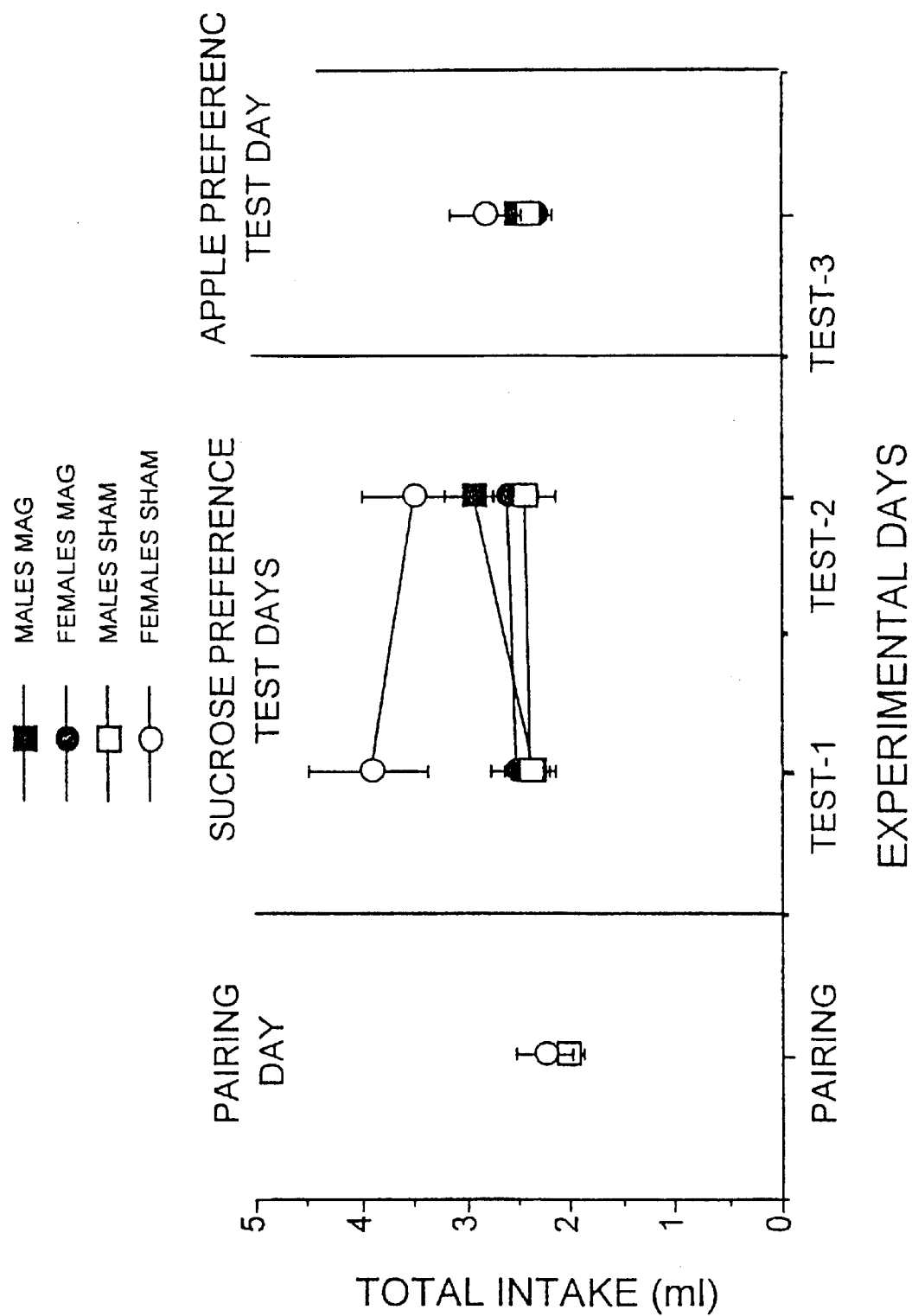

FIG. 28 shows the total fluid intake of male and female deer mice after pairing of the apple juice with a Cnp or a sham magnetic field.

Figure 29:
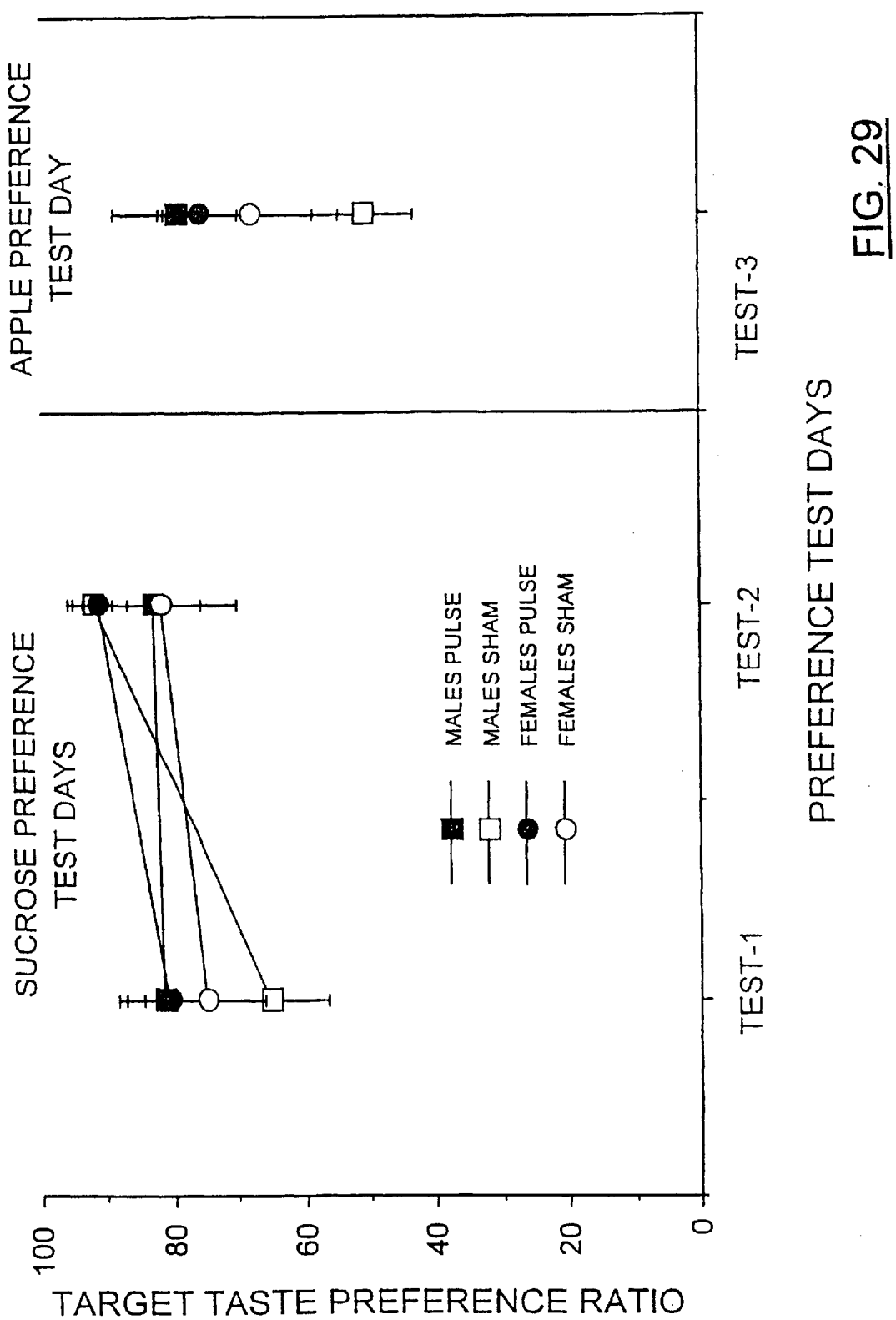

FIG. 29 shows the target taste (apple juice or sucrose) preference, expressed as the percent of target fluid drunk out of the total fluid intake, by male and female deer mice after exposure to the Cnp or a sham magnetic field.

DETAILED DESCRIPTION OF THE PREFERRED EMBODIMENTS

As hereinbefore mentioned, the present invention provides designed and characterized low frequency pulsed magnetic fields (Cnps) which have specific effects on physiological, neurological and behavioral conditions in vertebrates and invertebrates. The specific low frequency magnetic fields are designed for complex neuroelectromagnetic applications and permit the development of therapeutic strategies in order to treat and/or alter various physiological, neurological and behavioral disorders particularly in mammals and more specifically in humans.

Magnetic fields have been demonstrated to have various biological effects in humans, rodents and snails. Such magnetic fields can be detected and this detection can be broadly linked to certain physiological processes. It is now demonstrated that low frequency pulsed magnetic fields can be designed specifically to alter specific targeted physiological processes and in this manner provide a therapeutic method for treatment and alleviation of certain conditions without the need for pharmacological intervention which is expensive and which poses several problems with respect to side effects of certain drugs.

Figure 1:
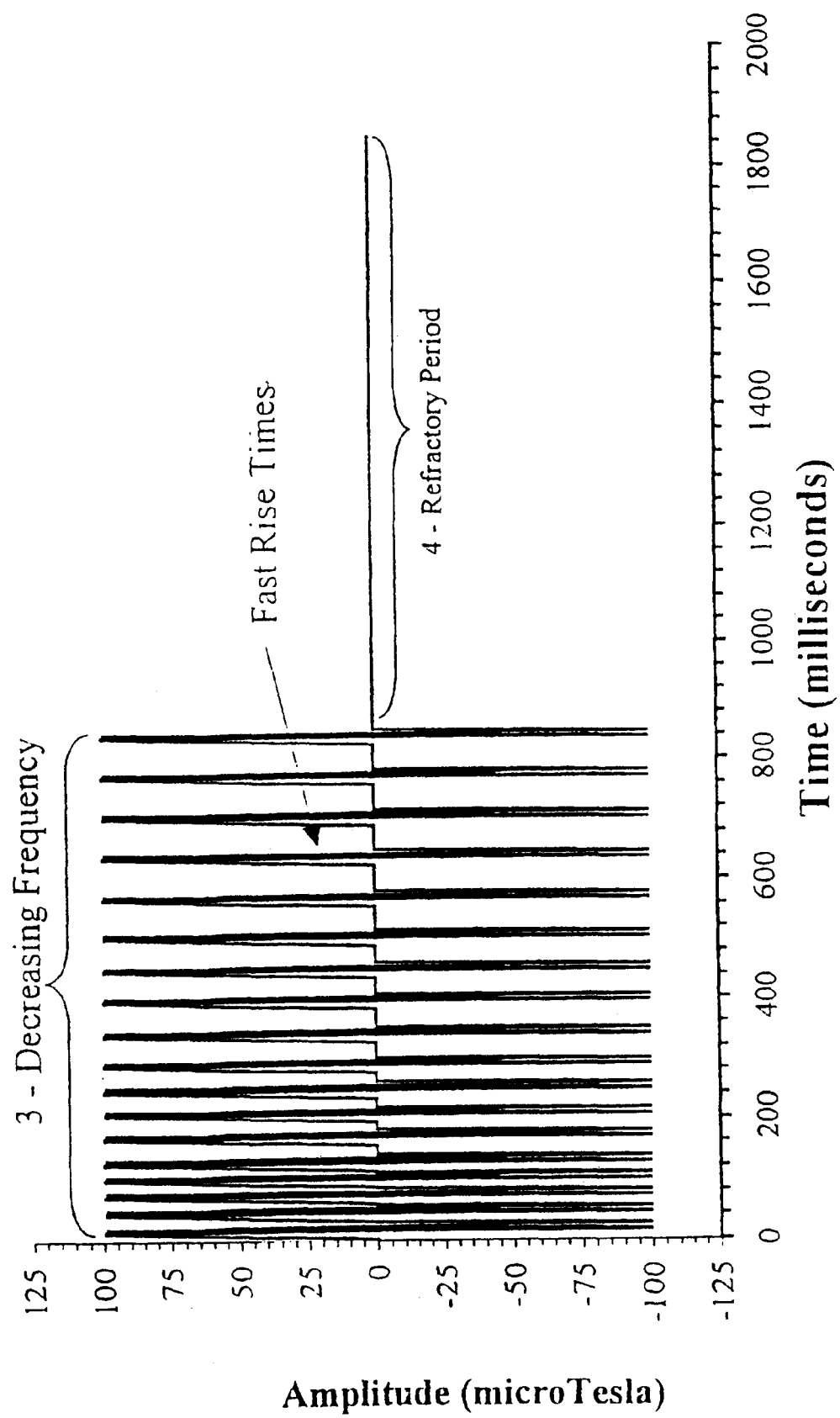
FIG. 1 shows a specific low frequency pulsed magnetic field (Cnp) used to induce analgesia.
Figure 2:
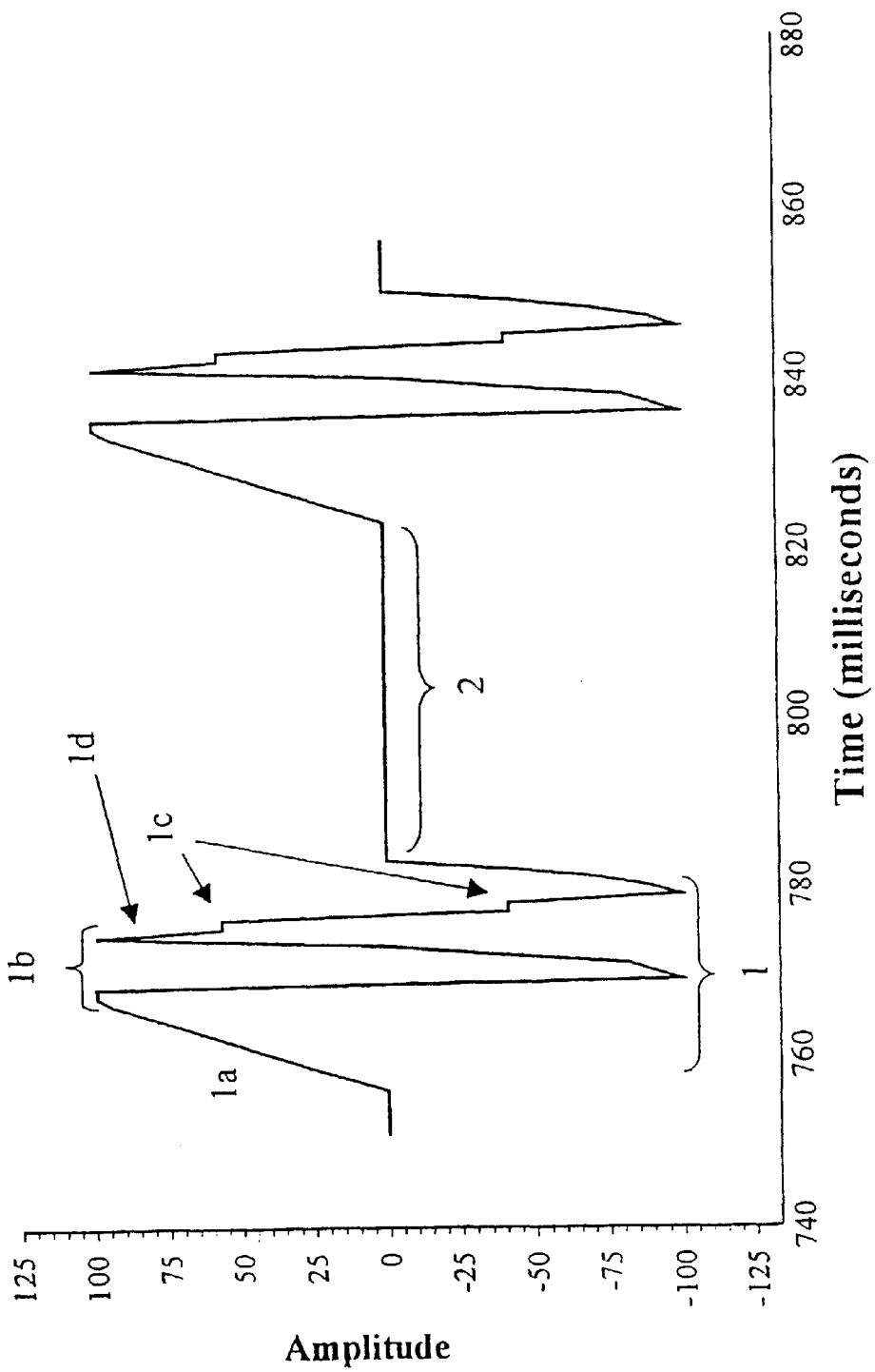
FIG. 2 shows detail of two of the waveforms of FIG. 1. Comparison of the x-axis between FIG. 1

In the present invention it is now demonstrated that the magnetic field exposure must be designed as a time varying signal such that it can be used to alter a specific targeted physiological process. The designed low frequency pulsed magnetic field (Cnp) is valid independent of the detection mechanism. However, different detection mechanisms may affect how the Cnp is scaled and how it is delivered. Under certain conditions extremely low frequency (ELF) magnetic fields can be detected directly according to a resonance model. If the tissue exposed with the Cnp pulse detects magnetic fields by the resonance model, then the amplitude of the Cnp pulse and possible DC (direct current) offsets are important and must be specified with limits below which and above which effects will lessen. On the other hand, if magnetic field detection is indirect, ie. the ELF magnetic fields are detected by tissue-induced electromotive force (i.e. Faraday's Law of Induction) then the effects will have a lower threshold below which no effect will be seen and then above this threshold effects will increase. However, even for indirect detection, a maximum threshold will exist above which the induced currents (caused by the induced EMF) will be so great that targeted effects will be swamped by large unwanted side effects. Therefore, different detection mechanisms might affect amplitude and DC offset of the Cnp, but the general design rules will not change. Individual features of a generalized Cnp are shown in FIG. 1, table 1 and FIG. 2 and are labeled in letters running from a. How these features are specified and targeted to a certain physiological/behavioral effect is described below.

Table 1 represents the 8-bit digital analog values of the specific points used in the construction of FIG. 1 (Cnp used to induce analgesia). The columns are contiguous, that is, they are essentially one long column representing all of the serial points of FIG. 1. The values presented in this table can be used by one skilled in the art to replicate the Cup used to induce analgesia using any digital to analog converter.

Design of Waveform

The low frequency pulsed magnetic fields are comprised of a plurality of intermittent waveforms. The waveform is designed to look like the corresponding electromagnetic waveform of the target tissue. For example, if the target tissue were a part, or parts, of the brain then the waveform would correspond to the energetic activity of those parts. If an electroencephalogram (EEG) could record that activity then the waveform would mimic the EEG. As seen in FIGS. 1, 2, 3 and 4 the waveform is not sinusoidal as this waveform was designed to affect critical functions that do not rely on sinusoidal waveforms. Feature $1a$ is a rise to a maximum and feature $1b$ is designed to stimulate the firing of axons in the tissue type of interest. Feature $1c$ is a built in delay to reduce the probability of neuronal excitation as the waveform ends.

Latency Period

After each waveform or between successive waveforms there is a delay, a latency period. This delay is progressively set to increase, or decrease, in length with time. This effectively modulates, in time, the frequency of appearance of the waveform. The specific lengths and progression of the Cnp waveforms are related to the target tissue. With respect to the central nervous system (CNS) for example, there are a number of characteristic frequencies which relate to: a) frequencies specific to the area of the brain; b) frequencies associated with communication/connection between different brain regions; and c) frequencies and phase offsets associated with the co-ordination of different brain regions for a specific function. Now, although the waveform has been designed to stimulate neuronal activity for a specific region, electrical activity of a region of the CNS will vary between individuals, and over time, within an individual. Therefore, to target a function the frequency of presentation of the waveform should match the frequency of the target. However, the target is varying within a frequency bandwidth. These CNS frequencies vary between approximately 7 Hz to 300 Hz. (For example: 7 Hz corresponds to alpha rhythm; 10 Hz thalamic activity; 15 Hz autonomic time; 30 Hz intralaminar thalamus and temporal regions associated with memory and consciousness; 40Hz connection between hippocampal and amygdal temporal regions; 45 Hz hippocampal endogenous frequency; 80 Hz hippocampal-thalamic communication; 300 Hz motor control.) These frequencies have upper limits due to neuronal electrical properties, that is: after a neuron "fires" it is left in a hyperpolarized state and cannot fire again until it recovers. Therefore, Feature 2 (see FIG. 2) the latency period: a) allows neurons to recover so that when the waveform is reapplied the neuron can respond; and b) its length is set so that the frequency of presentation of the waveform matches or approximates the frequencies associated with the target.

Modulation of Latency Period

To change the electrical activity of the target tissue in the CNS, the Cnp must "latch on" or more appropriately, entrain, to the appropriate frequency and either slow it down or speed it up. The waveform itself does not change substantially, rather, the frequency discussed herein corresponds to the rate at which the waveform is presented and the rate at which electrical spikes occur in the target tissue. Generally, for the CNS, as the frequency of neuronal activity is increased the amount of tissue involved per burst of activity decreases. Conversely, as the frequency is decreased a greater amount of tissue is synchronized and recruited throughout the CNS. For example, a) greater speed of cognitive processing can be associated with increased rates; b) if the rate is decreased significantly in humans or animals with epileptic-type disorders so much tissue can be recruited that seizures will occur. Therefore, the ramping up or ramping down of the rate of presentation of the waveform will: a) ensure that at least at some time the applied and endogenous rates will be matched (provided of course that the initial rate is greater than the endogenous if the purpose is to reduce the endogenous rate or lower if the purpose is to increase the endogenous rate); and b) "pull down" or "push up" the endogenous rate.

Refractory Period

As a result of the application of the Cnp the synchrony of the electrical activity of the target can be disrupted. Before the application of another Cnp can be effectual the tissue must recover its synchrony. It is allowed to do so by providing a refractory period between application of successive Cnps where the length of the refractory period is determined by the target. For example, if the Cnps are applied to a target in humans which is associated with "awareness", then the target will recover only after the awareness anticipation time is exceeded (e.g. 1200 ms). Another example would be the application for the same target, but in rodents without significant awareness, in which case the refractory period could be reduced to 400 ms. If the Cnps are to be applied for long periods of time per day, e.g. hours. then the refractory periods should be increased to 10 seconds to avoid possible immunosuppression. Immunosuppression has been show to occur when the CNS is stimulated chronically and this may be minimized if the refractory periods of this stimulation are increased to more than 7 seconds.

Variability in Features

It must be pointed out that the Cnp features are related to the underlying physiology and that endogenous frequencies vary between individuals and within an individual. Therefore, there is tolerance on the feature specifications for any Cnp designed for a specific target. For example, in the analgesia pulse shown in FIGS. 1 and 2, the features can be varied somewhat and the outcome will remain similar due to biological variations in the target. As well, as more and more is learned about biological interactions, the Cnp can be modified to take advantage of the new knowledge to make the Cnp even more specific.

Amplitude and Direction of Application

The amplitude of the Cnp to DC offset, and its direction of application (e.g. linearly polarized vs. circularly polarized vs. isotropically polarized), is dependent on the magnetic field detection mechanism which, may very well differ from one target to another. We have experimentally demonstrated that the amplitude of the Cnp can vary significantly and that the Cnp is still effective provided the features remain constant for a specific application (Thomas et al, 1997).

Specifically, if magnetic fields are directly detected there will be a window of amplitudes and the possible need of a DC offset to the Cnp for it to be effective. Further, the relative direction of the DC offset and the time-varying portion of the Cnp is important. If the detection mechanism is indirect, that is, induced currents, then an induced current feature, such as feature 1d in FIG. 1 may be added to the waveform of the Cnp. This preferably would be a feature with a high value of dB/dt with frequency components beyond those detectable by the target (i.e. for the CNS, greater than approximately 500 Hz) but designed to increase the induced EMF in the target. For magnetic fields detected indirectly, a DC offset is ineffective but direction of the applied Cnp may be important as a time changing magnetic field will induce the greatest EMF in conductive tissue which projects a maximum area normal to the direction of the Cnp. We have experimentally verified in a limited experimental trial that for some applications the effect is independent of the DC offset.

The present invention is not at the magnetic field detection level, but rather in the coupling of a specific low frequency pulsed magnetic field to the target tissue. The Cnp design philosophy is not altered if the detection mechanism is different for different targets. Rather, the Cnp is used in two "flavours", one for direct detection and the other for indirect detection. Theoretically, it may be possible to produce the Cnp waveform using other physical entities besides magnetic fields, such as flashing light, electrical fields, acoustic waves and peripheral stimulation of nerve receptors. However, extremely low frequency (ELF) magnetic fields remain the method of choice since they penetrate tissue with minimal attenuation and since their amplitude can be spatially defined largely independent of the target. Hence, they are not limited to specific targets. For example, sound is largely limited to auditory nerves, light to optic nerves and electric fields to conductive entry points such as the roof of the mouth. Also, the bandwidth of reception may be too low such as that defined by the "flicker fusion rate" of the visual system. Nevertheless, Cnps may be used in the future with other stimulation methods to increase target specificity.

Delivery-Exposure Systems

Exposure systems which produce variable magnetic field amplitude over the subject's anatomy would be preferred in situations where the endogenous frequencies and waveform of the target overlap with other tissue which could produce unwanted "side-effects". Magnetic resonance imaging (MRI) gradient tube and gradient coil technology can be easily adapted to produce such spatial variant Cnp exposures which can vary in both magnetic field amplitude and direction. Therefore, it is better to have two sets of volume coils for each of the three dimensions. One set would produce the DC offset eg. Helmholtz configuration (Prato et al, 1996) which would be needed if the detection mechanism is a resonance kind. The second would be used to define magnetic field gradients eg. Maxwell configuration (Carson and Prato, 1996)

This type of exposure system would be ideal for acute and chronic exposures in which the subject can stay in one position, e.g. treatment of pain while the subject is in bed. For mobile subjects, such volume coil configurations would not be possible and delivery would preferably be through the use of surface coils either singly, as say on the surface of the body, or around the neck or as a Helmholtz pair placed on either side of the knee. In this configuration the magnetic field amplitude decreases rapidly from the surface coil and matching of target and magnetic field without exposing other tissue to an effective Cnp becomes more challenging.

Applications of Cnps

Analgesia

The applicants have reported that complicated pulsed magnetic fields (Cnps) have a pain inhibitory (analgesic) effect. In one embodiment of the present invention, the designed Cnps can both increase the analgesic effect of an injection of an opiate, eg. Morphine, or actually induce a level of analgesia similar to a moderate dose of morphine. This has a tremendous benefit for the potential of drug-free pain treatment which is highly desirable.

Opioid receptors are responsible, among many other functions, for the mediation of pain. Increase in exogenous/endogenous opioids can induce analgesia The applicants have shown that single sinusoidal ELF magnetic fields can attenuate opioid induced analgesia. The applicants have recently demonstrated that the detection mechanism responsible for this response to ELF magnetic fields is a resonance model, that is, direct detection (Prato et al, 1996).

Figure 6:
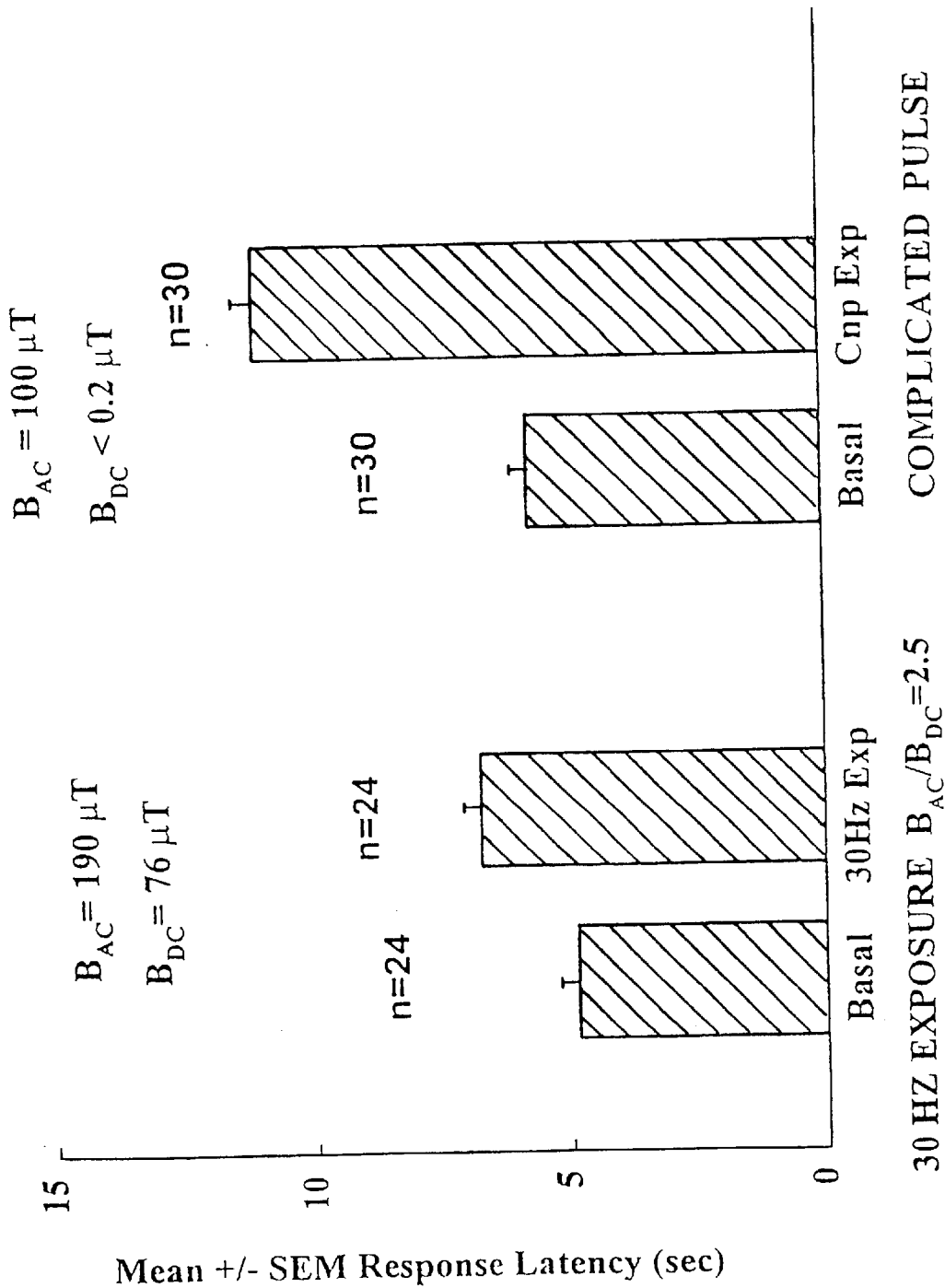
FIG. 6 shows the effect of a Cnp targeted to induce analgesia in a land snail. The y-axis corresponds to a measure of analgesia. Basal corresponds to measurements done prior to exposure. The induction of analgesia is only thirty percent when a simple magnetic field waveform is applied (30 Hz sinusoidal 15 minute continuous exposure with a peak amplitude of 190 μT and a static field of 76 μT parallel to the 30 Hz field). However when a specific designed magnetic field pulse (Cnp Exp) is given the analgesia is increased by more than 100 percent from the Basal value.

Since increases in opioid induced analgesia, rather than decreases, would have therapeutic value, and since induction of analgesia by ELF magnetic fields would have even greater value the applicants have developed a simple pure sinusoidal waveform specification that would induce mild analgesia. As shown in FIG. 6 the increase was modest (20–30%). However, when the applicants designed a Cnp to induce analgesia the effect was made much larger (FIG. 6).

Figure 7:
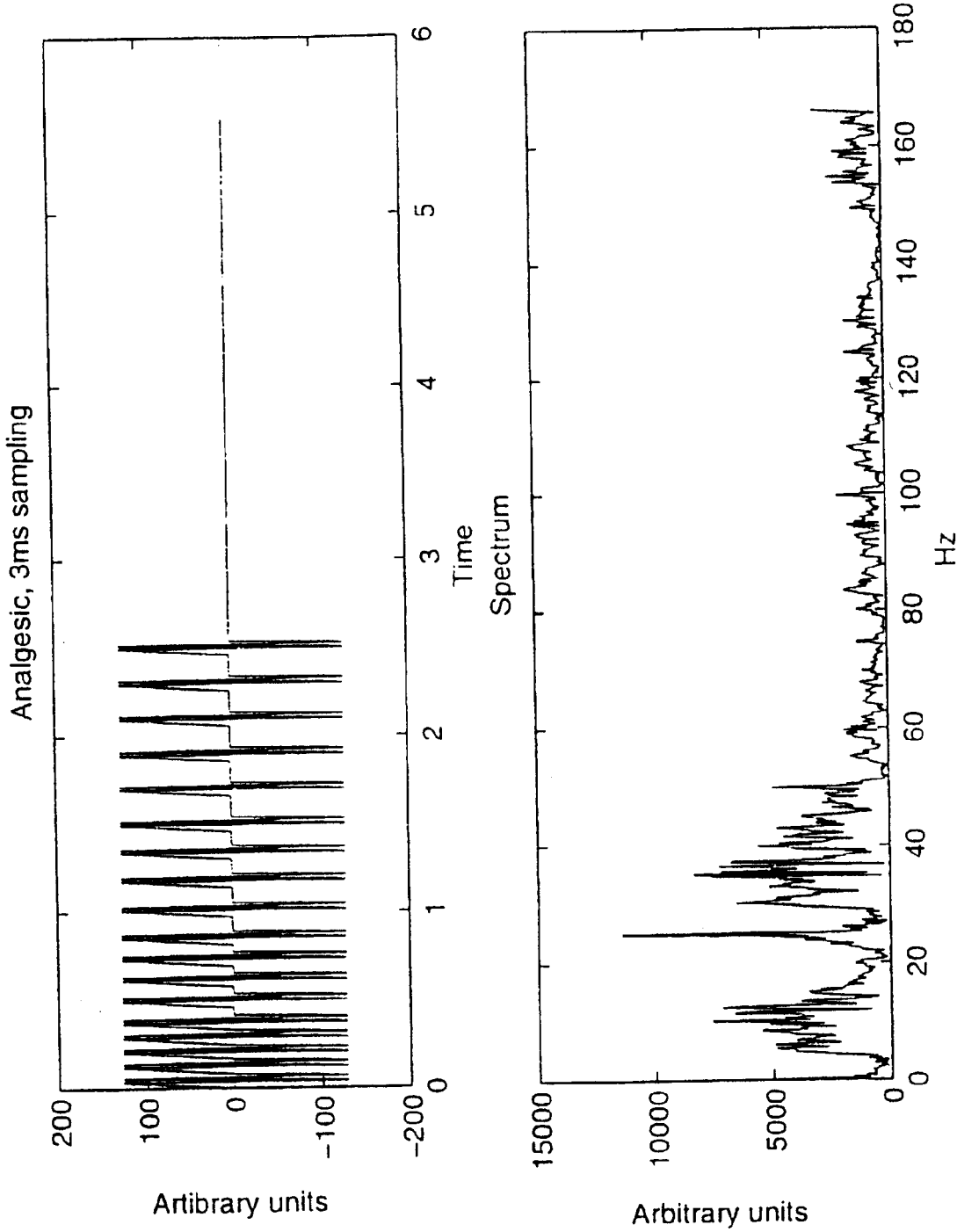
FIG. 7 shows a Cnp pulse designed to target central nervous system targets which should increase analgesia in land snails. The upper panel corresponds to Cnp in time and the lower panel to the magnitude of the Fourier Transform of the Cnp.

The analgesia Cnp used and its magnitude Fast Fourier Transform are shown in FIG. 7. This in fact is the Cnp shown as FIGS. 1 and 2. This "analgesic pulse" can be used to: a) increase opioid induced analgesia; and b) significantly induce analgesia. In addition, it is now known that analgesia is only partially opioid mediated and that another analgesic component is present. This additional component corresponds to the modulation of another target tissue or system, as yet unidentified. This is probably due to the more general nature of this Cnp, and that the entire animal was exposed to identical magnetic fields. The power in the frequency was in three bands: 4–16 Hz; 22–26 Hz; and 28–52 Hz. The whole body of the animals (land snail, *Cepaea nemoralis*) were exposed and the purpose was to slow down activity in the brain structures which have a high concentration of opioid receptors and are responsible for the awareness of pain with frequencies in the range of 28-52Hz. Note, that when a random pulse was used, in which frequency analysis indicated constant power in all frequencies between 0–166Hz, the induction of analgesia was not seen, indicating the specificity of even this general Cnp. The slowing up and disruption of function in such biological sites in the snail equivalent to the CNS should have profound effects beyond the induction of analgesia. In fact when whole rats with a pre-existing condition of status epilepticus were exposed to this waveform, the result was increased seizure activity. As previously discussed, when frequencies of waveform firings are reduced, more tissue is recruited. In this extreme case, sufficient CNS tissue was recruited in the electrically labile rat exposed to this Cnp resulting in increased seizure activity.

This Cnp pulse can be made more specific by treating subjects, like humans, only over specific CNS structures or by incorporating more selectively designed waveforms.

Figure 8:
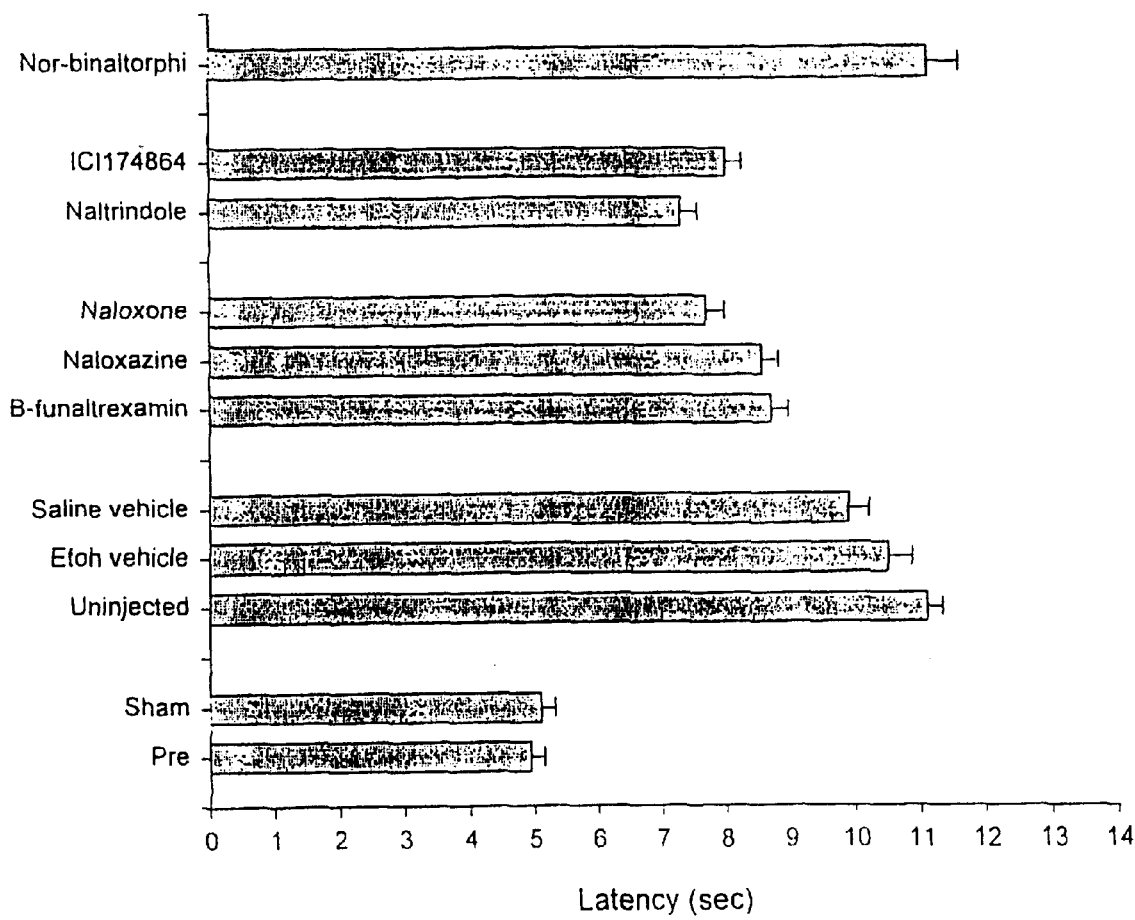
FIG. 8 shows that opioid antagonists reduce, but do not block, Cnp induced analgesia.

The applicant's have previously demonstrated that a short acute exposure to a specific weak extremely low frequency pulsed magnetic field (Cnp) can induce significant partly opioid-mediated analgesia in the land snail, *Cepaea nemoralis*. In the first studies individual groups of snails, *Cepaea nemoralis*, were pre-injected with either the general opioid antagonist naloxone or specific antagonists ($\mu$naloxazine, $\beta$-funaltrexamine, $\delta$ naltrindole, ICI-174, 864 or ic nor-binaltorphimine opioid peptide specific antagonists), their respective injection vehicles or received no injection and then were exposed for 15 minutes to a Cnp or a sham condition. The snails were then tested for response latency on a hotplate (40° C.). There were no significant differences in pre-exposure response latencies, or in sham exposure response latencies, and hence, the individual groups were combined as seen in FIG. 8. All groups showed a significant degree of induced analgesia as inferred by an increase in response latency; however, the general p and 8 opioid antagonists significantly reduced, but did not block, the Cnp induced analgesia.

Figure 10:
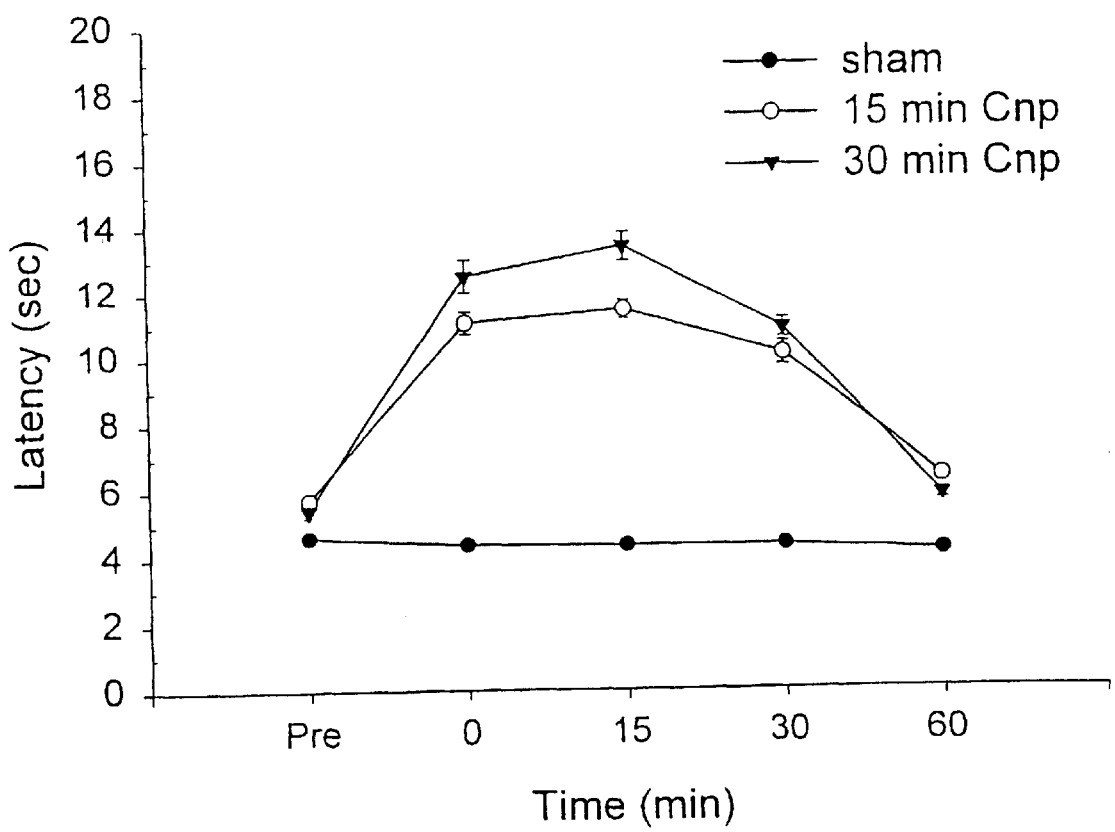
FIG. 10 shows the effects of an acute 15 or 30 min exposure to either a specific pulsed magnetic field (Cnp) or sham exposure condition on the thermal (40° C.) response latencies of individual hydrated snails (N=120). Response latencies were recorded prior to (Pre) and after exposure. Sham 15 and 30 min exposures were not significantly different and were combined. Error bars represent the Standard Error of the Mean (SEM), and where not visible are embedded within the symbol.
Figure 11A:
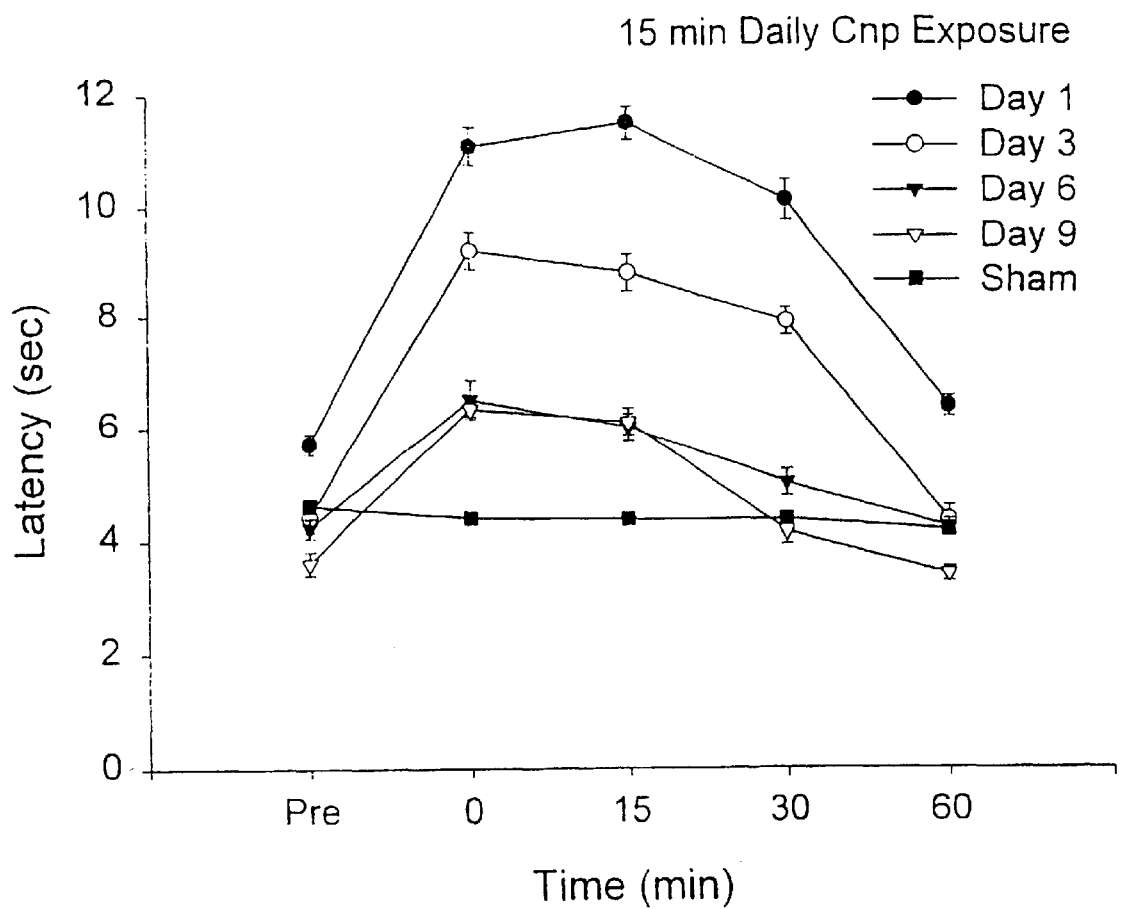
FIG. 11 shows the effects of either (A) 15 min or (B) 30 min daily repeated exposures to either a specific pulsed magnetic field (Cnp) or sham exposure condition on the thermal (40° C.) response latencies of individual hydrated snails (N=60).
Figure 11B:
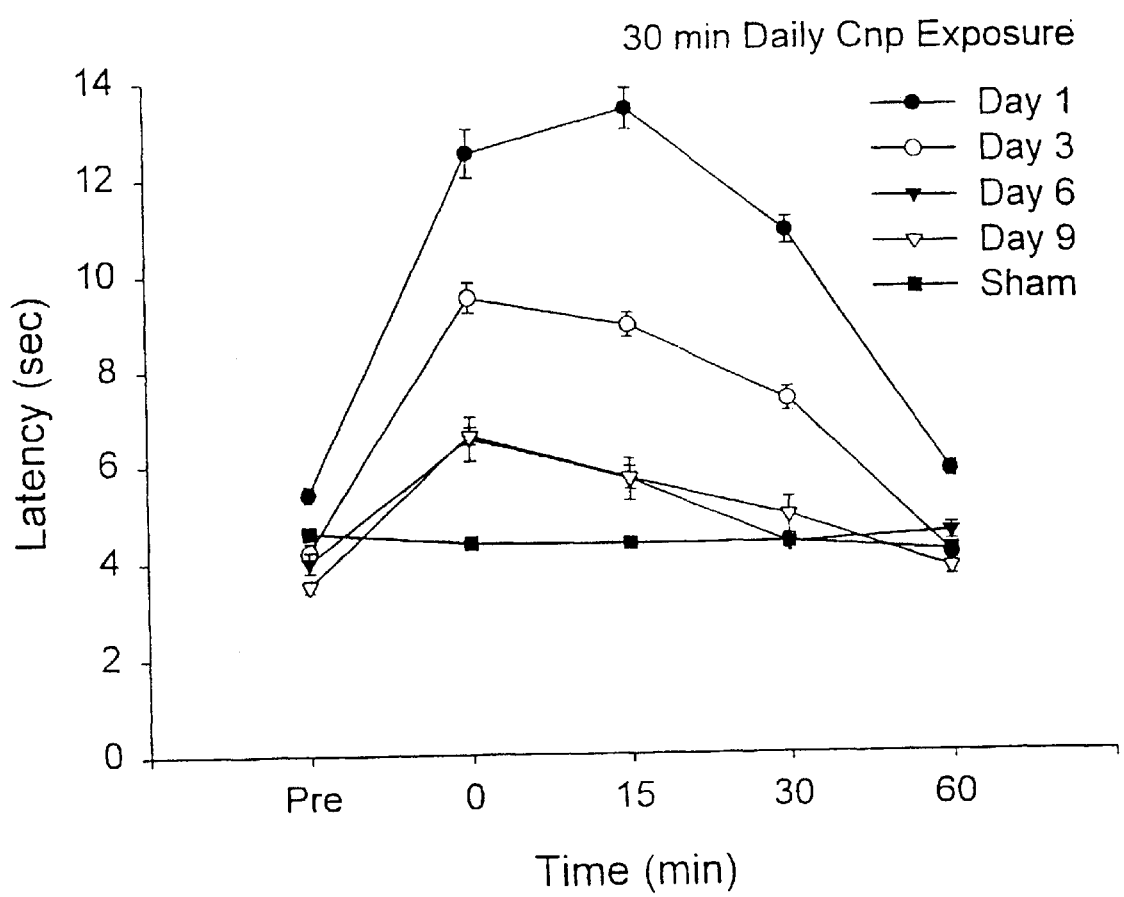

The time course of Cnp induced analgesia in these snails was also initially investigated. Individual groups of snails were exposed to Cnps for either 15 or 30 minutes and then tested immediately, at 15, 30 and 60 minutes after the Cnp exposure for response latency on a hotplate (40° C.). While there was no significant difference between the 15 and 30 minute exposures, as compared to the sham exposure, there was a significant degree of induced analgesia up to and including 60 minute post exposure (FIG. 10).

The effect of Cnp induced analgesia has now been examined for the development of tolerance to daily repeated acute exposures of 15 or 30 minute duration. Also examined was the effect of acute cross-tolerance to the d opioid receptor directed against the DPDPE enkephalin. The results of this study show that brief (15 or 30 min) exposure to a specific pulsed magnetic field (Cnp) has antinociceptive or "analgesic" effects in the land snail *Cepaea nemoralis*. The magnitude and duration of this Cnp induced analgesia was reduced, though not blocked, following repeated daily exposures, in a manner indicative of the partial development of tolerance. Both associative (learning related) and non-associative (pharmacological related) processes were suggested to be linked with the expression and reduction of the analgesic effect of this specific pulsed magnetic field (Cnp) following repeated exposures. Presentation of novel environmental cues could ameliorate the expression of this tolerance and nearly re-instate the level of acute Cnp exposure induced analgesia. These results are consistent with, and extend, prior findings of specific pulsed magnetic fields, including the Cnp, having behavioral actions in invertebrate and vertebrate systems. These results also substantiate and extend prior reports that the effects of ELF magnetic fields on analgesia and likely other behavioral and physiological responses can be modified with repeated brief daily exposures.

Exposure for either 15 or 30 min to the Cnp resulted in a significant increase in the latency of response of Cepaea to an aversive thermal surface, indicative of the induction of analgesia. The magnitude of this analgesia was related to the length of exposure suggesting a possible duration or dose-related effect of the Cnp. In previous studies it was shown that the Cnp induced analgesia is not a generalized or stress-related effect of exposure to magnetic fields. Other similar designs of pulsed magnetic fields were shown to have no significant effects on either basal nociceptive sensitivity or opioid-induced analgesia [Thomas et al., 1997]. In addition, simple sinusoidal extremely low frequency magnetic fields (<300 Hz) have been shown either to attenuate or weakly augment opioid-mediated analgesia depending on the specific magnetic field exposure characteristics. In the present, as well as prior studies, repeated sham exposures (zeroed or normal Earth magnetic field) and repeated determinations of response latencies, had no significant effects on nociceptive sensitivity.

The significantly greater magnitude of analgesia induced by the 30 exposure to the Cnp as compared to the 15 minute exposure is consistent with the findings that the inhibitory effects of an acute magnetic field exposure on opiate analgesia are affected by both the duration of exposure and the intensity of the magnetic field. Results of more in depth investigations, however, have also shown that the magnitude of the inhibitory effects does not scale linearly with either the frequency or amplitude of the ELF magnetic field [Prato et al., 1995].

Substantial evidence exists for the presence of multiple endogenous opioid inhibitory systems. Both naloxone-reversible 'opioid' and natoxone-insensitive 'non-opioid' forms of analgesia have been indicated [Rothman 1996] and are apparently phylogenetically conserved and expressed in both rodents and Cepaea [Kavaliers et al., 1983]. In prior investigations with Cepaea, it was established that the Cnp induced analgesia was of a mixed opioid and non-opioid nature [Thomas et al., 1997; Thomas et al., 1997(in press)]. The analgesic effects of the Cnp were reduced, but not blocked, by the prototypic opiate antagonist, naloxone, and the d opioid receptor directed antagonists, ICI 174,842 or naltrindole-5'-isothiocyanate (5'-NTII) (Table 2 and Thomas et al., 1997 (in press)). However, the analgesic responses were unaffected by pretreatment with the kappa opioid directed receptor antagonist, norbinaltorphimine. This lack of a complete blockade of the Cnp induced analgesia by the opioid antagonists indicates that "non-opioid" as well as opioid mediated mechanisms are associated with the effects of the Cnp. The neurochemical mechanisms mediating this non-opioid analgesia remain to be determined.

Typically chronic repeated administrations of opiates result in the development of tolerance, such that the analgesic effects initially produced by substance such as morphine show a progressive decline in intensity until they are indistinguishable from the responses of control animals. Similar patterns and characteristics of morphine tolerance have been established to occur in Cepaea and rodents [Kavaliers et al., 1983; Kavaliers et al., 1985]. Here, it was determined that after 6–9 days of daily 15 or 30 min exposures to the Cnp, tolerance developed to the opioid mediated component of the induced analgesia. The pattern of response and time course is similar to that for the development of tolerance to antinociceptive effects of opioid peptides and opiate agonists in Cepaea and rodents. The level of analgesia attained after 6–9 days of daily exposure to the Cnp was similar to that recorded in snails treated with either naloxone or specific δ opioid receptor directed antagonists and followed by a single Cnp exposure. In addition, the snails that had received the daily exposures to the Cnp displayed a significantly reduced sensitivity to the analgesic effects of the specific 5 opioid agonist. DPDPE. This is suggestive of at least a partial generalization of tolerance (i.e. cross-tolerance) to the opioid component of the Cnp. Determinations of the nociceptive responses of snails that have become tolerant to DPDPE and are subsequently exposed to the Cnp are necessary to explore more fully the extent of this generalization and the expression of cross-tolerance between Cnp and δ opioids.

In the present experiments there was little evidence of a reduction in the level of the "non-opioid" mediated analgesia induced by repeated exposures to the Cnp. The analgesia induced by the 15 min and 30 min Cnp exposures was reduced to a similar level. This raises the intriguing possibility that increased duration of the Cnp may selectively augment the opioid mediated analgesia while leaving a relatively constant basal non-opioid mediated component. It also suggests that various components of this specific Cnp may differentially affect the expression and neurochemical substrates of opioid and non-opioid analgesia.

There have been only limited considerations of the development of tolerance to naloxone-insensitive non-opioid analgesia. These studies have revealed either relatively low or no development of tolerance to non-opioid analgesia This is not, however, completely limited to non-opioid analgesia, as weak tolerance has also been reported to the antinociceptive effects of certain opioid activating factors in rodents. There is also no apparent cross-tolerance between opioid and non-opioid analgesia, with it having been speculated that the presence of opioid analgesia may even preclude the development of tolerance to non-opioid analgesia [Rothman 1996]. Similarly, it is possible that the presence of non opioid analgesia may affect the expression of opioid systems and limit the expression of complete cross-tolerance as suggested here with DPDPE (FIG. 16).

It should also be noted that tolerance is considered to be best demonstrated by a shift in the dose-response indicative of the need for a higher dose to produce a consistent drug effect. In the present study, tolerance is inferred from the decrease in analgesia produced by daily repeated 15 or 30 min exposures to the Cnp. The lack of supporting evidence for a definitive linear dose-dependent effect of Cnp, along with the similar reductions in analgesic effects of the 15 and 30 min Cnp exposures, precludes examination of shifts in dose responses.

Opiate tolerance has been proposed to involve both associative and non-associative components. In prior investigations it was shown that after the termination of drug treatment, Cepaea that were rendered fully tolerant to morphine exhibited dependence and withdrawal symptoms, including hyperalgesia, that are considered to be consistent with non-associative mechanisms [Tiffany et al., 1988].

Non-associative tolerance is considered to represent an effect arising solely from drug exposure. Tolerance is considered to result in part simply from cellular adaptations produced by repeated drug stimulation of some physiological system such as a particular receptor or second messenger cascade.

Opioids have stimulatory as well as the more conventionally studied inhibitory effects on neurotransmission that are accepted as the mechanisms underlying analgesia. There is accumulating evidence that these stimulatory effects may also be associated with the development of opioid tolerance. In this regard, daily acute exposures of Cepaea to ELF 60 Hz magnetic fields were shown to result in hypoalgesic or analgesic effects consistent with the antagonism of the excitatory hyperalgesic effects of endogenous opioids.

There is also evidence that particular transmitter systems may function to counteract opioid effects and mediate some aspects of tolerance. In this view, tolerance may not only result from decreased opiate efficacy, but also enhanced "anti-opiate" influences. The putative anti-opioid peptide, orphanin FQ or nociceptin, which exerts its effects through a novel oiphan, opioid-like receptor, and has been recently implicated in tolerance, has been shown to affect nociceptive responses in Cepaea through NMDA associated mechanisms. Intriguingly, orphanin FQ has also been recently suggested to be involved in opioid mediated electro-acupuncture-induced analgesia [Tian et al., 1997].

Tolerance has also been shown to involve associative learning. Animals, including Cepaea, repeatedly receiving morphine in a consistent, distinctive environment are much more tolerant to the analgesic and thermic effects of morphine than when tested in a different, novel, environment. In the present study this "environmental specificity" was demonstrated for the opioid mediated analgesic effects of the Cnp. Snails that were exposed to the Cnp while in a novel environment displayed an apparent reversal of tolerance, their analgesic responses being similar to that of individuals receiving single acute Cnp exposures (FIG. 15).

A variety of factors, including ELF magnetic fields, have been shown to function as salient environmental specific cues and affect the subsequent expression of tolerance. This raises the possibility that the Cnp itself may at least partially serve as a cue for tolerance development. This may contribute in part to the apparent lack of a complete "cross-tolerance" to the analgesic effect of the Cnp to the δ opioid agonist DPDPE.

Associative, environmental or situation specific tolerance has been explained through classical conditioning, [Tiffany et al., 1981] although habituation involving both associative and non-associative components has also been proposed [Baker et al., 1985]. According to the conditioning model the distinctive context has become a conditioned stimulus that elicits associative tolerance.

In the present study it was found that similar patterns of tolerance developed whether the snails received nociceptive testing every day or only on the first and last days. This suggests that associative factors related to determining the thermal response latencies (i.e. hotplate testing) of the snails did not play a major role in the development of tolerance. This also minimizes the likelihood that tolerance arises from cues associated with the nociceptive assessment. This is consistent with the results of a number of investigations of opiate tolerance in rodents, as well as morphine tolerance in Cepaea.

Recent studies have focused on the possible neurochemical mechanisms involved in associative tolerance. Investigations with laboratory rats have suggested that neurotensin and possibly other neuropeptides implicated in memory may have a role in the mediation of associative tolerance [Girsel et al., 1996]. This does not preclude a role for other neuronal and second messenger systems that have been implicated in learning in both molluscs and rodents, and been shown to be sensitive to various types of magnetic fields.

A number of possible mechanisms have been proposed for the biological effects of magnetic fields [Kavaliers et al., 1994; Prato et al., 1995]. Among these, resonance models have predicated both increases and decreases in opioid analgesia along with effects at specific frequencies. These actions have been suggested to have effects on calcium and potassium ions and various messenger systems [Kavaliers et al., 1996; Kits et al., 1996; Prato et al., 1996; and Kavaliers et al, 1996], that are associated with the mediation of opioid actions and learning related processes. All of these could contribute to the Cnp induced expression of analgesia and decline in the opioid component with repeated exposures.

Vestibular System

The use of Cnp pulses appears to be valuable for affecting various vestibular components of mammals. With respect to humans, Cnps can be very valuable for the alteration of standing balance. Disruptions of the balance system such as motion sickness may possibly be treated with the use of Cnps without adverse side-effects such as nausea or sleepiness.

The Cnp shown in FIG. 3 was used to target the vestibular system in rodents (activity study; amplitude 100 mT), in deer mice (conditioned taste aversion study; amplitude 100 mT), and in rats (conditioned taste aversion study; amplitude 1–4 mT). The Cnp shown in FIG. 5 was also piloted in humans (balance study; amplitude 10– 60 mT). Note that FIG. 3 and FIG. 5 differ only in the length of the refractory period. In humans the refractory period (Feature 4 in FIG. 1) was 3 times longer than for rodents. The reason is that awareness lasts 3 times as long for humans who extrapolate each awareness period (approximately 400 ms) with cognitive function to three such periods (approximately 1200 ms).

Figure 5:
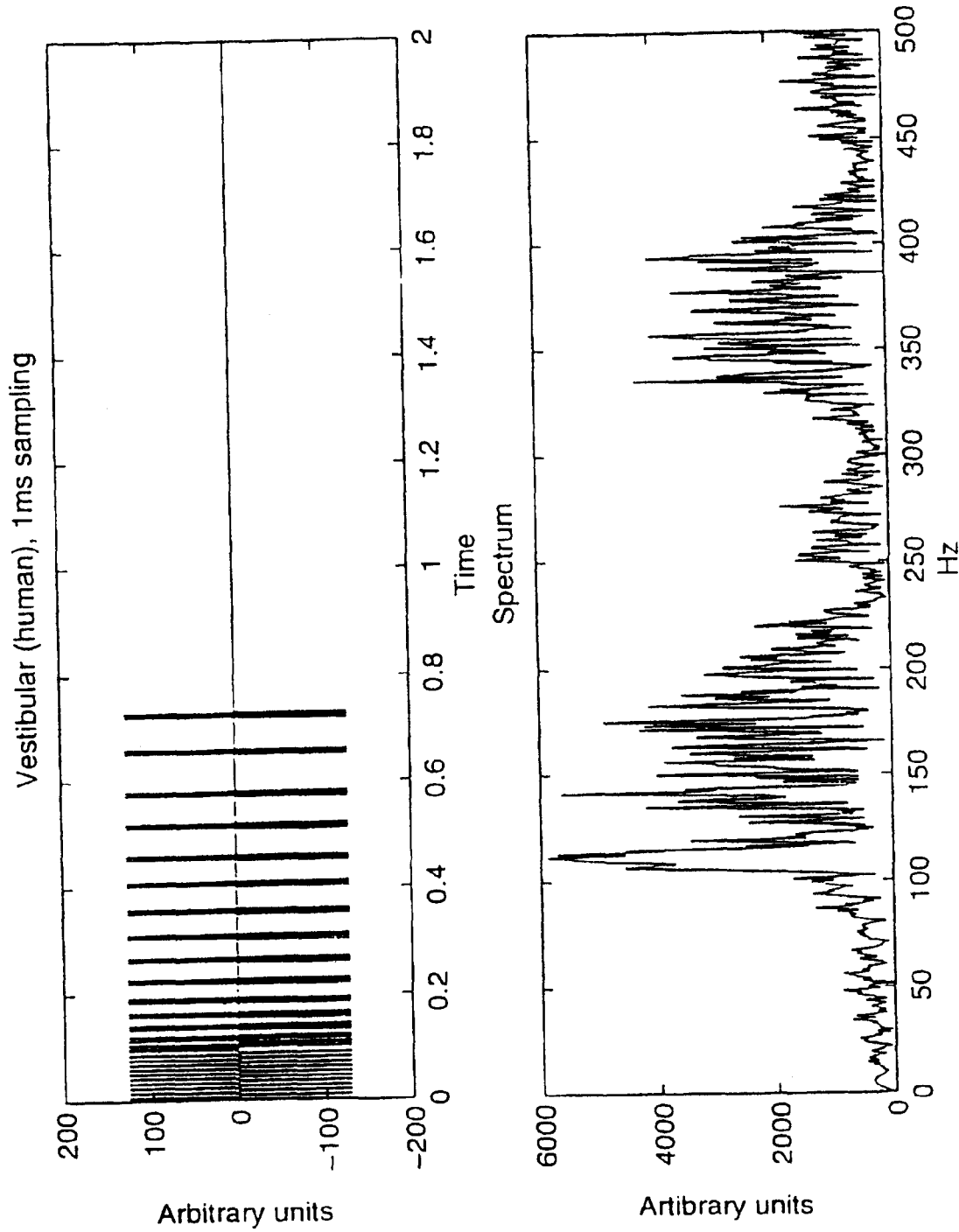
FIG. 5 shows detail of the Cnp used to target the human vestibular system. There are differences in the refractory period as compared to the Cnp targeted for rodents (See FIG. 3). The top panel corresponds to Cnp in time and the lower panel to the magnitude of the Fourier Transform of the Cnp.

The rate or waveform presentation was modulated from higher frequencies to lower frequencies and two different waveforms were used. FIG. 5 shows the magnitude Fourier transform of the Cnp, i.e. it is a magnitude spectrum of the positive frequencies and the maximum frequency possible was set to 500 Hz by the digital representation of the Cnp at a separation of 1 ms. Note, that FIG. 5 indicates that the power in the spectrum is at three major frequency ranges: 100–125; 125–240; 325–410. The high frequencies were needed since the vestibular system is a motor function and, therefore, has endogenous CNS frequencies of the order of 300Hz.

Two different waveforms were used to represent the electromagnetic activity of the vestibular system. This was necessary to provide a minimum resolution time (1 ms) at the highest frequencies. Initially, a two lobe waveform was used and then when the waveform rate was sufficiently reduced and the latency sufficiently long a five lobe waveform was used as it was believed to better mimic the underlying electrical activity of the target tissue.

Modulation of Anxiety

Severe anxiety has been shown to accompany depression. A Cnp has now been designed which significantly alters anxiety related responses in mice.

A Cnp designed to produce vestibular disturbance in deer mice produced a marked increase in activity (activity index =total of escape behaviors such as climbing attempts, jumps, centerline crosses) during a 10 minute Cnp exposure as compared to a 10 minute sham exposure (FIG. 17). The 100 μT Cnp exposure and sham condition were given while the animals were contained in a Plexiglass open-field box. The Cnp exposure also produced a significant decrease in the duration of grooming behaviors (FIG. 25).

Modulation of Behavioral Activities

Deer mice were exposed to a specific Cnp designed to interact with the vestibular system to characterize the effects of Cnp on behavioral activities. Individual deer mice were exposed to the Cnp or control conditions (sham or 60 Hz) for a 10 minute period while being videotaped and various behaviors were monitored. It was concluded from this study that specific pulsed magnetic fields (Cnps) may be designed to affect selectively a variety of behaviors. Acute exposures (5 min) are sufficient to produce a significant behavioral effect (FIGS. 19–25). Cnps were seen to affect rearing behaviors and general activity such as climbing and centerline crosses compared to the control groups. These result demonstrate that Cnps can be used to alter a variety of behavioral activities.

Taste Aversion

Field studies have indicated that deer mice, *Peromysciis Maniculatus*, developed long lasting avoidance of poisoned baits, whereas results of an early laboratory investigation of conditioned taste aversion (CTA) suggested the formation of taste aversions that extinguished rapidly. The applicants have examined in one set of experiments the acquisition and extinction of a conditioned taste aversion (sucrose paired with LiCl) in male and female deer mice. In another set of experiments, the applicants have examined the acquisition and extinction of conditioned taste aversion using sucrose alone in Wistar rats and in deer mice. The applicants also examined the effects of specific Cnps on taste aversion learning. Together, the results of these studies (FIGS. 26–29) demonstrate that Cnp can be used to modify taste aversion in deer mice and in Wistar rats.

A Cnp designed to interfere with vestibular processing was tested for aversive effects in two independent trials of conditioned taste aversion, or taste aversion learning. In one experiment, Wistar rats (N=24) that were exposed to the specific Cnp for one hour at being provided with a novel food item (sucrose solution) consumed significantly more sucrose solution when tested three days after exposure, as compared to sham exposed animals ($F_{1,23}=5.99$, $P=0.023$, $Eta^2=0.22$). In another experiment, deer mice (*Peromyscus maniculatus*) (N=43) were exposed to either the specific Cnp or a sham condition for one hour. After exposure, the deer mice were given access to water and apple juice simultaneously and the ratio of apple juice to total volume consumed (apple juice+water) was recorded. The deer mice exposed to the Cnp consumed significantly more apple juice than did the sham exposed mice ($F_{1,43}=3.95$, $P=0.05$). Though the exposure systems used in the two experiments were vastly different, the same specific Cnp was used. In both cases neither induced an aversion to the novel food. Results of prior investigations had shown that the specific Cnps were capable of inducing other specific behavioral affects in those species. Experiment one utilized a single coil (72 turns of 30 WG) wrapped around an aluminum (1.3m× 1.1 m) cage rack (100–700 $\mu$T Cnp exposure, normal Earth earth magnetic field sham (Michon et al, 1996)). The exposure system for experiment two consisted of three pairs of nested orthogonal Helmholtz coils (Prato et al, 1996) (100±0.1 $\mu$T, 3-D±0.1 $\mu$T zeroed Earth field magnetic sham).

The results of the studies using sucrose and LiCl showed that reproductive male and female deer mice developed a rapid conditioned taste aversion to a sucrose solution that was paired with lithium. There was a complete extinction of the aversion after 4–5 days with no evidence of a residual aversion 10 days later which is a contrast to the longer lasting aversions generally evident in laboratory rats. There were also sex differences in the conditioned taste aversion with male deer mice displaying a longer lasting aversion and slower extinction than females.

The Cnp exposure did not elicit a conditioned taste aversion, but rather it reduced the neophobic responses of males to a novel taste and sex difference in baseline taste preferences. Further experiments conducted at Laurentian University also revealed that the specific Cnp similarly reduced neophobic responses and aversions to novel food items in laboratory rats.

Overall, these findings indicate that the effect of the specific Cnp, in at least a taste aversion paradigm, is dependent on the "characteristics" of the magnetic field, not the exposure system, amplitude, geographical location or species tested.

Learning

All behaviors, including learning, originate as a pattern of electrical activity in the brain. Using specific Cnps, specific behaviors can be altered inferring that specific areas of the brain can be selectively affected. Previous studies using Cnps have shown alterations in behaviors such as language, memory, suggestibility, mood and understanding. It is anticipated that combinations of specific Cnps will result in predictable alterations of memory and learning.

Epilepsy

The use of Cnps has great potential to treat epilepsy safely, a serious problem associated with brain trauma.

Depression

The potential to treat depression with Cnps is enormous, in both clinical and model terms (Baker-Price and Persinger, 1996). Also, related disorders such as 'seasonal affective disorder' may prove to be susceptible to Cnp treatment. It has been envisioned that the equipment required for this Cnp treatment would be portable, about the size of a 'Walkman', and have earphone sized head coils.

The designed pulsed magnetic fields (Cnps) of the present invention can be used effectively to treat a variety of physiological and psychological conditions in a safe and effective manner. Any living organism including humans and animals can be subjected to the Cnps of the present invention. By safe and effective as used herein is meant providing sufficient potency in order to decrease, prevent, ameliorate or treat a a physiological or neurological disorder affecting a subject while avoiding serious side effects. A safe and effective amount will vary depending on the age of the subject, the physical condition of the subject being treated, the severity of the disorder, the duration of treatment and the nature of any concurrent therapy.

The subjection of a subject to effective Cnps exposures of the present invention is defined as an amount effective, at dosages and for periods of time necessary to achieve the desired result. This may also vary according to factors such as the disease state, age, sex, and weight of the subject, and the ability of the Cnps to elicit a desired response in the subject. Dosage or treatment regima may be adjusted to provide the optimum therapeutic response. For example, several divided doses or treatments may be administered daily or the dose may be proportionally reduced as indicated by the exigencies of the therapeutic situation.

The Cnps of the present invention may be subjected to a mammal alone or in combination with pharmaceutical agents or other treatment regimes.

EXAMPLES

Example 1

Materials and Methods

Animals

Snails were collected from old field sites in London, Ontario which did not have any overhead or underground electric transmission lines (<0.01 $\mu$T ambient magnet fluctuation). Snails were then individually numbered by applying a small identifying mark on the apex of the shell using non-toxic colored fingernail polish. The individually numbered animals were held in a terrarium (ambient fluctuating magnetic fields <0.4 $\mu$T) under indirect natural and fluorescent, lighting at an approximate 12 h light/ 12hr dark cycle (LD=12:12 L=250 $\mu$W/cm$^2$), at 20±2° C., with lettuce available ad lib.

Assessment of Nociception

As the activity of gastropods is affected by their state of hydration [Smith 1987], all snails were allowed to fully hydrate under a saturated atmosphere at 20±2° C. before being tested. Individual fully-hydrated snails were placed on a warmed surface ("hotplate"40±0.2° C.) and the latency of their "avoidance" of the thermal stimulus, was determined. The avoidance behavior was a characteristic elevation of the anterior portion of the fully extended foot, the behavioral endpoint being the time the foot reached maximum elevation [Dyakonova et al., 1995]. After displaying this aversive, or more appropriately, "nociceptive" response [ Kavaliers et al., 1983], individual snails were removed from the thermal surface. An increase in response latency may be interpreted as an antinociceptive or "analgesic" response [Thomas et al., 1997]. The hotplate, which does not produce any magnetic fields, consisted of an aluminum waterjacket with a stainless steel top (33×33cm) with water pumped through it from a circulating water bath.

Experimental Apparatus

Groups of 15 snails were placed in translucent polypropylene containers (12 cm square, 5 cm high) in the center of three mutually orthogonal Helmholtz coils (1.2 m for the coil that generated a vertical field and 1.1 m and 1.0 m for the coils that generated horizontal fields). Details of the coils and amplifiers are provided in Prato et al.[Prato et al., 1996]. A computer driven 8-bit resolution digital to analog converter (S. Koren, Neuroscience Research Group, Laurentian University, Sudbury, Ontario) was used to produce the pulsed waveforms. Magnetic fields were measured with a fluxgate magnetometer (model FGM-3DI) and a field monitor (model ELF-66D), both Walker Scientific, Worcester, Mass.

Magnetic Field Exposure Conditions

Figure 9:
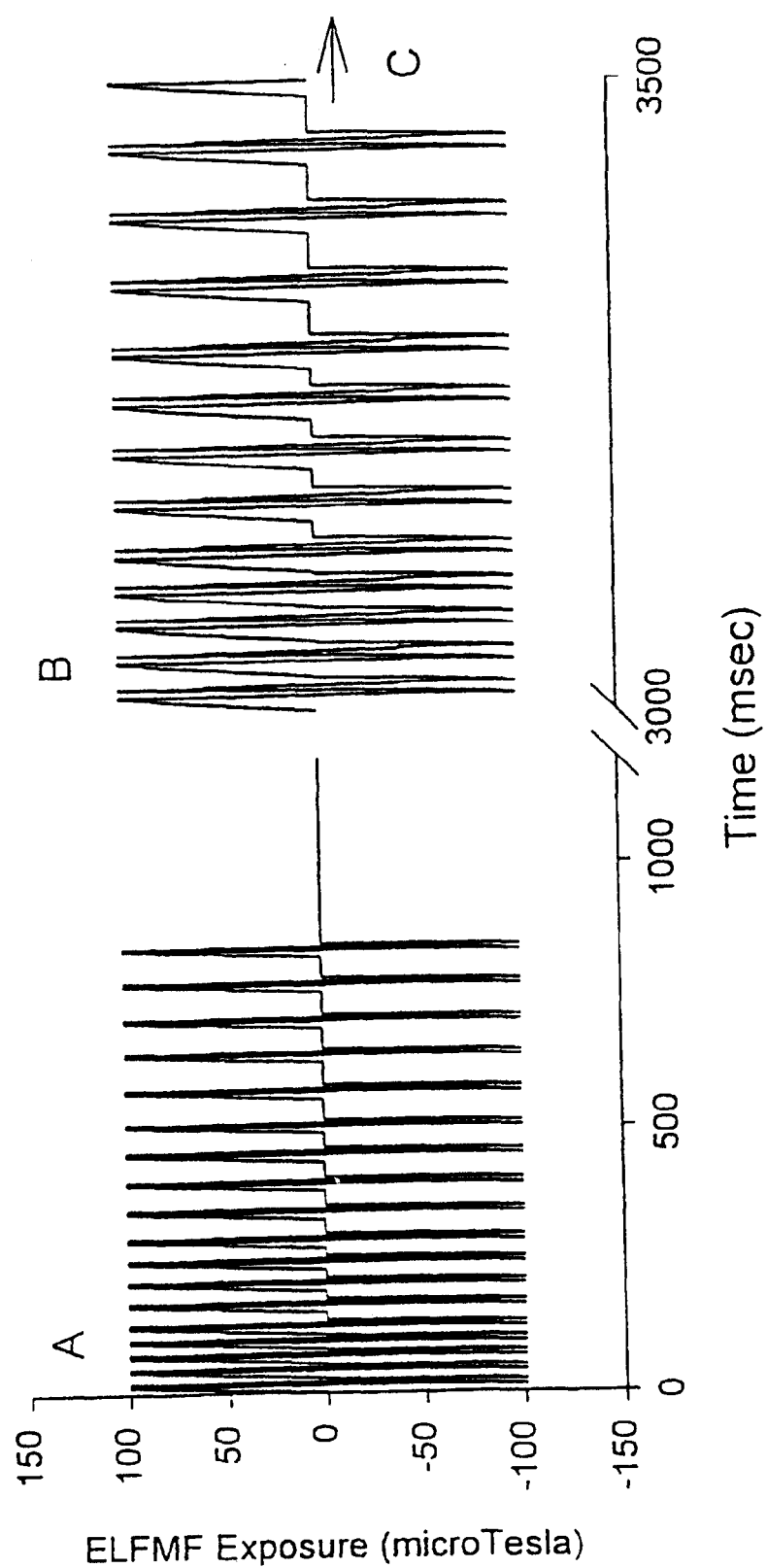
FIG. 9 shows the effect of a complex neuroelectromagnetic pulse (Cnp), designed to increase analgesia, consisting of a series of time-varying extremely low frequency components (<300 Hz) (A) repeated between refractory periods of several seconds (B). The Cnps are repeated for the length of the exposure period (15 or 30 mins) (C). Peak Cnp exposure is set at 100 μT vertical, with the horizontal and vertical static magnetic field set to counter the Earth magnetic field. Sham exposures consisted of a three-dimensionally (3-D) zeroed Earth magnetic field (3 orthogonal nested Helmholtz coils tuned to oppose the Earth magnetic field to within ±0.1 μT, horizontal component =14.7 μT, vertical component 43.3 μT.)

The 15 and 30 min magnetic field exposures consisted of a specific low frequency pulsed magnetic field (Cnp) (FIG. 9) set to 100 $\mu$T peak amplitude in the vertical direction.

Sham exposures consisted of a three-dimensionally (3-D) zeroed Earth magnetic field (Helmholtz coils tuned to oppose the Earth's magnetic field to within ±0.1 $\mu$T horizontal component=14.7 $\mu$T, vertical component=43.3 $\mu$T.) Results of prior investigations [Thomas et al., 1997; Thomas et al., 1997 (in press)] had established that there were no significant differences in the response latencies of 3-D zeroed Earth magnetic field sham exposed snails and those that were exposed to an ambient Earth magnetic field sham condition.

Example 2

Materials and Methods for Taste Aversion Studies

Animals

Male and female sexually mature deer mice (20–25 g and approximately 5 months of age) were housed in mixed-sex sibling groups (3–5 animals per group) in polyethylene cages provided with cotton nesting material and Beta chip bedding. Food (Purina Rat Chow) and water were available ad libituni. The reproductive mice (males scrotal, females cyclic) were held under a reproductively stimulatory (Desjardins et al. 1986; Nelson et al. 1992), long day, 16 h light: 8 h dark cycle (light 0600–2200 hr) at 20+/–2° C. The laboratory bred deer mice (15–20 generations) were from a population of wild caught animals originally present in the interior of British Columbia (Canada) near Kamloops (50° 45'N, 120° 30'W).

Additional characteristics of this wild and laboratory population are provided in Innes and Kavaliers (1987).

Experimental Procedures

There were five phases in this first experiment: a habituation phase; a conditioning phase: a postconditioning recovery phase, an extinction phase and a re-test phase.

Habituation Phase

Males (n=21) and females (n=22) were individually housed for 10 days with food and tap water, in standard drinking bottles, available ad libitum. For 4 days the mice were water deprived overnight (dark period). Each morning they were given two drinking tubes containing tap water and the total amount of water consumed over 90 min. was recorded For the remainder of the day tap water in standard drinking bottles was available ad libitum. The drinking tubes consisted of 15 ml graduated polypropylene conical tubes (Falcon 2092, Becton Dickinson, Lincoln Park, N.J., USA), with screwable caps that were fitted with stainless steel water spouts with ball bearing. With these drinking tubes fluid intake could be accurately determined to 0.25 ml. Individual body weights were recorded at night immediately after the removal of the water bottles and in the day directly after the drinking tubes were removed.

Conditioning Phase

On Day 5 overnight water deprived mice were given the two drinking tubes each of which contained a 0.3 M sucrose solution. After 90 min. the total sucrose intake was recorded and mice were immediately injected intraperitoneally (i.p.) with 20 ml/Kg of either a 0.15 M LiCl solution or 0.9% isotonic saline solution. After injection the water bottles were returned and the mice were then left undisturbed until the evening when their bottles were removed and the mice were weighed. Male and female mice were randomly assigned to the UCI and saline groups.

Post Conditioning Recovery Phase

For two days after conditioning (days 6 and 7) mice were kept on their nightly water deprivation schedule. In the mornings they were presented the two drinking tubes with tap water for 90 min. after which water from the standard drinking bottles was provided ad libitunt. Body weights were recorded twice daily as previously described.

Extinction Phase

On days 8–11 individual mice were presented-two drinking tubes, one containing tap water and the other one holding the 0.3 M sucrose solution in the morning drinking period. Water and sucrose solution intakes were recorded for 90 min. after which tap water from standard water bottles was available ad liitum. The position of the two drinking tubes was varied: half of the mice in each experimental group (LiCl and NACI) had water on the right and the other half had sucrose on the right. To correct for possible individual preferences, the position of the water and sucrose tubes were reversed on subsequent days. Deer mice were weighed twice daily.

Recovering Phase

After extinction of the conditioned taste aversion the male and female deer mice were left undisturbed for 10 days with ad libituwn access to food and tap water.

Retesting Phase

Individual male and female mice were replaced on the overnight water deprivation schedule. For two days the water deprived mice were given in the morning two drinking tubes, one containing water and the other 0.3 M sucrose and their total fluid intakes were determined over 90 min. After this 90 min. period they were provided with ad libitum access to the standard water bottles.

Total fluid intakes were analyzed by a two way individual analysis (MANOVA) with sex (two levels; mails and females) and treatment (two levels; LiCl and NaCI) as between-subject factors and intake as a repeated-measure within-subjects factor (eleven levels; Habituation (four days), conditioning (pairing and 2 post injection days), extinction (four days)). In order to evaluate the effects of sex and treatment on the fluid intakes on each day mean comparison were planned a priori in the MANOVA model. Since fluid intake displayed a Poissonian distribution the data were square-root transformed before analysis. As there were some zero intakes, 0.50 was added to all values before transformation.

Preference data from extinction and re-test phases were expressed as the percent of sucrose (arcsin transformed) consumed in the total fluid. These preference data were analyzed by a two way MANOVA, with sex (two levels; males and females) and treatment (two levels; LiCl and NaCI) as between subject factors and percent of sucrose as a repeated-measure within subjects factor (six levels: 4 extinction days+2 re-test days). In order to evaluate the effects of sex and treatment on sucrose preference for each experimental day, mean comparisons were planned a priori in the MANOVA model.

Body weights were analyzed by a two way MANOVA with sex (2 levels; males and females) and treatment (2 levels; LiCl and NaCI) as between-subject factors and intake as a repeated-measure within-subjects factor (21 levels). In order to evaluate the effects of sex and treatment on the mice body weights for each expeomental day, mean comparisons were planned a priori in the MANOVA model. All hypothesis tests used a=0.05 as the criterion for significance.

Magnetic Field Generation

In the magnetic and sham field exposure conditions mice were placed in a Plexiglas box in the centre of three mutually orthogonal Helmoltz coils (1.2 m diameter for the coil that generated a vertical and 1.1 m for the coils that generated horizontal fields; details of the coils and amplifiers are provided in Prato et al. (1994). A computer driver with a 8 bit resolution digital to analog converter produced the pulsed waveforms. Magnetic fields were measured with a fluxgate magnetometer (model FGM - 3DI) and a field monitor (model ELF - 66D; both Walker Scientific, Worcester, Mass. USA).

Magnetic Field Exposure Conditions

The magnetic field exposures consisted of a specific low frequency pulsed magnetic field set to 100+/−0.1 $\mu T$; peak amplitude in the vertical direction.

Sham exposures consisted of a three dimensionally (3-D) zeroed earth field (Helmoltz coils tuned to oppose the earth's field to within +1/−0.1 $\mu T$; horizontal component=14.7 $\mu T$, vertical component=43.3 $\mu T$).

Example 3

Experimental Procedures, Opioid Experiments

Experiment 1

Each day for 9 consecutive days, at midphotophase, separate groups (n=15 per group, N=120) of hydrated snails were exposed to either the specific pulsed magnetic field or sham magnetic field for either 15 or 30 min. On day 10, the exposure conditions were reversed for each group, with sham animals receiving the Cnp and Cnp exposed animals receiving sham exposure. Response latencies of the snails were determined prior to (Pre), immediately after (0) and 15, 30 and 60 min after exposure. One individual carried out the Cnp and sham exposures while a second experimenter, in a separate room, determined the response latencies. Results of previous investigations had established that tolerance to the analgesic effects of morphine in Cepaea was evident after 7 days of daily repeated acute treatments [Kavaliers et al., 1983].

Experiment 2

Each day for 9 consecutive days, at midphotophase, other separate groups (n=15 per group, N=60) of hydrated snails were exposed to either the specific Cnp or sham magnetic field for 15 or 30 min and then (except for days I and 9) immediately returned to their home container. On days I and 9 response latencies of the snails were individually determined prior to (Pre), immediately after (0) and 15, 30 and 60 min after exposure, after which they were returned to the home container.

Experiment 3

After 9 days of daily repeated acute Cnp or sham exposure (15 min) and assessment of nociception (pre, 0, 15, 30, 60 min), other groups of snails (N=30) were exposed (day I0) to their respective exposure conditions while held in a novel environment. The novel environment consisted of a modified version of the previous polypropylene exposure container. Pieces of coarse garnet sandpaper were fitted and glued to the top and bottom inside of the container and then rinsed with carrot juice (whole blended carrot). Carrot is assumed to be a novel food item, as the laboratory housed snails were not exposed to this food item at any time. In addition, other naive snails (N=60) were exposed to either a Cnp or sham condition while housed in either the C, "normal" or "novel" exposure environment. The novel environmental condition had no effect on the magnetic field exposure characteristics.

Experiment 4

After 9 days of daily repeated acute Cnp or sham exposure (30 min) and assessments of nociception (pre, 0, 15, 30, 60 min), individual snails (N=60) were injected (day 10 with either DPDPE (0,05 $\mu g/1.0$ $\mu l$ saline, Research Biochemicals, Natick, Mass.) or 0.9% saline vehicle (1.0 $\mu l$). Nociceptive sensitivity was determined prior to and 15, 30, 60 min after injection. This dose of DPDPE was established in a prior study to elicit an analgesic response comparable in magnitude to that observed after a single acute Cnp exposure [Thomas et al., 1997 (in press)]. All solutions were injected with a 2.0 µl microsyringe (No. 75, Hamilton, Nev.) in either the vicinity of, or directly in, the mantle cavity into the haemocoel. Injections were made on the basis of 1.0 g body mass. The body mass of snails, without shells, range from 0.7 to 1.3 g.

Experiment 5

The Thermal response latencies of snails receiving Cnp and treatments with opiate antagonists.

Snails were injected with either the prototypic opiate antagonist, naloxone (1.0 µg/1.0 µl saline), the specific δ antagonist, naltrindole-5'-isothiocyanate (5'-NTII, 0.1 µg/1.0 µl saline) or saline vehicle (1.0 µl) prior to being exposed for 15 min to the specific Cnp. Other groups of snails received either acute sham magnetic field, acute Cnp exposure (15 min) or daily repeated (9days) acute Cnp exposure. There were no significant differences in response latencies between opiate antagonist treated animals (naloxne, 5'-NTII) and those receiving Cnp exposures (acute daily exposure for 9 consecutive days). Acute Cnp exposure produced significantly greater response latency than all other groups (Tukey's HSD, P<0.05).

Experiment 6

The effect of Cnp exposure on behavioral activities in deer mice.

Individual deer mice (Peromyscus maniculatus) (N=46) were exposed for 10 min (analyzed in 5 min segments), while being videotaped, to either; a normal Earth magnetic field, 14.7 µT horizontal and 43.3 µT vertical sham condition, a 3-D zeroed Earth magnetic field (+/–0.1 µT) sham condition, 60 Hz (100 +/–0.1 µT vertical) sinusoidal magnetic field or a specific Cnp (100 +/–0.1 µT peak) condition. The exposure chamber consisted of a 33 cm Plexiglass cube held within three pairs of nested orthogonal Helmholtz coils (1.2m×1.1 m×1.0 m) (Prato et al., 1996). The videotapes were then analyzed by an experimenter blind to the exposure conditions. Various behavioral activities were recorded (center-line crossings, climbing attempts, rearing and duration of grooming episodes) indicating that the pulsed Cnp exposed deer mice had a significantly increased level of activity compared to the normal Earth magnetic field, 3-D Earth magnetic field sham and 60 Hz MF exposure conditions. There were no significant differences in activity between the normal Earth magnetic field, 3-D zeroed Earth magnetic field sham or 60 Hx MF exposure conditions.

Statistical Analysis

Data were analyzed with multivariate, repeated measures, one-way and two-way analyses of variance (ANOVA) using The Statistical Package for Social Sciences (SPSS 7.0). Post-hoc analyses were carried out using Tukey's HSD test. All hypotheses tests used α=0.05 as the criterion for significance.

Example 4

Experimental Results, Oploid Studies

Experiment 1

Acute single exposure to the Cnp elicited a significant ($F_{4,115}$=268.59, P<0.001, $Eta^2$=0.90) increase in response latency indicative of the induction of analgesia at 0, 15. 30 and 60 min post exposure. The 30 min exposures induced a significantly greater amplitude of analgesia than did the 15 min exposure at 0, 15 and 30 min post exposure $F_{4,113}$=4.71, P<0.01, $Eta^2$=0.14) (FIG. 10). In both cases, maximum analgesia was elicited at 0-15 min post-exposure with significantly lower response latencies at 30 and 60 min post exposure. Repeated daily exposures to the Cnp resulted in a significant reduction in the levels of analgesia. By the third day, no significant differences in the increases in response latency were elicited by the 15 and 30 min exposures (FIGS. 11A, 11B and 12A, 12B).

Figure 12A:
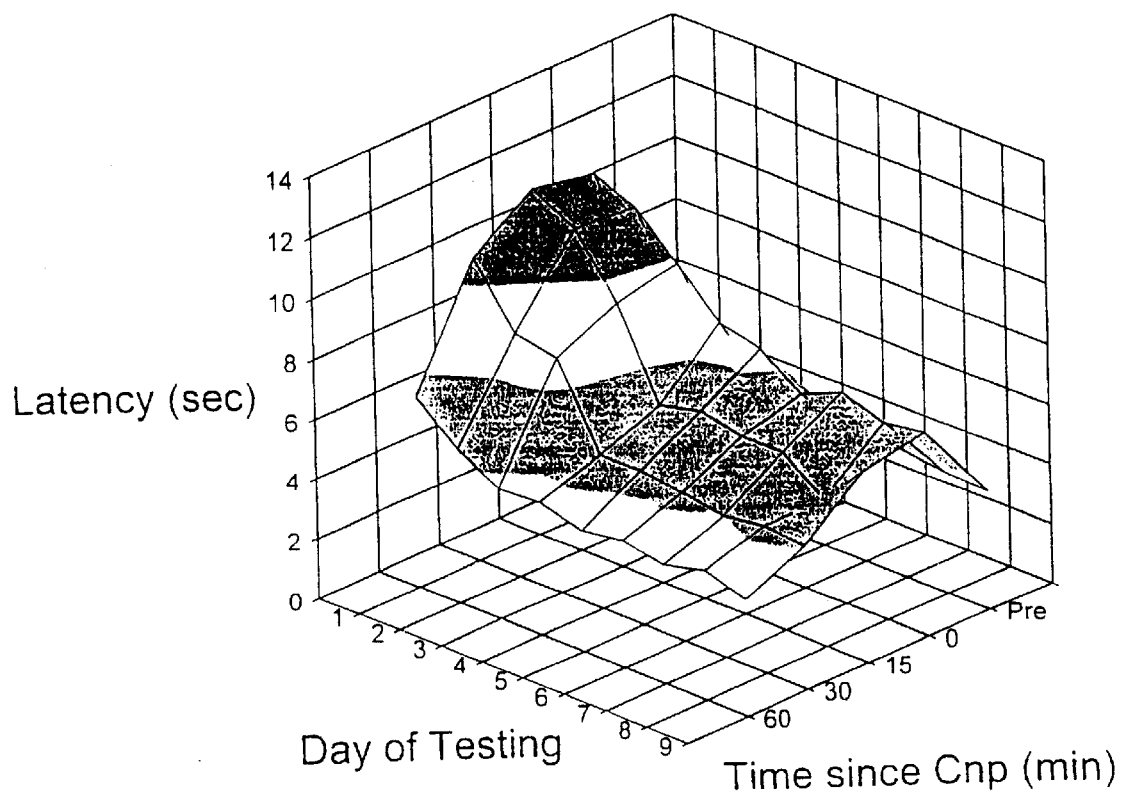
Figure 12B:
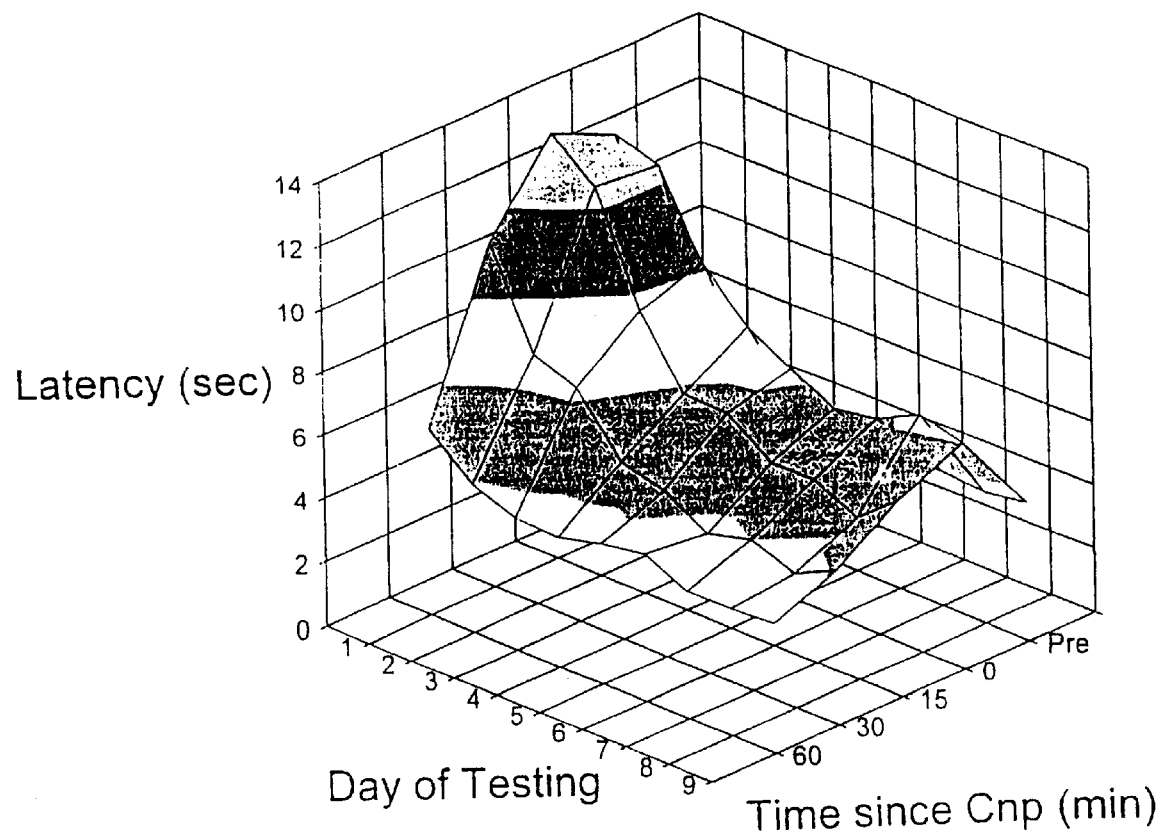
Figure 12C:
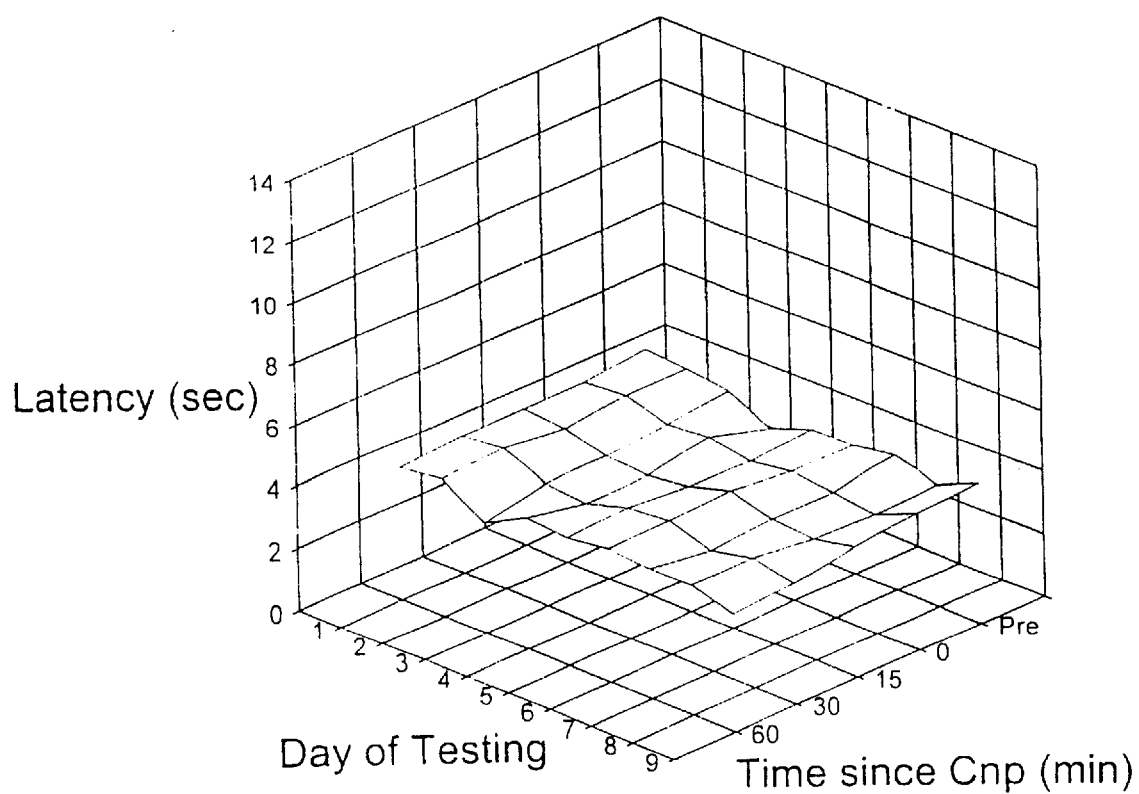
Figure 13A:
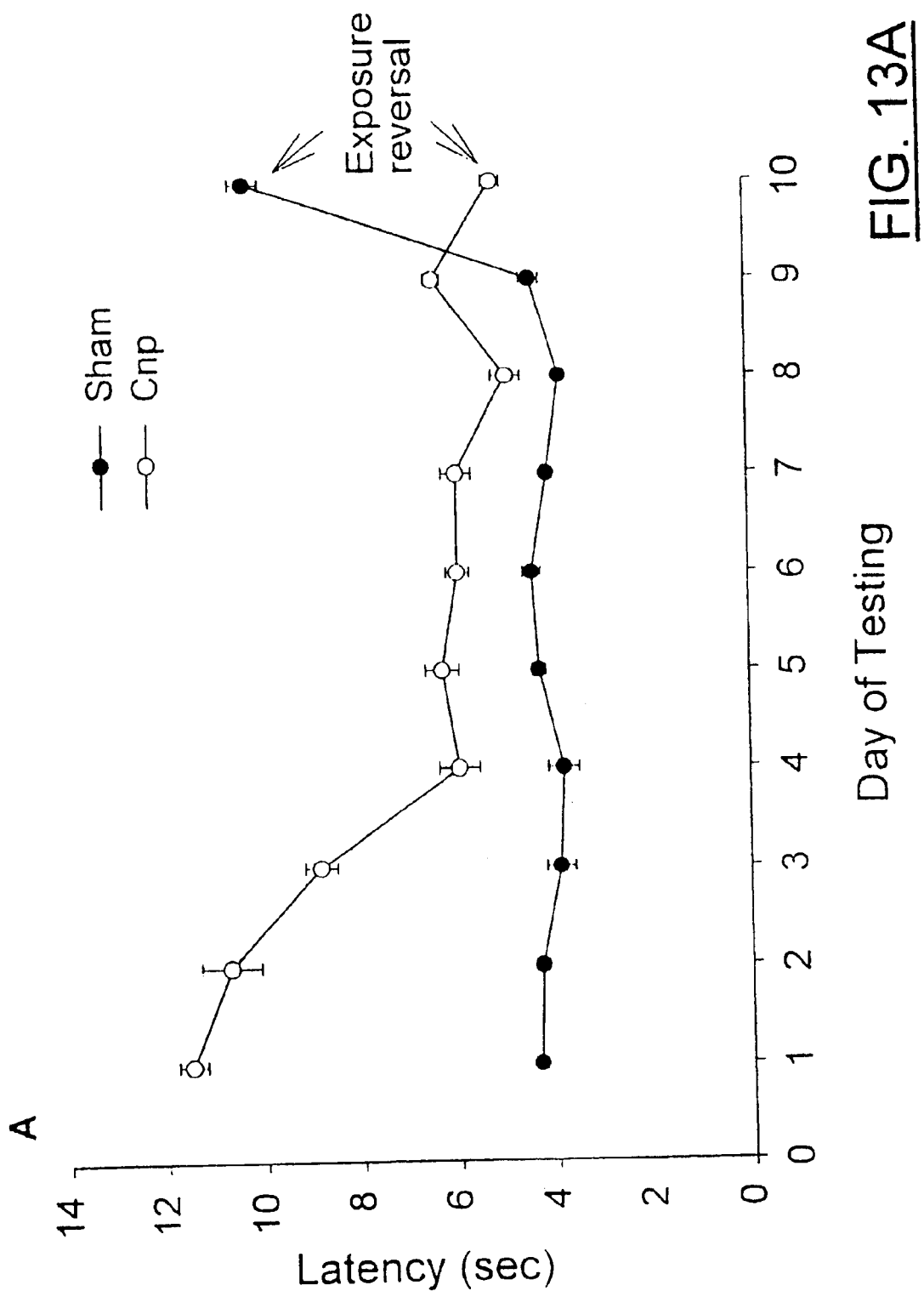
Figure 13B:
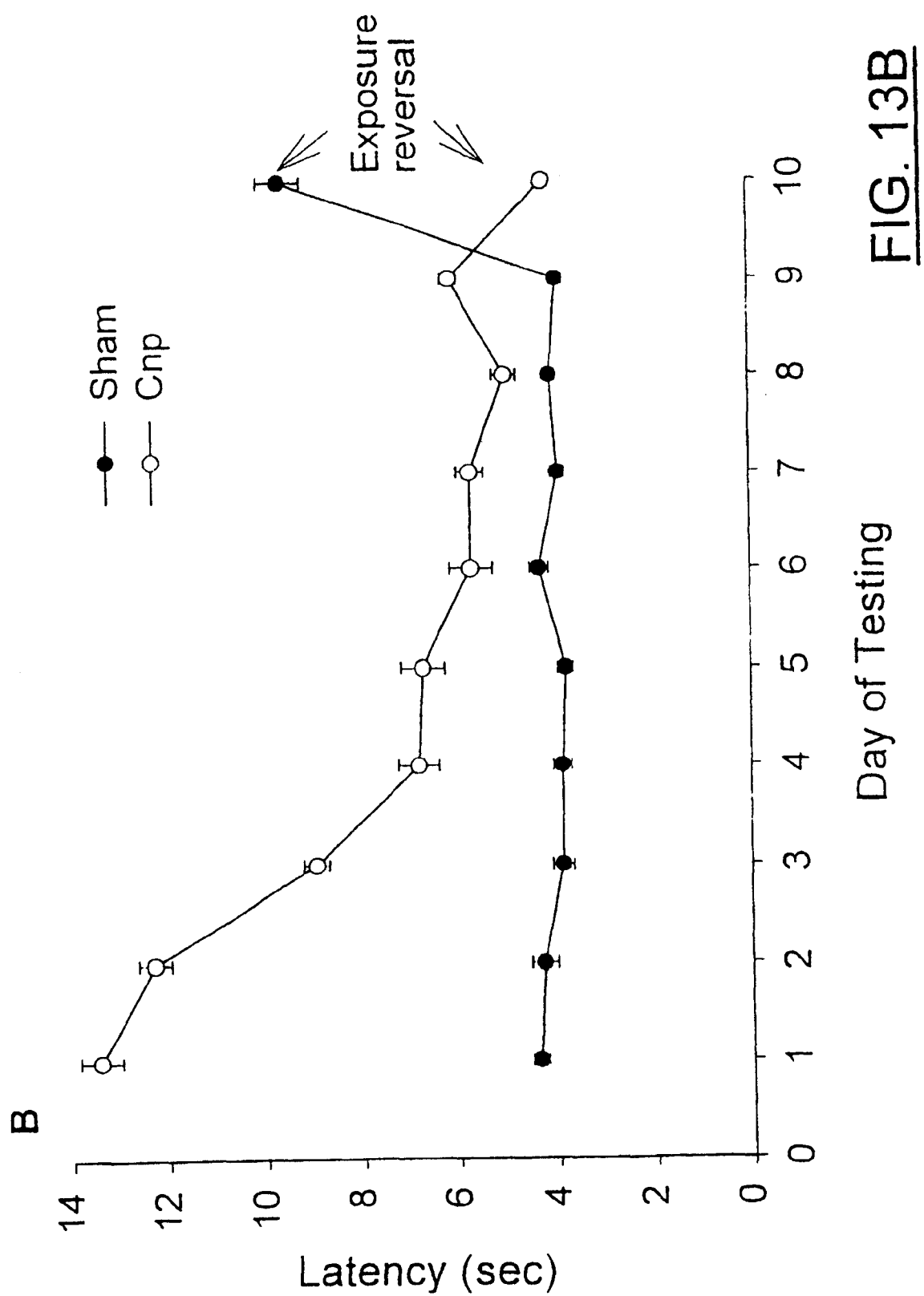

The analgesic effects of daily repeated acute exposure to a Cnp magnetic field were highly significant ($F_{1,55}$=2856.4, P<0.001, $Eta^2$=0.95) (FIG. 12A), consistently producing a significant increase in response latency. Repeated analysis of variance revealed a significant reduction in daily induced analgesia ($F_{8,48}$=86.29, P<0.001, $Eta^2$ 0.94) (days 1 to 9); and a significant reduction in the duration of analgesic effect ($F_{4,52}$=230.66, P<0.001, $Eta^2$=0.95) (pre-exposure and 0, 15, 30, 60 min after daily Cnp exposure) (FIG. 12A). Although the amplitude of Cnp induced analgesia was significantly reduced after the repeated daily exposure, a significant analgesia was present after each Cnp exposure (Tukey's HSD, P<0.05) (FIGS. 12A, 12B). Maximum reductions in analgesia were evident after day 6 of exposure to the Cnp, with no significant further reduction of response latency on subsequent days. There were no significant changes in either pre-exposure basal response latencies or the nociceptive responses of the sham exposed snails (FIGS. 12A, 12B, 12C). Reversal of the exposure conditions on day 10 produced a significant shift in response latency ($F^{452}$=110.8, P<0.001, $Eta^2$=0.90). The Cnp exposure induced significant analgesia in the previously sham exposed snails while the snails now exposed to the sham condition showed no significant increase in response latency (FIG. 13A, 13B).

Results of previous studies [Thomas et al., 1997 (in press) and Table 2 ] had established that pre-treatment with either the prototypic opiate antagonist, naloxone, or the specific δ receptor directed antagonist, 5'-NTII, significantly reduced, but did not block, the analgesic effect of the Cnp. The saline vehicle had no significant effect on response latency. These inhibitory effects of the opiate antagonists on the amplitude and time course of Cnp induced analgesia were comparable to the reduction in response latency and levels of analgesia that were obtained by repeated daily exposure (6–9 days) to the Cnp (Table 2).

Experiment 2

Snails that were exposed to the Cnp daily for either 15 or 30 min, but tested for nociceptive responses only on days I and 9, showed a significant reduction in Cnp induced analgesia ($F_{1,110}$=3144.4, P<0.001, $Eta^2$=0.93). The extent of this reduction was not significantly different from that seen in snails that received daily acute Cnp exposures and nociceptive assessments. There were no significant differences in pre-exposure or sham exposure latencies.

Experiment 3

The presence of a novel environment on day 10 of the repeated daily exposures to the Cnp caused a significant increase in the level of Cnp induced analgesia ($F_{1,27}$=250.6, P<0.001, $Eta^2$=0.90)(FIG. 15). The amplitude of the analgesic response evident in the novel environment was significantly greater than on day 9 of the daily repeated exposures to the Cnp ($F_{1,27}$=6.98, P<0.01, $Eta^2$=0.24). The elevated response latencies evident following exposure to the Cnp in the novel environment on day 10 were not significantly different from those of day 1 of the repeated exposures under normal environmental conditions. Other groups of naive snails receiving an acute exposure to the Cnp or sham condition (15 min), while in either the normal or novel environment, showed elevated response latencies indicative of Cnp induced analgesia ($F_{1,58}=248.76$, $P<0.001$, $Eta^2=0.90$). There were no significant differences in the levels of analgesia induced in the two environmental conditions ($F_{158}=1.31$, $P>0.50$, $Eta^2=0.04$). There were no significant differences in pre-exposure or sham exposure latencies.

Experiment 4

Treatment with the specific δ opiate agonist, DPDPE, produced a significant analgesic effect in snails that had received daily repeated sham magnetic field exposures for 9 days ($F_{1,59}=86.97$, $P<0.001$, $Eta^2=0.87$) (FIG. 16). This analgesic effect was similar to that previously observed in naive unexposed snails treated with DPDPE (0.05 μg 1.0 μl) [Thomas et al., 1997 (in press)]. Snails that received acute (15 min) exposures to the Cnp and were injected with DPDPE also displayed a significant analgesic response, with increased response latencies at 15 and 30 min post-injection. However, the magnitude of this analgesia was significantly lower than that displayed by the sham exposed DPDPE treated snails (FIG. 16). The level of analgesia induced by DPDPE in the snails that had received 9 days of daily repeated exposures to the Cnp was similar to the analgesic effect elicited by the Cnp exposure on day 9 of the repeated exposures. The saline vehicle injection (1.0 μl) had no significant effect on response latencies. There were no significant differences in pre-exposure or sham exposure latencies.

Example 5

Experimental Results Taste Aversion Studies

Total Fluid Intakes

The total fluid intakes across the various experimental phases are shown in FIG. 27. Overall there was a significant interaction of treatment by sex by time ($F_{(10,390)}=2,09$; $P=0.02$). By the 4th day of the habituation phase all of the overnight water deprived males and females consumed similar amounts of tap water during the 90 min. presentation of the drinking tubes. Likewise, an the pairing day males and females assigned to both treatment groups drank the same amount of the novel sucrose solution. The amount of sucrose consumed was not different from that of the tap water on the last day of the habituation phase. Similarly, the two sexes and treatment groups of deer mice did not differ in the total water intakes in the post conditioning (recovery) days as well as on the first two days of the extinction phase. On third day of the extinction phase females overall drank significantly mare than males ($F_{1,39}=8.42$; $P=0.006$). This sex difference was highly significant for the NaCl treated mice ($F_{(1,18)}=5.50$; $p=0.02$). though not for the LiCl treated mice ($F_{(1,19)}=3.32$; $p=0.09$). On the fourth day of the extinction phase there were no significant male-female or group differences in total fluid intakes.

On the re-test days the MANOVA showed that total fluid intakes of females were significantly greater than those of males on both days (main factor sex RE-TEST-1:$F_{1,39}=$ 6.17; $P=0.017$/main factor sex RE-TEST-2: $F_{(1,39)}=5.93$; $P=0.019$).

Percent Sucrose Intake

The percent of sucrose consumed by the deer mice during the extinction and the retest phases is shown in figure The overall analysis showed a significant main effect of treatment ($F_{(1,108)}=0.45$: $P=0.003$). a significant interaction of treatment×time ($F_{(3,108)}=3.481$; $P=0.02$) with the interaction treatment×time×sex approaching significance ($F_{(3,108)}=$ 2.609; $P=0.05$). The MANOVA showed that on the first and second days of the extinction phase LiCl treated male and female mice ingested a significantly lower percent of sucrose (first day: 13%; second day. −28%) than vehicle treated males and females (first day: 58%; second day: 66%, with no significant sex difference) mice (First extinction day: $F_{(1,36)}=1$ 9,00; $P=0.001$/Second extinction day: $F_{(1,36)}=$ 17,35; $P=0.0002$). On the third extinction dav only LiCl treated males still showed a significant reduction in the percent of sucrose solution ingested (males: $F_{(1,18)}=4,12$- $P=0.049$/females: $F_{(1,18)}=1.96$; ns). On this day the percent of sucrose intake of the LICL treated males was 46%. while that of vehicle treated males was 70% of sucrose. Conversely, the sucrose preference of females was equally high in both the LiCl (61%) and vehicle (76%) groups. By dav 4 also the males had recovered from the conditioned sucrose aversion and the percent of sucrose drunk was not significantly different between sexes and treatments (overall mean).

On the re-test phase, ten days after recovering from the taste aversion all of groups displayed a similar marked preference (80%) for the sucrose solution, indicating that the greater total fluid intake displayed by females did not reflect a sex difference in taste preferences (FIG. 28).

Body Weights

There were no significant sex differences or effects of treatment on body weights.

Total Intakes

The total fluid intakes across the various experimental phases are shown in FIG. 27 Overall there was a significant main effect of sex ($F_{1,195}=4.28$; $P=0.045$) as well a significant interaction of sex x intake in time ($F_{(5,195)}=2.43$; $P=0.036$). The MANOVA showed that on the pairing day, when apple juice and the magnetic/sham field were presented, males and females did not differ in their total intakes of apple juice.

On the two days after the magnetic/sham field exposure (sucrose and water presented), there was a significant interaction sex×field condition (POST-1: $F_{(1,39)}=4.16$; $P=0.048$/ POST-2: $F_{(1,39)}=4.53$; $P=0.043$). Mean comparisons revealed hat only sham exposed females displayed a greater intake than sham-exposed males (FIG. 28). This effect was stronger on the first day post-magnetic/sham field exposure when sham-exposed females drank more than either magnetic field-exposed females and or males of both exposure groups (Sham Females v s Sham males: $F_{(1,19)}=9.55$; $P=0.004$/Sham Females vs Pulse females: $F_{(1,20)}=7.61$; $P=0.009$/Sham females vs Pulse males. $F_{(1,19)}=9.19$; $P=0.004$). On the second day following the magnetic/sham exposure females of the sham group still consumed a significantly greater amount of fluid than the sham-exposed males ($F_{(1,19)}=4.21$; $P=0.047$). On the apple juice re-presentation day males and females, in both magnetic and sham exposed groups, did not differ in their total fluid intake.

Percent of Sucrose

All of groups displayed a similar marked preference (80%) for the sucrose solution, indicating that the greater total fluid intake displayed by females did not reflect a sex difference in taste preferences (FIG. 26).

Percent of Apple Juice

The percent of apple juice consumed by male and female deer mice on the third day after exposure to the magnetic/sham field are shown in FIG. 28. There was a significant main effect of treatment ($F_{(1,39)}$=5.28: P=0.02). Mean comparisons revealed that the effect of the pulse on the deer mice reaction to the novel fluid item was different in male and female. Magnetic field-exposed female deer mice consumed the same percent of apple juice as sham exposed females ($F_{(1,20)}$=0.32; ns). Conversely sham exposed males consumed a significantly lower percent of apple juice than either the magnetic field exposed males ($F_{(1,19)}$=7,765-, P×0.008) or the magnetic field-exposed females ($F_{(1,19)}$=4.87; P=0.03). However, they did not consume less than sham-exposed females ($F_{(1,19)}$=1.98: ns). FIG. 28 shows that magnetic field exposed mice of both sexes consume a high percent of apple juice (males: 79%, females: 75%). In the sham exposed group only females showed a preference for the apple juice (68%). while males consumed equal quantities of apple juice and tap water (51% of apple juice), suggesting that the magnetic field exposure increased the initial low preference of males for the novel taste.

After being re-tested all mice, that at this stage all displayed a marked preference for the sucrose solution, were then used to examine the effects of a specific pulsed magnetic field an taste preferences. There were three phases in this second experiment. conditioning phase (pairing of the magnetic field with a novel taste; apple juice); post-conditioning phase (sucrose preference) and post-magnetic/sham pairing apple juice preference-determination.

Body weights were not determined as the results of previous experiments had established that the experimental procedures had no significant effect an body weight.

Conditioning Phase: Novel Fluid (Apple Juice) and Magnetic/Sham Field Exposure.

On the morning of the first day water deprived mice were given two drinking tubes both containing pure unsweetened apple juice (McIntosh, Master's Choice, Canada). Apple juice was a novel fluid which in pilot studies deer mice had been shown to readily consume. Apple juice intakes were measured over 90 min. The mice were then immediately placed in the novel holding cage (four mice per time, two males and two females) that was quickly (30 s) moved into the magnetic field apparatus where they were exposed for 60 min. to either the pulsed magnetic or sham field. Each exposure cage was divided in four separate compartments by opaque Plexiglas partitions that prevented the individual mice from seeing each other. Thus four mice per time (2 males and 2 females) were exposed to the same field condition. Mice were assigned to the magnetic/sham exposed groups in a quasi-randomized manner. From each of the LiCl/NaCl groups of experiment 1 half of the males and half of the females were exposed to the magnetic field, while the remaining animals underwent the sham exposure. The order of the exposures were quasi-randomized, with a sham field exposed group following each magnetic field exposure group of 4 mice. The box was washed with hot water and unscented soap between exposures. After being exposed to the magnetic/sham field the mice were returned to their home cages with ad libitum food and water. Water was removed overnight.

Post Conditioning Phase

Percent of Sucrose Intake

On the two days following the magneticlsham field exposure mice were placed an the overnight water deprivation schedules. In the mornings they were presented with two drinking tubes, one containing 0.3 M sucrose and the other tap water. Their intakes were determined for 90 min. after which mice were provided with ad libitum access to tap water.

Post Pairing Percent of Apple Juice Intake

On third day after magnetic/sham field exposure overnight water deprived deer mice were presented with two drinking tubes, one containing water and the other apple juice and their fluid intakes over 90 min. were determined. After this 90 min. period of time the mice were provided with ad libitum access to tap water. The position of the tubes was quasi-randomized: half of the mice in each experimental group (Magnetic/sham field exposed; males/females) had water on the right and the other half had apple juice on the right.

Total fluid intakes across all the experimental days were analyzed by a two way MANOVA, with sex (two levels; males and females) and treatment (two levels; Magnetic and Sham field) as between-subject factors and intake as a repeated-measure within subjects factor (four levels). In order to evaluate the effects of sex and treatment on the fluid intake on each experimental day, mean comparisons were planned a prior-i in the MANOVA model. Since fluid intake displayed a Poissonian distribution the data were square-mot transformed before analysis. As there were some zero intakes, 0.50.was added to all values before transformation.

The sucrose preference data were expressed as the percent of sucrose ingested (arcsin transformed) and were analyzed by a two way MANOVA, with sex (two levels; males and females) and treatment (two levels; Magnetic and Sham field) as between subject factors and percent of sucrose ingested as a repeated-measure within subjects factor (two levels, two days after magnetic/sham field exposure). In order to evaluate the effects of sex and treatment on the sucrose preference on each experimental day, mean comparisons were planned a priori in the MANOVA model.

The apple juice preference data were expressed as percent of apple juice consumed (arcsin transformed) and were analyzed by a two way ANOVA with sex (two levels; males and females) and treatment (two levels; Magnetic and Sham Field) as between subjects and percent of apple juice as the dependent variable. In order to evaluate the effects of sex and treatment on the fluid preference in each experimental day, mean comparisons were planned a priori in the ANOVA model.

Although preferred embodiments have been described herein in detail, it is understood by those skilled in the art that variations and modifications may be made to the present invention without departing from the spirit and scope thereof as defined by the appended claims.

TABLE 1

| | | | | | | | | | | | | | | | | | |
|---|---|---|---|---|---|---|---|---|---|---|---|---|---|---|---|---|---|
| 0 | -53 | -50 | 0 | 96 | 127 | 0 | -92 | -53 | 0 | -128 | 0 | 0 | 0 | -128 | 0 | 0 | 0 |
| 12 | -128 | 0 | 0 | 108 | 72 | 0 | -56 | -53 | 127 | -116 | 0 | 0 | 0 | -116 | 0 | 0 | 0 |
| 24 | -116 | 127 | 0 | 120 | 72 | 0 | 0 | -128 | 72 | -104 | 0 | 0 | 0 | -104 | 0 | 0 | 0 |
| 36 | -92 | 72 | 12 | 127 | -53 | 0 | 0 | -116 | 72 | -50 | 0 | 0 | 0 | -50 | 0 | 0 | 0 |
| 48 | -56 | 72 | 24 | 127 | -53 | 0 | 0 | -92 | -53 | 0 | 12 | 0 | 0 | 0 | 0 | 0 | 0 |
| 60 | 0 | -53 | 36 | -128 | -128 | 0 | 0 | -56 | -53 | 127 | 24 | 0 | 0 | 127 | 12 | 0 | 0 |
| 72 | 0 | -53 | 48 | -116 | -116 | 0 | 0 | 0 | -128 | 72 | 36 | 0 | 0 | 72 | 24 | 0 | 0 |
| 84 | 12 | -128 | 60 | -104 | -92 | 0 | 0 | 0 | -116 | 72 | 48 | 0 | 0 | 72 | 36 | 0 | 0 |
| 96 | 24 | -116 | 72 | -50 | -56 | 0 | 0 | 0 | -92 | -53 | 60 | 0 | 0 | -53 | 48 | 0 | 0 |
| 108 | 36 | -92 | 84 | 0 | 0 | 0 | 0 | 0 | -56 | -53 | 72 | 0 | 0 | -53 | 60 | 0 | 0 |
| 120 | 48 | -56 | 96 | 127 | 0 | 0 | 0 | 0 | 0 | -128 | 84 | 0 | 0 | -128 | 72 | 0 | 0 |
| 127 | 60 | 0 | 108 | 72 | 0 | 0 | 0 | 0 | 0 | -116 | 96 | 0 | 0 | -116 | 84 | 0 | 0 |
| 127 | 72 | 0 | 120 | 72 | 0 | 0 | 0 | 0 | 0 | -92 | 108 | 0 | 0 | -92 | 96 | 0 | 0 |
| -128 | 84 | 12 | 127 | -53 | 0 | 0 | 0 | 0 | 0 | -56 | 120 | 0 | 0 | -56 | 108 | 0 | 0 |
| -116 | 96 | 24 | 127 | -53 | 0 | 0 | 0 | 0 | 0 | 0 | 127 | 0 | 0 | 0 | 120 | 0 | 0 |
| -104 | 108 | 36 | -128 | -128 | 0 | 0 | 0 | 0 | 0 | 0 | 127 | 0 | 0 | 0 | 127 | 0 | 0 |
| -50 | 120 | 48 | -116 | -116 | 0 | 0 | 0 | 0 | 0 | 0 | -128 | 0 | 0 | 0 | 127 | 0 | 0 |
| 0 | 127 | 60 | -104 | -92 | 0 | 0 | 0 | 0 | 0 | 0 | -116 | 0 | 0 | 0 | -128 | 0 | 0 |
| 127 | 127 | 72 | -50 | -56 | 0 | 0 | 0 | 0 | 0 | 0 | -104 | 0 | 0 | 0 | -116 | 0 | 0 |
| 72 | -128 | 84 | 0 | 0 | 0 | 0 | 0 | 0 | 0 | 0 | -50 | 0 | 0 | 0 | -104 | 0 | 0 |
| 72 | -116 | 96 | 127 | 0 | 0 | 0 | 0 | 0 | 0 | 0 | 0 | 0 | 0 | 0 | -50 | 0 | 0 |
| -53 | -104 | 108 | 72 | 0 | 0 | 0 | 0 | 0 | 0 | 0 | 127 | 12 | 0 | 0 | 0 | 0 | 0 |
| -53 | -50 | 120 | 72 | 0 | 0 | 0 | 0 | 0 | 0 | 0 | 72 | 24 | 0 | 0 | 127 | 12 | 0 |
| -128 | 0 | 127 | -53 | 0 | 12 | 0 | 0 | 0 | 0 | 0 | 72 | 36 | 0 | 0 | 72 | 24 | 0 |
| -116 | 127 | 127 | -53 | 0 | 24 | 0 | 0 | 0 | 0 | 0 | -53 | 48 | 0 | 0 | 72 | 36 | 0 |
| -92 | 72 | -128 | -128 | 0 | 36 | 0 | 0 | 0 | 0 | 0 | -53 | 60 | 0 | 0 | -53 | 48 | 0 |
| -56 | 72 | -116 | -116 | 0 | 48 | 12 | 0 | 0 | 0 | 0 | -128 | 72 | 0 | 0 | -53 | 60 | 0 |
| 0 | -53 | -104 | -92 | 0 | 60 | 24 | 0 | 0 | 0 | 0 | -116 | 84 | 0 | 0 | -128 | 72 | 0 |
| 0 | -53 | -50 | -56 | 0 | 72 | 36 | 0 | 0 | 0 | 0 | -92 | 96 | 0 | 0 | -116 | 84 | 0 |
| 12 | -128 | 0 | 0 | 0 | 84 | 48 | 0 | 0 | 0 | 0 | -56 | 108 | 0 | 0 | -92 | 96 | 0 |
| 24 | -116 | 127 | 0 | 0 | 96 | 60 | 12 | 0 | 0 | 0 | 0 | 120 | 0 | 0 | -56 | 108 | 0 |
| 36 | -92 | 72 | 0 | 0 | 108 | 72 | 24 | 0 | 0 | 0 | 0 | 127 | 0 | 0 | 0 | 120 | 0 |
| 48 | -56 | 72 | 0 | 0 | 120 | 84 | 36 | 0 | 0 | 0 | 0 | 127 | 0 | 0 | 0 | 127 | 0 |
| 60 | 0 | -53 | 0 | 12 | 127 | 96 | 48 | 0 | 0 | 0 | 0 | -128 | 0 | 0 | 0 | 127 | 0 |
| 72 | 0 | -53 | 0 | 24 | 127 | 108 | 60 | 12 | 0 | 0 | 0 | -116 | 0 | 0 | 0 | -128 | 0 |
| 84 | 12 | -128 | 0 | 36 | -128 | 120 | 72 | 24 | 0 | 0 | 0 | -104 | 0 | 0 | 0 | -116 | 0 |
| 96 | 24 | -116 | 0 | 48 | -116 | 127 | 84 | 36 | 0 | 0 | 0 | -50 | 0 | 0 | 0 | -104 | 0 |
| 108 | 36 | -92 | 0 | 60 | -104 | 127 | 96 | 48 | 0 | 0 | 0 | 0 | 0 | 0 | 0 | -50 | 0 |
| 120 | 48 | -56 | 0 | 72 | -50 | -128 | 108 | 60 | 12 | 0 | 0 | 127 | 12 | 0 | 0 | 0 | 0 |
| 127 | 60 | 0 | 0 | 84 | 0 | -116 | 120 | 72 | 24 | 0 | 0 | 72 | 24 | 0 | 0 | 127 | 0 |
| 127 | 72 | 0 | 0 | 96 | 127 | -104 | 127 | 84 | 36 | 0 | 0 | 72 | 36 | 0 | 0 | 72 | 0 |
| -128 | 84 | 0 | 0 | 108 | 72 | -50 | 127 | 96 | 48 | 0 | 0 | -53 | 48 | 0 | 0 | 72 | 0 |
| -116 | 96 | 0 | 0 | 120 | 72 | 0 | -128 | 108 | 60 | 0 | 0 | -53 | 60 | 0 | 0 | -53 | 0 |
| -104 | 108 | 0 | 12 | 127 | -53 | 127 | -116 | 120 | 72 | 0 | 0 | -128 | 72 | 0 | 0 | -53 | 0 |
| -50 | 120 | 0 | 24 | 127 | -53 | 72 | -104 | 127 | 84 | 0 | 0 | -116 | 84 | 0 | 0 | -128 | 0 |
| 0 | 127 | 0 | 36 | -128 | -128 | 72 | -50 | 127 | 96 | 0 | 0 | -92 | 96 | 0 | 0 | -116 | 0 |
| 127 | 127 | 0 | 48 | -116 | -116 | -53 | 0 | -128 | 108 | 0 | 0 | -56 | 108 | 0 | 0 | -92 | 0 |
| 72 | -128 | 0 | 60 | -104 | -92 | -53 | 127 | -116 | 120 | 0 | 0 | 0 | 120 | 0 | 0 | -56 | 0 |
| 72 | -116 | 0 | 72 | -50 | -56 | -128 | 72 | -104 | 127 | 0 | 0 | 0 | 127 | 0 | 0 | 0 | 0 |
| -53 | -104 | 0 | 84 | 0 | 0 | -116 | 72 | -50 | 127 | 0 | 0 | 0 | 127 | 0 | 0 | 0 | 0 |

TABLE 2

| Experimental Condition | Response Latency sec ± sem (n) |
|---|---|
| Sham | 4.9 ± 0.2 (45) |
| Acute Cnp | 10.5 ± 0.4 (15) |
| Repeated Cnp | 7.2 ± 0.3 (15) |
| Cnp + vehicle | 9.4 ± 0.3 (48) |
| Cnp + Naloxone | 7.7 ± 0.3 (21) |
| Cnp + 5'-NTII | 7.3 ± 0.3 (22) | sem (Standard Error of the Mean)

REFERENCES

1. Kavaliers, M.; Ossenkopp, K.-P. (1991) Opiold systems and magnetic field effects in the land snail, *Cepaea nemoralis*. Biol. Bull. 180:301–309.
2. Prato, F. S., Ossenkopp, K-P., Kaveliers, M., Sestini, E. A. & Teskey, G. C. (1987) Attenuation of morphine-induced analgesia in mice by exposure to magnetic resonance imaging: Separate effects of the static, radiofrequency and time-varying magnetic fields. *Mag. Res. Irnag.* 5, 9–14.
3. Betancur, C., Dell'Omo, G. and Alleva E., (I 994) Magnetic field effects on stress-induced analgesia in mice: modulation by light, Neurosci. Lett., 182 147–150.
4. Kavaliers, M.; Ossenkopp, K -P.; Prato, F. S.; Carson, J. (1994) Opioid systems and the bilogical effects of magnetic fields. In Frey AH (ed): On the nature of electromagnetic field interactions with biological systems. Austin, RG Landis Co. pp181–190.
5. Del Seppia, C.; Ghione, S.; Luchi, P.; Papi, F. (I 995) Exposure to oscillating magnetic fields influences sensitivity to electrical stimuli. 1: Experiments on pigeons. Bioelectromagnetics 16:290–294.
6. Papi, F.; Ghione, S.; Rosa, C.; Del Seppia, C.; Luschi, P. (1995) Exposure to oscillating magnetic fields influences sensitivity to electrical stimuli. 11: Experiments on humans. Bioelectromegnetics. 16:295–300.
7. Papi, F.; Luschi, P. & Limonta, P. (1991) Orientation-disturbing magnetic treatment affects the pigeon opioid system. *J. exp. Biol.* 160, 169–179.

8. Kavaliers, M., Eckel, L. A. & Ossenkopp, K -P (1993) Brief exposure to 60 Hz magnetic fields improves sexually dimorphic spatial learning performance in themeadow vole, *Microtus pennsvivanicus. J comp. Physiol.* A 173, 241–248.
9. Kavaliers, M., Ossenkopp, K -P., Prato, F. S. et at. (1996) Spatial learning in deer mice: sex differences and the effects of endogenous opioids and 60 Hz magnetic fields. *J comp. Physiol* A (In the press).
10. Polk, C. (1992) Dosimetry of extremely low frequency magnetic fields. *Bioelectrornagnetics Supp.* 1, 209–235.
11. Weaver, J. S. & Astumian, R. D. (1990). The response of living cells to very weak electric fields; the thermal noise limit. *Science, Wash.* 247, 459–462.
12. Kirschvink, J. L. & Walker, M. M. (1985). Particle size considerations for magnetite-based magnetoreceptors. In *Magnetite biomineralisation and magnetoreception in organisms: a new biomagnetism* (ed. J. L. Kirschvink, D. S. Johnes & B. J. MacFadden), pp. 243–256. New York:Plenum Press.
13. Prato, F. S., Kavaliers, M. & Carson, J. J. L.(1996a) Behavioural evidence that magnetic field effects in the land snail, *Cepaea nemoralis,* might not depend on magnetite or induced electric currents. *Bioelectromagnetics* 17, 123–130.
14. Rothman, R. B.(1996) A review of the role of anti-opioid peptides in morphine tolerance and dependence. Synapse. 12:129–136.
15. Kavaliers, M.; Hirst, M. (1983) Tolerance to the morphine-influenced thermal response in the terrestrial snail, *Cepea nemoralis.* Neuropharnacology. 22(11):1321–1326.
16. Thomas, A. W.; Kavaliers, M.; Prato, F. S.; Ossenkopp, K -P. (1997) Antinociceptive effects of a pulsed magnetic field in the land snail, *Cepaea nemoralis.* Neurosci Lett. 222:107–110.
17. Thomas, A. W.; Kavaliers, M.; Prato, F. S.; Ossenkopp, K -P. (in press, 1997) Pulsed magnetic field induced "analgesia" in the land snail, *Cepaea nemoralis,* and the effects of $\mu$, 67, and $\kappa$ opioid receptor agonistslantagonists. Peptides.
18. Thomas, A. W.; Persinger, M. A. (1997) Daily post-training exposure to pulsed magnetic fields that evoke morphine-like analgesia affects consequent motivation but not proficiency in maze learning in rats- Electro- and Magnetobiology. 16(1):33–41.
19. Kavaliers, M.; Hirst, M.; Teskey, G. C. (1983) A functional role for an opioid system in snail thermal behavior. Science. 220:99–101.
20. Kavaliers, M.; Ossenkopp, K.-P. (1985) Tolerance to morphine-induced analgesia in mice: magnetic fields function as environmental specific cues and reduce tolerance development. Life Sci. 37:1125–1135.
21. Tiffany, S. T.; Maude-Griffin, P. M. (1988) Tolerance to morphine in the rat: associative and non-associative effects. Behav. Neurosci. 102:434–443.
22. Tian, J -H.; Xu, W.; Zhang, W.; Fang, Y.; Grisel, J. E.; Mogil, J. S.; Grandy, D. K.; Han, J -S. (1997) Involvement of endogenous Orphanin FQ in electroacupuncture-induced analgesia. Neuroreport. 8:497–500.
23. Tiffany, S. T.; Baker, T. B.(1981) Morphine tolerance in rats: congreunce with a pavlovian paradigm. J Comp. Physiol. Psych. 95:747–762.
24. Baker, T. B.; Tiffany, S. T. (1985) Morphine tolerance as habituation. Psychological Reviews. 92–78–108.
25. Girsel, J. E. G.; Watkins, L. R.; Maier, S. F. (1996) Associative and non-associative mechanisms of morphine analgesia tolerance are neurochemically distinct in the rat spinal cord. Psychopharmacology. 128:245–255.
26. Prato, F. S.; Carson, J. L. L.; Ossenkopp, K.-P; Kavaliers, M. (1995) Possible mechanisms by which extremely low frequency magnetic fields affect opioid function. FASEB. J. 9:807–814.
27. Kits, S. K.; Mansvelder, H. D.(1996) Voltage gated calcium channels in molluscs: classification, $CA^{2-}$ dependent inactivation, modulation and functional roles. Invertebrate Neuroscience. 2:9–34.
28. Prato, F. S.; Kavaliers, M.; Carson, J. L. L. (1996) Behavioral evidence that magnetic field effects in the land snail, *Cepaea nemoralis.* might not depend on magnetite or induced electric currents. Bioelectromagnetics. 1 7:123–130.
29. Smith, K. H., Jr. (1987) Quantified aspects of pallial fluid and its affect on the duration of locomotor activity in the terrestrial gastropod Triolopsis albolabaris. Physiol. Zool. 54:407–414.
30. Dyakonova, V.; Elofsson, R.; Carlberg, M.; Sakharov, D.(1995) Complex avoidance behavior and its neurochemical regulation in the land snail, *Cepaea nemoralis.* Gen. Pharmacol. 26:773–777.
31. Michon A, Koren S A, Persinger M A (1996): *Perceptual and Motor Skills* 82:619–626.
32. Baker-Price L. A. and M. A. Persinger, (1996) Weak, but complex pulsed magnetic fields may reduce depression following traumatic brain injury. *Perceptual and Motor Skills,* 83, 491498.
33. M. Kaveliers, K.-P. Ossenkopp, F. S. Prato, D. G. L. Innes, L. A. M. Galea, D. M. Kinsella, T. S. Perrot-Sinal, (1996) Spatial learning in deer mice: sex differences and the effects of endogenous opioids and 60 Hz Magnetic fields. J. Com. Physio A 179.

What is claimed is:

1. A method for treating a disorder selected from the group of physiological, neurological and behavioral disorders, said method comprising applying to a subject a specific low frequency pulsed magnetic field (Cnp) having a plurality of intermittent waveforms, for a time effective to produce a desired effect in a target tissue, wherein said Cnp initially entrains the electrical activity of the target issue and as a result affects the endogenous electrical activity of said target tissue.

2. The method of claim 1, wherein said plurality of waveforms are configured with length and frequency relative to the target tissue.

3. The method of claim 2, wherein said waveforms are configured to mimic generally the underlying electrical activity of the target tissue.

4. The method of claim 2, wherein said plurality of waveforms have a built-in variable latency period.

5. The method of claim 1, wherein said low frequency pulsed magnetic field (Cnp) is designed with a built in delay to reduce excitation in said target tissue.

6. The method of claim 4, wherein said latency period is progressively lengthened to reduce the burst firing rate of endogenous electrical activity of said target tissue.

7. The method of claim 4, wherein said latency period is moderated differently in sequential waveforms to simultaneously target a number of different tissues.

8. The method of claim 1 wherein said low frequency pulsed magnetic field has a fixed refractory period relative to said target tissue.

9. The method of claim 1, wherein said method is used to treat disorders selected from the group consisting of pain, anxiety, balance, learning, taste aversion, epilepsy and depression.

10. The method of claim 1, wherein said Cnp used in the method is selected from the Cnps of FIG. 1, FIG. 3 or FIG. 5.

11. The method of claim 1 wherein the frequency and length of said waveforms vary over time.

12. A method for treating a disorder selected from the group of physiological, neurological and behavioral disorders, said method comprising applying to a subject a specific low frequency pulsed magnetic field (Cnp) having a plurality of intermittent waveforms, for a time effective to produce a desired effect in a target tissue and wherein the frequency of said waveforms decrease over time.

13. The method of claim 1 wherein the frequency of said waveforms increase or decrease over time.

14. The method of claim 1 wherein said waveforms have fast rise times and are configured to stimulate firing of axons in said target tissue.

15. The method of claim 1 wherein said waveforms define variable latency periods, said latency periods being selected to reduce the probability of neural excitement as the waveforms end.

16. The method of claim 1, wherein said waveforms have amplitudes and DC offsets selected in relation to the target tissue.

17. The method of claim 1, wherein said low frequency pulsed magnetic field (Cnp) is designed with a built in delay to reduce excitation in said target tissue.

18. The method of claim 1, wherein a static magnetic field offset is applied to said target tissue.

19. The method of claim 1, wherein said method additionally comprises simultaneously applying a specific low frequency non-magnetic pulsed field to said target tissue, said specific low frequency non-magnetic pulsed field being selected from the group consisting of light, electrical fields, acoustic waves and peripheral stimulation of nerve receptors.

20. A method of treating physiological, neurological and behavioral disorders comprising the step of subjecting target tissue to intermittent specific time varying low frequency magnetic fields for a duration effective to produce a desired effect, said intermittent magnetic fields being separated by refractory periods, and wherein said intermittent magnetic fields initially entrain the electrical activity of said target issue and as a result affect the endogenous electrical activity of said target tissue.

21. The method of claim 20, wherein said waveforms are configured to mimic generally the underlying electrical activity of the target tissue.

22. The method of claim 20 wherein the frequency and length of said waveforms vary over time.

23. The method of claim 20 wherein the frequency of said waveforms increase or decrease over time.

24. The method of claim 20, wherein said refractory periods are fixed at a duration relative to the target tissue.

25. The method of claim 20, wherein said waveforms have fast rise times and are configured to stimulate firing of axons in the target tissue.

26. The method of claim 20 wherein said wavefonns define variable latency periods, said latency periods being selected to reduce the probability of neural excitement as the waveforms end.

27. The method of claim 20, wherein said waveforms have amplitudes and DC offsets selected in relation to the target tissue.

28. A method of treating physiological, neurological and behavioral disorders comprising the step of subjecting target tissue to intermittent specific time varying low frequency magnetic fields for a duration effective to produce a desired effect, said intermittent magnetic fields being separated by refractory periods and having waveforms configured relative to the target tissue and wherein the frequency of said waveforms decrease over time.

* * * * *

UNITED STATES PATENT AND TRADEMARK OFFICE
CERTIFICATE OF CORRECTION

PATENT NO. : 6,234,953 B1  
DATED : May 22, 2001  
INVENTOR(S) : Thomas et al.

It is certified that error appears in the above-identified patent and that said Letters Patent is hereby corrected as shown below:

Column 30,  
Lines 59-61, cancel Claim 5 in its entirety and insert original Claim 26 from the specification as Claim 5 as follows:  
-- 5. The method of claim 4, wherein said latency period is progressively shortened to increase the burst firing rate of endogenous electrical activity of said target issue. --.

Signed and Sealed this

Twelfth Day of November, 2002

*Attest:*

JAMES E. ROGAN  
*Attesting Officer* *Director of the United States Patent and Trademark Office*

UNITED STATES PATENT AND TRADEMARK OFFICE
CERTIFICATE OF CORRECTION

PATENT NO. : 6,234,953 B1
DATED : May 22, 2001
INVENTOR(S) : Alex W. Thomas et al.

It is certified that error appears in the above-identified patent and that said Letters Patent is hereby corrected as shown below:

Title page,
Item [56], References Cited, U.S. PATENT DOCUMENTS, add the following:
-- 3,678,337    7/1972    Grauvogel    [ ] --.
FOREIGN PATENT DOCUMENTS, add the following:
-- GB 2,270,000    3/1994    Grace et al.    [ ] --; and add the following:

-- OTHER PUBLICATIONS

Kirschvink and Walker, " Particle-Size Considerations for Magnetite-Based Magnetoreceptors," Contribution No. 4135 from *The Division of Geological and Planetary Sciences*, California Institute of Technology, pp. 243-256, 1985.

Kavaliers, et al., "Opiod Systems and Magnetic Field Effects in the Land Snail, *Cepaea Nemoralis*," *Biol. Bull.*, 180: 301-309, April, 1991.

Prato, et al., "Attenuation of Morphine-Induced Analgesia in Mice by Exposure to Magnetic Resonance Imaging: Separate Effects of the Static, Radiofrequency and Time-Varying Magnetic Fields," *Magnetic Resonance Imaging*, Vol. 5, pp. 9-14, 1987.

Betancur, et al., "Magnetic Field Effects on Stress-Induced Analgesia in Mice: Modulation by Light," *Neuroscience Letters* 182 (1994) 147-150.

Kavaliers, et al., "Opioid Systems and the Biological Effects of Magnetic Fields," *On The Nature of Electromagnetic Field Interactions with Biological Systems*, pp. 181-194, 1994.

Del Seppia, et al., "Exposure to Oscillating Magnetic Fields Influences Sensitivity to Electrical Stimuli. I. Experiments on Pigeons," *Bioelectromagnetics*, 16:290-294 (1995).

Papi, et al., "Exposure to Oscillating Magnetic Fields Influences Sensitivity to Electrical Stimuli. II. Experiments on Humans," *Bioelectromagnetics*, 16:295-300 (1995).

Papi et al., "Orientation-Disturbing Magnetic Treatment Affects the Pigeon Opiod System," *J. EXP BIOL.*, 166, 169-179 (1992).

Polk, "Dosimetry of Extremely Low Frequency Magnetic Fields," *Bioelectromagnetics Supplement*, 1:209-235 (1992).

UNITED STATES PATENT AND TRADEMARK OFFICE
CERTIFICATE OF CORRECTION

PATENT NO. : 6,234,953 B1
DATED : May 22, 2001
INVENTOR(S) : Alex W. Thomas et al.

It is certified that error appears in the above-identified patent and that said Letters Patent is hereby corrected as shown below:

Title page (cont'd),

Weaver et al., "The Response of Living Cells to Very Weak Electric Fields: The Thermal Noise Limit," *Science Reports*, Vol. 247, pp. 459-462, 26 January 1990.

Kavaliers, et al., "Brief Exposure to 60 HZ Magnetic Fields Improves Sexually Dimorphic Spatial Learning Performance in the Meadow Vole, Microtus Pennsylvanicus," *Journal of Comparative Physiology A*, 173: 241-248, 1993.

Kavaliers, et al., "Spatial Learning in Deer Mice: Sex Differences and the Effects of Endogenous Opiods and 60 HZ Magnetic Fields," *Journal of Comparative Physiology A*, 179:1-10, 1996.

Prato, et al., "Behavioural Evidence that Magnetic Field Effects in the Land Snail, *Cepaea Nemoralix*, Migh Not Depend on Magnetite or Induced Electric Currents," *Bioelectromagnetics*, 17:123-130 (1996).

Column 30,
Line 48, delete the word "issue" and insert -- "tissue" --.

Signed and Sealed this

First Day of November, 2005

JON W. DUDAS
*Director of the United States Patent and Trademark Office*

(12) EX PARTE REEXAMINATION CERTIFICATE (5725th)
United States Patent
Thomas et al.

(10) Number: US 6,234,953 C1
(45) Certificate Issued: Mar. 27, 2007

(54) ELECTROTHERAPY DEVICE USING LOW FREQUENCY MAGNETIC PULSES

(75) Inventors: Alex W. Thomas, London (CA); Frank S. Prato, London (CA); Martin I. Kavaliers, London (CA); Michael A. Persinger, Sudbury (CA)

(73) Assignee: The Lawson Research Institute, London (CA)

Reexamination Request:
No. 90/007,621, Jul. 5, 2005

Reexamination Certificate for:
Patent No.: 6,234,953
Issued: May 22, 2001
Appl. No.: 09/194,930
Filed: Jan. 20, 1999

Certificate of Correction issued Nov. 12, 2002.

Certificate of Correction issued Nov. 1, 2005.

(22) PCT Filed: Jun. 5, 1997

(86) PCT No.: PCT/CA97/00388

§ 371 (c)(1),
(2), (4) Date: Jan. 20, 1999

(87) PCT Pub. No.: WO97/46277

PCT Pub. Date: Dec. 11, 1997

Related U.S. Application Data

(60) Provisional application No. 60/019,184, filed on Jun. 6, 1996.

(51) Int. Cl.
*A61N 2/02* (2006.01)
*A61N 2/00* (2006.01)

(52) U.S. Cl. ........................................................ 600/14
(58) Field of Classification Search ................ None
See application file for complete search history.

(56) References Cited

U.S. PATENT DOCUMENTS

| | | | |
|---|---|---|---|
| 3,678,337 A | | 7/1972 | Grauvogel |
| 4,583,545 A | | 4/1986 | Towe |
| 4,825,877 A | | 5/1989 | Kempe |
| 5,066,272 A | | 11/1991 | Eaton et al. |
| 5,084,003 A | | 1/1992 | Susic |
| 5,342,410 A | * | 8/1994 | Braverman ............... 600/26 |
| 5,527,259 A | | 6/1996 | Grace et al. |
| 5,621,188 A | | 4/1997 | Lee et al. |
| 5,634,939 A | | 6/1997 | Kuster et al. |
| 5,690,109 A | | 11/1997 | Govind et al. |
| 5,725,471 A | | 3/1998 | Davey et al. |
| 5,807,272 A | | 9/1998 | Kun et al. |
| 5,833,600 A | | 11/1998 | Young |
| 5,935,054 A | * | 8/1999 | Loos ........................ 600/9 |
| 6,128,522 A | | 10/2000 | Acker et al. |
| 2003/0181791 A1 | | 9/2003 | Thomas et al. |
| 2003/0217754 A1 | | 11/2003 | Thomas et al. |

FOREIGN PATENT DOCUMENTS

| | | |
|---|---|---|
| DE | 33 31 976 | 3/1985 |
| DE | 39 38 920 | 5/1991 |
| FR | 2 533 131 | 3/1984 |
| GB | 2025237 | 1/1980 |
| GB | 2 270 000 | 3/1994 |
| WO | WO 96/11723 | 4/1996 |

OTHER PUBLICATIONS

Betancur, C, Dell'Omo, G and Alleva, E (1994): Magnetic field effects on stress–induced analgesia in mice: modulation by light. Neurosci. Lett 182:147–150.

(Continued)

*Primary Examiner*—Peter C. English

(57) ABSTRACT

An apparatus and method for treating a disorder selected from the group of physiological, neurological and behavioral disorders, the method comprising applying to a subject a specific low frequency pulsed magnetic field (Cnp) having a plurality of intermittent waveforms, for a time effective to produce a desired effect in a target tissue.

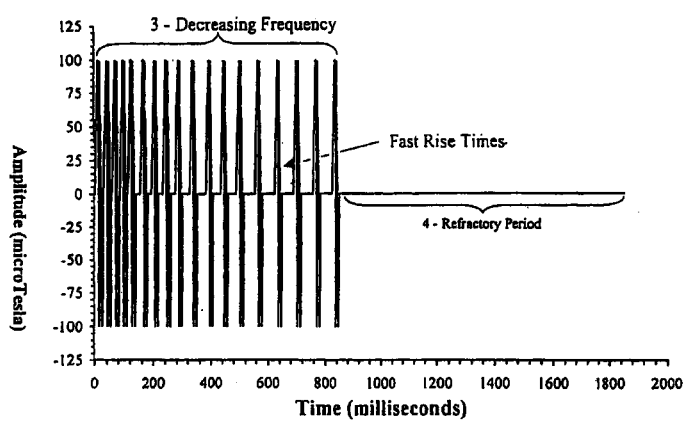

OTHER PUBLICATIONS

Kavaliers, M, Ossenkopp, K–P, Prato, FS and Carson, J (1994): Opioid systems and the biological effects of magnetic fields. In Frey, AH (ed): On the Nature of Electromagnetic Field Interactions with Biological Systems. Austin, RG Landis Co. 181–190.

Del Seppia, C, Ghione, S, Luchi, P and Papi, F(1995): Exposure to oscillating magnetic fields influences sensitivity to electrical stimuli. I. Experiments on pigeons. Bioelectromagnetics 16:290–294.

Papi, F, Ghione, S, Rosa, C, Del Seppia, C and Luschi, P (1995): Exposure to oscillating magnetic fields influences sensitivity to electrical stimuli. II: Experiments on humans. Bioelectromagnetics 16:295–300.

Papi, F, Luschi, P and Limonta, P (1992): Orientation–disturbing magnetic treatment affects the pigeon opioid system. J exp Biol 160:169–179.

Kavaliers, M, Eckel, LA and Ossenkopp, K–P (1993): Brief exposure to 60 Hz magnetic fields improves sexually dimorphic spatial learning performance in the meadow vole, *Microtus pennsylvanicus*. J Comp Physiol, A 173: 241–248.

Polk, C (1992): Dosimetry of extremely low frequency magnetic fields. Bioelectromagnetics Sup 1: 209–235.

Kirschvink, JL and Walker, MM (1985): Partial size considerations for magnetite–based magnetoreceptors, in Magnetite Biomineralisation and Magnetoreception in Organisms: A New Biomagnetism. Contribution No. 4135 from the Division of Geological and Planetary Sciences, California Institute of Technology.

Prato, FS, Kavaliers, M and Carson, JJL (1996): Behavioural evidence that magnetic field effects in the land snail, *Cepaea nemoralis*, might not depend on magnetite or induced electric currents. Bioelectromagnetics 17: 123–130.

Rothman, RB (1996): A review of the role of anti–opioid peptides in morphine tolerance and dependence. Synapse 12:129–136.

Kabaliers, M and Hirst, M (1983): Tolerance to the morphine–influenced thermal response in the terrestrial snail, *Cepea nemoralis*. Neuropharmacology 22(11):1321–1326.

Thomas, AW, Kavaliers, M, Prato, FS, Ossenkopp, K–P (1997): Antinociceptive effects of a pulsed magnetic field in the land snail, *Cepaea nemoralis*. Neurosci Lett 222:107–110.

Thomas, AW, Kavaliers, M, Prato, FS and Ossenkopp, K–P (in press, 1997): Pulsed magnetic field induced "analgesia" in the land snail, *Cepaea nemoralis*, and the effects of µ, 67 and κ opioid receptor agonists/antagonists. Peptides.

Thomas, AW, Persinger, MA (1997): Daily post–training exposure to pulsed magnetic fields that evoke morphine–like analgesia affects consequent motivation but not proficiency in maze learning in rats. Electro– and Magnetobiology 16(1):33:41.

Kavaliers, M, Hirst, M and Teskey. GC (1983): A functional role for an opioid system in snail thermal behavior. Science 220:99–101.

Kavaliers, M and Ossenkopp, K–P (1985): Tolerance to morphine–induced analgesia in mice: magnetic fields functions as environmental specific cues and reduce tolerance development. Life Sci 37:1125–1135.

Tiffany, ST and Maude–Griffin, PM (1988): Tolerance to morphine in the rat: associative and non–associative effects. Behav Neurosci 102:434–443.

Tian, JH, Xu, W, Zhang, W, Fang, Y, Grisel, JE, Mogil, JS, Grandy, DK and Han, JS (1997): Involvement of endogenous Orphanin FQ in electroacupuncture–induced analgesia, Neuroreport 8:497–500.

Tiffany, ST and Baker, TB (1981): Morphine tolerance in rats: congruence with a Paviovian paradigm. J Comp. Physiol. Phych 95:747–762.

Baker, TB and Tiffany, ST (1985): Morphine tolerance as habituation. Psychological Reviews 92:72–108.

Girsel, JEG, Watkins, LR and Maier, SF (1996): Associative and non–associative mechanisms of morphine analgesia tolerance are neurochemically distinct in the rat spinal cord. Psychopharmacology 128:245–255.

Prato, FS, Carson, JLL, Ossenkopp, K–P and Kavaliers, M (1995): Possible mechanisms by which extremely low frequency magnetic fields affect opioid function. FASEB J 9:807–814.

Kits, SK and Mansvelder, HD (1996): Voltage gated calcium channels in molluscs: classification, $CA^{2-}$ dependent inactivation, modulation and functional roles. Invertebrate Neuroscience 2:9–34.

Smith, KH, Jr. (1987): Quantified aspects of pallial fluid and its effect on the duration of locomotor activity in the terrestrial gastropod *Triolopsis albolabaris*. Physiol Zool 54:407–414.

Dyakonova, V, Elofsson, R, Carlberg, M and Sakharov, D (1995): Complex avoidance behavior and its neurochemical regulation in the land snail, *Cepaea nemoralis*. Gen Pharmacol 26:773–777.

Michon, A, Koren, SA and Persinger, MA (1996): Perceptual and Motor Skills 82:619–626.

Baker–Price, LA and Persinger, MA (1996): Weak, but complex pulsed magnetic fields may reduce depression following traumatic brain injury. Perceptual and Motor Skills 83:491–498.

Bassett, CAL, Mitchell, SN and Gaston, SR (1981): Treatment of ununited tibial diaphyseal fractures with pulsing electromagnetic fields. J Bone Joint Surg Apr/81, v63–A:4:511–523.

Beckers, G and Homberg, V (1991): Impairment of visual perception and visual short term memory scanning by transcranial magnetic stimulation of occipital cortex, Exp Brain Res 87:421–432.

Bell, GB, Marino, AA and Chesson, AL (1992): Alterations in brain electrical activity caused by magnetic fields: Detecting the detection process. Electroenceph Clin Neurophysiol 83:389–397.

Bell, GB, Marino, AA and Chesson, AL (1994): Frequency–specific blocking in the human brain caused by electromagnetic fields. NeuroReport 5:510–512.

Bell, GB, Marino, A, Chesson, A and Struve, F (1992): Electrical states in the rabbit brain can be altered by light and electromagnetic fields. Brain Res 570:307–315.

Canady, DJ and Lee, RC (1991): Scientific basis for clinical applications of electric fields in soft tissue repair, in Electromagnetics in Medicine and Biology, Brighton, C T and Pollack, SR (eds.). San Francisco: San Francisco: San Francisco Press, 275–280.

Carson, JJL, Prato, FS, Drost, DJ, Diesbourg, LD and Dixon, SJ (1990): Time–varying magnetic fields increase cytosolic free $Ca^2$ in H–60 cells. Am J Physiol Soc 259 (Cell Physiol 28): C687–C692.

Fleischmann, A, Prolov, K, Abarbanel, J and Belmaker, RH (1995): The effect of transcranial magnetic stimulation of rat brain on behavioral models of depression. Brain Res 699:130–132.

Frey, A.H. (ed.) (1994): On the Nature of Electromagnetic Field Interactions with Biological Systems, R.G. Landes Co., Austin, Texas.

Fuller, M, Dobson, J, Wieser, HG and Moser, S (1995): On the sensitivity of the human brain to magnetic fields: Evocation of epileptiform activity, Brain Res Bull 36:155–169.

Grisaru, N, Yaroslavsky, U, Abarbanel, J, Lambert, T and Belmaker, RH (1994): Transcranial magnetic stimulation in depression and schizophrenia. Eur Neuropsychopharmacol 4:287–288.

Holden, C (1995): Substitute for shock Therapy? Science 1/Dec, 270, 5241:1443.

Ito, H and Bassett, CAL (1983): Effect of weak, pulsing electromagnetic fields on neural regeneration in the rat. Clin Orthopaed 181:283–290.

Kavaliers, M and Ossenkopp, K–P (1985): Exposure to rotating magnetic fields alters morphine–induced behavioral response in two strains of mice. Neuropharmacol 24:4:337–340.

Kavaliers, M and Ossenkopp, K–P (1986): Magnetic fields differentially inhibit, mu, delta, kappa and sigma opiate–induced analgesia in mice. Peptides 7: 449–453.

Kavaliers, M and Ossenkopp, K–P (1986b): Stress–induced opioid analgaesia and activity in mice: Inhibitory influences of exposure to magnetic fields. Psychopharmacol 89:440–443.

Kavaliers, M and Ossenkopp, K–P (1986): Magnetic field inhibition of morphine–induced analgesia and behavioral activity in mice: Evidence for involvement of calcium ions. Brain Res 379:30–38.

Kavaliers, M and Ossenkopp, K–P (1987): Calcium channel involvement in magnetic field inhibition of morphine–induced analgesia. Naunyn–Schmiedeberg's Arch Pharmacol 336:308–315.

Kavaliers, M and Ossenkopp, K–P (1988): Magnetic fields inhibit opioid–mediated "analgesic" behaviours of the terrestrial snail, Cepaea nemoralis. J Comp Physiol A 162:551–558.

Kavaliers, M and Ossenkopp, K–P (1993): Repeated naloxone treatments and exposure to weak 60–Hz magnetic fields have "analgesic" effects in snails. Brain Res 620:159–162.

Kavaliers, M and Ossenkopp, K–P and Hirst, M (1984): Magnetic fields abolish the enhanced nocturnal analgesic response to morphine in mice. Physiol Behav 32:261–264.

Kavaliers, M and Ossenkopp, K–P and Tysdale, DM (1991): Evidence for the involvement of protein kinase C in the modulation of morphine–induced "analgesia" and the inhibitory effects of exposure to 60–Hz magnetic fields in the snail, Cepaea nemoralis. Brain Res 554: 65–71.

Kwong–Hing, A, Sandhu, HS, Prato, FS, Frappier, JRH and Kavaliers, M (1989): Effects of magnetic resonance imaging (MRI) on the formulation of mouse dentin and bone. J Exper Zool 252:53–59.

Lerchl, A, Honaka, KO and Reiter, RJ (1991): Pineal gland "magnetosensitivity" to static magnetic fields is a consequence of induced electric currents (eddy currents). J Pineal Res 10:109–116.

Lindstrom, E, Lindstrom, P, Berglund, A, Mild, KH and Lundgren, E (1993): Intracellular calcium oscillations induced in a T–cell line by a weak 50 Hz magnetic field. J Cell Physiol 156:395–398.

Lohmann, KJ and Willows, AOD (1991): An identifiable molluscan neuron responds to changes in earth–strength magnetic fields. J exp Biol 161:1–24.

Lyskov, E, Juutilainen, J, Jousmaki, V, Hänninen, O, Medvedev, S and Partamen, J (1993): Influence of short–term exposure of magnetic field on the bioelectrical processes of the brain and performance. Intern J Psychophysiol 14:227–231.

Mather, JG and Baker, RR (1981): Magnetic sense of direction in woodmice for route–based navigation. Nature 291:152–155.

Ossenkopp, K–P and Kavaliers, M (1987): Morphine–induced analgesia and exposure to low–intensity 60–Hz magnetic fields: Inhibition of noctural analgesia in mice is a function of magnetic field intensity. Brain Res 418:356–360.

Ossenkopp, K–P and Cain, DP (1988): Inhibitory effects of acute exposure to low–intensity 60–Hz magnetic fields on electrically kindled seizures in rats. Brain Res 442:255–260.

Papi, F, Ghione, Rosa, C, Del Seppia, C and Luschi, P (1995): Exposure to oscillating magnetic fields influences sensitivity to electrical stimula. II. Experiments on humans. Bioelectromagnetics 16: 295–300.

Winston, C, Parris, V, Janicki, PK, Johnson, BW, Jr., and Matthews, L (1994): The behavioral and biochemical effect of pulsating magnetic field treatment (PMFT) on chronic pain produced by chronic constriction injury of sciatic nerve in rat. Analgesia 1:1:57–64.

Pascual–Leone, A, Valls–solé, J, Brasil–NETOo, JP Cammarota, A, Grafman, J and Hallet, M (1994): Akinesia in Parkinson's Disease. II. Effects of subthreshold repetitive transcranial motor cortex stimulation. Neurology 44:892–898.

Phillips, JB and Borland, SC (1992): Behavioural evidence for the use of a light–dependent magnetoreception mechanisms by a vertebrate. Nature 359:142–144.

Phillips, JB and Sayeed, O (1993): Wavelength–dependent effects of light on magnetic compass orientation in Drosophila melanogaster. J Comp Physiol A 172: 303–308.

Prato, FS, Frappier, JRH, Shivers, RR, Kavaliers, M, Zabel, P, Drost, D and Lee, T–Y (1990): Magnetic resonance imaging increases the blood–brain barrier permeability to 153–gadolinium diethylenetriaminepentaacetic acid in rats, Brain Res 523:301–304.

Prato, FS, Wills, JM, Frappier, JRH, Drost, DJ, Lee, T–Y, Shivers, RR and Zabel, P (1994): Blood–brain barrier permeability in rats is altered by exposure to magnetic fields associated with magnetic resonance imaging at 1.5T. Microscopy Research and Technique 27:528–534.

Reiter, RJ (1992): Alterations of the circadian melatonin rhythm by the electromagnetic spectrum: A study in environmental toxicology. Reg Toxicol Pharmacol 15:226–244.

Reiter, RJ and Richardson, BA (1992): Magnetic field effects on pineal indoleamine metabolism and possible biological consequences, FASEB J 6:2283–2287.

Schneider, T, Thalau, H–P and Semm, P (1994): Effects of light or different earth–strength magnetic fields on the nocturnal melatonin concentration in a migratory bird. Neurosci Lett 168:73–75.

Selmaoui, B and Touitou, Y (1995): Sinusoidal 50Hz magnetic fields depress rat pineal NAT activity and serum melatonin: Role of duration and intensity of exposure. Life Sci 57:14:1351–1358.

Semm, P and Beason, RC (1990): Responses to small magnetic variations by the trigeminal system of the bobolink. Brain Res Bull 25:735–740.

Semm, P, Schneider, T and Vollrath, L (1980): Effects of an earth–strength magnetic field on electrical activity of pineal cells. Nature 288:607–608.

Shivers, RR, Kavaliers, M, Teskey, GC, Prato, FS and Pelletier, R–M (1987): Magnetic resonance imaging temporarily alters blood–brain barrier permeability in the rat. Neurosci Lett 76:25–31.

Sisken, BF, Kanje, J, Lundborg, G and Kurtz, W (1990): Pulsed electromagnetic fields stimulate nerve regeneration *in vitro* and *in vivo*. Restor Neurol Neurosci 1:303–309.

Steffensen, B, Caffesse, RG, Hanks, CT, Avery, JK and Wright, N (1988): Clinical effects of electromagnetic stimulation as an adjunct to periodontal therapy. J Periodontol Jan/88 59:1:46–52.

Teskey, GC, Prato, FS, Ossenkopp, K–P and Kavaliers, M (1988): Exposure to time varying magnetic fields associated with magnetic resonance imaging reduces fentanyl–induced analgesia in mice. Bioelectromagnetics 9:2:167–174.

Thomas, AW, Kavaliers, M and Prato, FS (1996): Antinociception ("analgesia") induced by weak extremely low frequency complex neuroelectro–magnetic pulses. Bioelectromagnetics Soc Abstracts 18, in press.

Thomas, AW, Kavaliers, M and Prato, FS (1996): Development of tolerance to the opioid–mediated antinociceptive effects of weak extremely low frequency complex neuroelectromagnetic pulses. Bioelectromagnetics Soc Abstracts 18, in press.

Walleczek, J (1992): Electromagnetic field effects on cells of the immune system: The role of calcium signalling, FASEB J 6:3177–3185.

Walleczek, J and Liburdy, RP (1990): Nonthermal 60 Hz sinusoidal magnetic–field exposure enhances $^{45}Ca^{2+}$ uptake in rat thymocytes: dependence on mitogen activation: FEBS 271:1,2:157–160.

Zyss, T (1994): Deep magnetic brain stimulation—The end of psychiatric electroshock therarpy? Medical Hypotheses 43: 69–74.

Lednev, VV, Srebnitskaya, LK, YE, N, Il'Yasova, Z, Rozhdestvenskaya, Y, Klimov, AA, Belova, NA and Tiras, KP (1997): Magnetic parametic resonance in biosystems: experimental verification of the predictions of a theory using regenerating planarians, *Dugesia tigrina,* as a test system. Biophysics 41:825–835.

McLeod, KJ, Lee, RC and Ehrlich, HP (1987): Frequency dependence of electric field modulation of fibroblast synthesis. Science 236:1465–1469.

Barker, AT, Freeson, IL, Jalinous, R and Jarratt, JA (1987): Magnetic stimulation of the human brain and peripheral nervous system: an introduction and the results of initial clinical evaluation. Neurosurgery 20:100–109.

Persinger, MA, Koren, SA, Makarec, K, Richards, P and Youlton, S (1991): Differential effects of wave form and the subject's possible temporal lobe signs upon experience during cerebral exposure to weak intensity magnetic fields. J Bioelectricity 10(1&2):141–184.

Richards, PM, Persinger, MA and Koren, SA (1993): Modification of activation and evaluation properties of narratives by weak complex magnetic field patterns that simulate limbic burst firing. Intern J Neurosci 71:71–85.

Gillis, C and Persinger, MA (1993): Shifts in the Plutchik emotion profile indices following three weekly treatments with pulsed vs continuous cerebral magnetic fields. Perceptual and Motor Skills 76:168–170.

Tiller, SG and Persinger, MA (1994): Enhanced hypnotizability by cerebrally applied magnetic fields depends upon the order of hemispheric presentation: An anisotropic effect. Intern J Neurosci 79:157–163.

Persinger, MA, Richards, PM and Koren, SA (1994): Differential ratings of pleasantness following right and left hemispheric application of low energy magnetic fields that stimulate long–term potentiation. Intern J Neurosci 79:191–197.

Bureau, YRJ and Persinger, MA (1995): Decreased Incidence of limbic motor seizures following twenty pairings f subclinical lithium–pilocarpine injections and a complex "burst–firing" magnetic field. Electro– and Magnetobiology 14(1):1–6.

Persinger, MA, Ludwig, HW and Ossenkopp, K–P (1973): Psychophysiological effects of extremely low frequency electromagnetic fields: a review. Perceptual and Motor Skills, Monograph Supplement 3–V36. 36:1131–1159.

Persinger, MA (1988): The Modern Magnetotherapies, In Marino, AA (ed.) Modern Bioelectricity, NY, Dekker:589–627.

Persinger, MA (1995): On the possibility of directly accessing every human brain by electromagnetic induction of fundamental algorithms. Perceptual and Motor Skills 80:791–799.

Adey, WR (1973): The influences of impressed electrical fields at EEG frequencies on brain and behavior. Behavior and Brain Electrical Activity, BURCH, [ ] and ALSHULER, [ ], eds., NY, Plenum: 363:390.

Fleming, JL, Persinger, MA and Koren, SA (1994): Magnetic pulses elevate nociceptive thresholds: comparisons with oplate receptor compounds in normal and seizure–induced brain–damaged rats. Electro– and magnetobiology 13(1):67–75.

Kirschvink and Walker, "Particle–Size Considerations for Magnetite–Based Magnetoreceptors", *Contribution No. 4135 From the Division of Geological and Planetary Sciences, California Institute of Technology,* pp. 243–256, 1985.

Kavaliers, et al., "Opioid Systems and Magnetic Field Effects in the Land Snail, *Cepaea Nemoralis*", *Biol Bull,* 180:301–309, Apr. 1991.

Prato, et al., "Attenuation of Morphine–Induced Analgesia in Mice by Exposure to Magnetic Resonance Imaging: Separate Effects of the Static, Radiofrequency and Time–Varying Magnetic Fields", *Magnetic Resonance Imaging,* vol. 5, pp. 9–14, 1987.

Kavaliers, et al., "Opioid Systems and the Biological Effects of Magnetic Fields", *On the Nature of Electromagnetic Field Interactions With Biological Systems,* pp. 181–194, 1994.

Papi, et al., "Orientation–Disturbing Magnetic Treatment Affects the Pigeon Opioid System", *J. Exp Biol.*, 166. 169–179 (1992).

Weaver, et al., "The Response of Living Cells to Very Weak Electric Fields: The Thermal Noise Limit", *Science Reports*, vol. 247, pp. 459–462, Jan. 26, 1990.

Kavaliers, et al., "Spatial Learning in Deer Mice: Sex Differences and the Effects of Endogenous Opioids and 60 Hz Magnetic Fields", , *Journal of Comparative Physiology A*, 179:1–10, 1996.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3, 4, 17 and 21 are cancelled.

Claims 1, 5–7, 10, 12, 13, 15, 20, 23, 26 and 28 are determined to be patentable as amended.

Claims 2, 8, 9, 11, 14, 16, 18, 19, 22, 24, 25 and 27, dependent on an amended claim, are determined to be patentable.

New claims 29–34 are added and determined to be patentable.

1. A method for treating a disorder selected from the group of physiological, neurological and behavioral disorders, said method comprising applying to a subject a specific low frequency pulsed magnetic field [(Cnp)], *each pulse having a plurality of intermittent waveforms, said waveforms being designed to initially mimic an endogenous electrical activity of target tissue of said subject, and to have a latency period between waveforms that varies in a predetermined manner over time, the application of said low frequency pulsed magnetic field being for a time effective to* produce a desired effect in [a] *said* target tissue, wherein said [Cnp] *low frequency pulsed magnetic field* initially entrains the electrical activity of the target tissue and as a result affects the endogenous electrical activity of said target tissue.

5. The method of claim [4] *1*, wherein said latency period is progressively shortened to increase the burst firing rate of endogenous electrical activity of said target tissue.

6. The method of claim [4] *1*, wherein said latency period is progressively lengthened to reduce the burst firing rate of endogenous electrical activity of said target tissue.

7. The method of claim [4] *1*, wherein said latency period is [moderated] *varied* differently in sequential waveforms to simultaneously target a number of different tissues.

10. The method of claim 1, wherein said [Cnp] *low frequency pulsed magnetic field* used in the method is selected from the [Cnps] *low frequency pulsed magnetic fields* of FIG. 1, FIG. 3 or FIG. 5.

12. A method for treating a disorder selected from the group of physiological, neurological and behavioral disorders, said method comprising applying to a subject a specific low frequency pulsed magnetic field [(Cnp)], *each pulse having a plurality of intermittent waveforms, said waveforms being designed to initially generally mimic an endogenous electrical activity of target tissue of said subject, and to have a latency period between waveforms that varies in a predetermined manner over time, the application of said low frequency pulsed magnetic field being* for a time effective to produce a desired effect in [a] *said* target tissue and wherein the frequency of said waveforms [decrease] *decreases* over time.

13. The method of claim 1 wherein the frequency of said waveforms [increase] *increases* or [decrease] *decreases* over time.

15. The method of claim 1 wherein said [waveforms define variable latency periods, said] latency [periods being] *period is* selected to reduce the probability of neural excitement as the waveforms end.

20. A method of treating physiological, neurological and behavioral disorders comprising the step of subjecting target tissue to intermittent specific time varying low frequency magnetic fields for a duration effective to produce a desired effect, said intermittent magnetic fields being separated by refractory periods *and having waveforms designed to initially mimic generally an endogenous electrical activity of said target tissue and to have a lantency period between waveforms that varies in a predetermined manner over time*, and wherein said intermittent magnetic fields initially entrain the electrical acitivity of said target tissue and as a result affect [the] *said* endogenous electrical activity of said target tissue.

23. The method of claim 20 wherein the frequency of said waveforms [increase] *increases* or [decrease] *decreases* over time.

26. The method of claim 20 wherein said [wavefonns define variable latency periods, said] latency [periods being] *period is* selected to reduce the probability of neural excitement as the waveforms end.

28. A method of treating physiological, neurological and behavioral disorders comprising the step of subjecting target tissue to intermittent specific time varying low frequency magnetic fields for a duration effective to produce a desired effect, said intermittent magnetic fields being separated by refractory periods and having waveforms [configured relative to the target tissue] *designed to initially mimic generally an endogenous electrical activity of said target tissue and to have a latency period between waveforms that varies in a predetermined manner over time* and wherein the frequency of said waveforms [decrease] *decreases* over time.

*29. The method of claim 13, wherein said low frequency pulsed magnetic field is applied to target tissue in the central nervous system, and either slows down or speeds up the electrical activity of said target tissue.*

*30. The method of claim 1, wherein said method is used to treat pain.*

*31. The method of claim 1, wherein said method is used to treat anxiety.*

*32. The method of claim 1, wherein said method is used to treat epilepsy.*

*33. The method of claim 1, wherein said method is used to treat depression.*

*34. The method of claim 1, wherein said low frequency pulsed magnetic field includes as a design feature a delay to reduce excitation in said target tissue.*

* * * * *